(12) United States Patent
Mang et al.

(10) Patent No.: US 8,071,643 B2
(45) Date of Patent: Dec. 6, 2011

(54) PLEUROMUTILIN DERIVATIVES FOR THE TREATMENT OF DISEASES MEDIATED BY MICROBES

(75) Inventors: Rosemarie Mang, Vienna (AT); Werner Heilmayer, Zillingtal (AT); Rudolf Badegruber, Vienna (AT); Dirk B. Strickmann, Vienna (AT); Rodger Novak, Vienna (AT); Mathias Ferencic, Vienna (AT); Atchyuta Rama Chandra Murty Bulusu, Perchtoldsdorf (AT)

(73) Assignee: Nabriva Therapeutics AG, Vienna (AT)

( * ) Notice: Subject to any disclaimer, the term of this patent is extended or adjusted under 35 U.S.C. 154(b) by 303 days.

(21) Appl. No.: 12/531,839

(22) PCT Filed: Mar. 19, 2008

(86) PCT No.: PCT/AT2008/000097
§ 371 (c)(1),
(2), (4) Date: Sep. 17, 2009

(87) PCT Pub. No.: WO2008/113089
PCT Pub. Date: Sep. 25, 2008

(65) Prior Publication Data
US 2010/0035987 A1 Feb. 11, 2010

(30) Foreign Application Priority Data
Mar. 20, 2007 (EP) .................................. 07450053

(51) Int. Cl.
*A61K 31/215* (2006.01)
*C07C 323/00* (2006.01)
(52) U.S. Cl. ........................................ 514/529; 560/153
(58) Field of Classification Search .................. None
See application file for complete search history.

(56) References Cited

U.S. PATENT DOCUMENTS
2003/0162831 A1 * 8/2003 Ascher et al. .................. 514/529

FOREIGN PATENT DOCUMENTS
| DE | 4023848 A1 | 1/1992 |
|---|---|---|
| WO | 02/04414 A1 | 1/2002 |
| WO | 03/090740 | 6/2003 |
| WO | 03/082260 | 9/2003 |
| WO | 2007/000004 A1 | 1/2007 |
| WO | 2007/014409 A1 | 2/2007 |

OTHER PUBLICATIONS

Clinical and Laboratory Standards Institute (CLSI, former NCCLS) Document M7-A7 vol. 26, No. 2: "Methods for dilution Antimicrobial Susceptibility Tests for Bacteria that Grow Aerobically—Approved Standard; Seventh Edition", Jan. 2006.
Clinical and Laboratory Standards Institute (CLSI, former NCCLS), Document , M11-A6, vol. 24, No. 2: "Methods for Antimicrobial Susceptibility Testing of Anaerobic Bacteria—Approved Standard; Sixth Edition" 2004.

H. Berner, et al "Synthese AB-Trans-Anellierter Derivate DES Tricyclischen Diterpens Pleuromutilin Durch Intramolekulare 1,5-Hydrid-Verschiebung" Tetrahedron, vol. 36, No. 12-l, pp. 1807 to 1811, Pergamon Press Ltd., 1980, Great Britain.
Elena Gomez-Sanchez, et al "Synthesis and transformations of alkyl N-(1-cyclohex-3-enyl)carbamates prepared from cyclohex-3-ene carboxylic acid via Curtius rearrangement" Tetrahedron vol. 61, 2005, pp. 1207-1219.
Judith C. Amburgey, et al "Small Molecule Analogs of Phospholipid-Metal Ion Binding Sites: Synthesis and Molecular Modeling of Cyclohexane-1,2,4-triol Trisphosphates" Bioorganic Chemistry, 22, 1994, pp. 172-197.
Peter Kapferer, et al "Electrophilic Bromination of N-Acylated Cyclohex-3-en-1-amines: Synthesis of 7-Azanorbornanes" Helvetica Chimica Acta, vol. 87, 2004, pp. 2764-2789.
Peter O'Brien, et al "cis- and trans-Stereoselective Epoxidation of N-Protected 2-Cyclohexen-1-ylamines" Organic Letters, vol. 5, No. 26, 2003, pp. 4955-4957.
Liming Zhang, et al "Stereocontrolled Synthesis of Kelsoene by the Homo-Favorkii Rearrangement" Organic Letters, vol. 4, No. 21, 2002, pp. 3755-3758.
Yashwant D. Vankar, et al "Chiral Acetals in Organic Synthesis: Regioselective Synthesis of 2—and 3-Hydroxy Acetals from 2,3-Olefinic Acetals. Reinvestigation and Further Applications" Tetrahedron, vol. 50, No. 7, 1994, pp. 11057-11078.
Helmut Egger, et al "New Pleuromutilin Derivatives with Enhanced Antimicrobial Activity" The Journal of Antibiotics, vol. XXIX, No. 9, 1976, pp. 915-927.
B. Raju, et al "Conformationally restricted analogs of deoxynegamycin" Bioorganic & Medicinal Chemistry Letters, 14, 2004, pp. 3103-3107.
Elliot N. Marvell, et al "Products of Acetolysis of 3-(3-Cyclohexenyl)propyl and 4-(3-Cyclohexenyl_butyl p-Toluenesulfonates" Journal of Organic Chemistry, vol. 33, No. 7, Jul. 1968, pp. 2291-2993.

* cited by examiner

Primary Examiner — Paul A Zucker
(74) Attorney, Agent, or Firm — Workman Nydegger

(57) ABSTRACT

A pleuromutilin derivative compound of general formula (I)

I

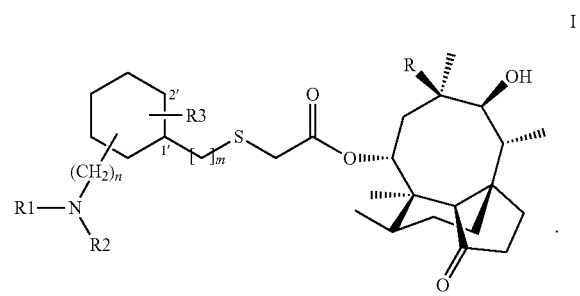

11 Claims, No Drawings

PLEUROMUTILIN DERIVATIVES FOR THE TREATMENT OF DISEASES MEDIATED BY MICROBES

The present invention relates to organic compounds, namely pleuromutilins.

Pleuromutilin, a compound of formula A

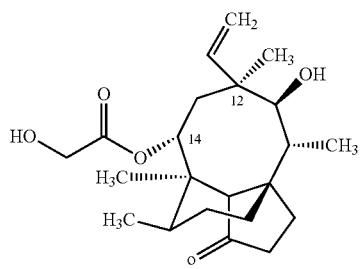

is a naturally occurring antibiotic, e.g. produced by the *basidomycetes Pleurotus mutilus* and *P. passeckerianus*, see e.g. The Merck Index, 13th edition, item 7617. A number of further pleuromutilins having the principle ring structure of pleuromutilin and being substituted at the hydroxy group have been developed, e.g. as antimicrobials.

From WO 02/04414 A1 pleuromutilin derivatives, e.g. 14-O-[(Aminocyclohexan-2-yl (and -3-yl)-sulfanyl)-acetyl]-mutilins; from WO 07/014,409 A1 e.g. 14-O-[((Mono- or dialkylamino)-cycloalkylsulfanyl)-acetyl]-mutilins and from WO 07/000,004 A1 e.g. [((Acyl-hydroxy-amino)-cycloalkylsulfanyl)-acetyl]-mutilins, are known.

We have now found pleuromutilins with interesting activity combined with an unexpected remarkable metabolic stability.

The pleuromutilin derivatives according to the invention are compounds of formula (I)

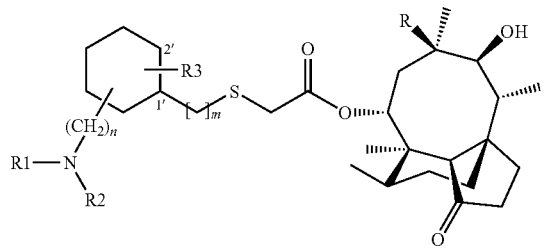

wherein
n is 0 to 4;
m is 0 or 1 with the proviso that the sulphur atom and $R_3$ are in vicinal position (if m=0 then $R_3$ is in position 2', and if m=1 then $R_3$ is on position 1');
R is ethyl or vinyl;
$R_1$ is hydrogen or $(C_{1-6})$alkyl,
$R_2$ is hydrogen or
  $(C_{3-6})$cycloalkyl, or
  unsubstituted $(C_{1-6})$alkyl, or
  $(C_{1-6})$alkyl substituted by one or more of
    hydroxy; preferably one or two,
    methoxy,
    halogen,
    $(C_{3-6})$cycloalkyl, or $R_1$ and $R_2$ together with the nitrogen atom to which they are attached form a 5 to 7 membered heterocyclic ring containing at least 1 nitrogen atom or 1 nitrogen and 1 additional heteroatome e.g. selected from N or O, or
$R_1$ is hydroxy and $R_2$ is formyl;
$R_3$ is OH, $OR_4$, a halogen atom, or
  with the proviso that $R_3$ is bound to 2' $R_3$ represents —O—$(CH_2)_p$—O— with p is 2 or 3;
$R_4$ is unsubstituted $(C_{1-6})$alkyl or $(C_{3-6})$cycloalkyl.

Preferred compounds of the present invention are compounds of formula (II)

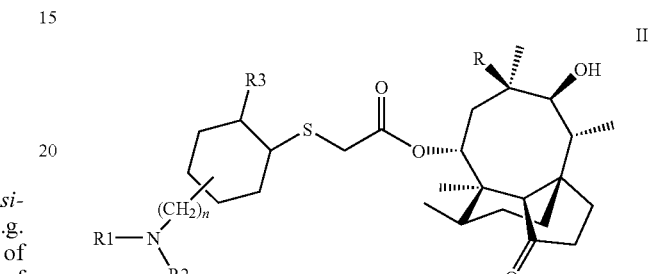

wherein n, R, $R_1$, $R_2$ and $R_3$ are as defined above.

More preferred compounds of the present invention are compounds of formula (III)

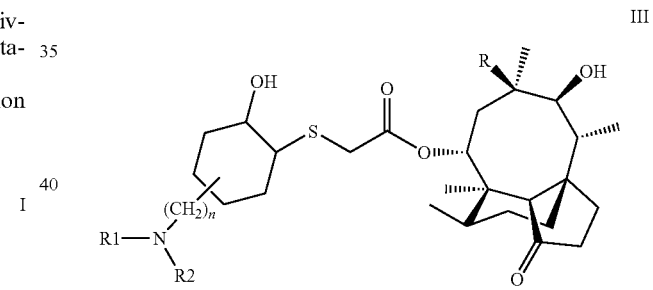

wherein n, R, $R_1$ and $R_2$ are as defined above.

Most preferred compounds of the present invention are
a compound of formula (IV)

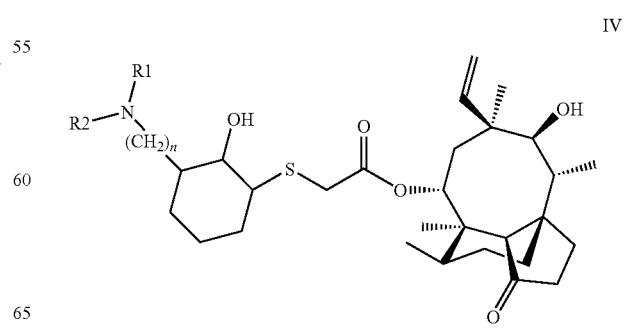

a compound of formula (V)

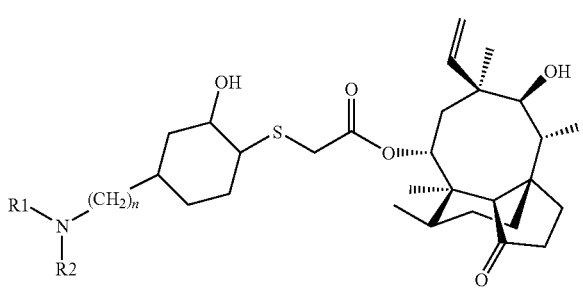

and
a compound of formula (VI)

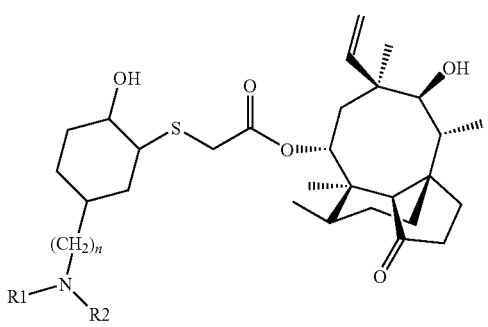

wherein n, $R_1$ and $R_2$ are as defined above.

Particularly preferred is a compound selected from the group consisting of

14-O-{[(1R,2R,4R)-4-Amino-2-hydroxy-cyclohexylsulfanyl]-acetyl}-mutilin

14-O-{[(1S,2S,4S)-4-Amino-2-hydroxy-cyclohexylsulfanyl]-acetyl}-mutilin

14-O-{[(1R,2R,5S)-5-Amino-2-hydroxy-cyclohexylsulfanyl]-acetyl}-mutilin

14-O-{[(1S,2S,5R)-5-Amino-2-hydroxy-cyclohexylsulfanyl]-acetyl}-mutilin

14-O-{[(1R,2R,4S)-4-Amino-2-hydroxy-cyclohexylsulfanyl]-acetyl}-mutilin and the (1S,2S,4R) diastereomer thereof 14-O-{[(1R,2R,5R)-5-Amino-2-hydroxy-cyclohexylsulfanyl]-acetyl}-mutilin 14-O-{[(1S,2S,5S)-5-Amino-2-hydroxy-cyclohexylsulfanyl]-acetyl}-mutilin 14-O-{[(1R,2R,3R)-3-Amino-2-hydroxy-cyclohexylsulfanyl]-acetyl}-mutilin and the (1S,2S,3S) diastereomer thereof 14-O-{[(1R,2R,4R)-4-Diethylamino-2-hydroxy-cyclohexylsulfanyl]-acetyl}-mutilin and the (1S,2S,4S) diastereomer thereof 14-O-{[(1R,2R,4R)-4-Ethylamino-2-hydroxy-cyclohexylsulfanyl]-acetyl}-mutilin and the (1S,2S,4S) diastereomer thereof 14-O-{[(1R,2R,5S)-5-Ethylamino-2-hydroxy-cyclohexylsulfanyl]-acetyl}-mutilin and the (1S,2S,5R) diastereomer thereof 14-O-{[(1R,2R,5S)-5-Diethylamino-2-hydroxy-cyclohexylsulfanyl]-acetyl}-mutilin and the (1S,2S,5R) diastereomer thereof 14-O-{[(1R,2R,4S)-4-Diethylamino-2-hydroxy-cyclohexylsulfanyl]-acetyl}-mutilin and the (1S,2S,4R) diastereomer thereof 14-O-{[(1R,2R,5R)-5-Diethylamino-2-hydroxy-cyclohexylsulfanyl]-acetyl}-mutilin and the (1S,2S,5S) diastereomer thereof 14-O-{[(1R,2R,3R)-3-Ethylamino-2-hydroxy-cyclohexylsulfanyl]-acetyl}-mutilin and the (1S,2S,3S) diastereomer thereof 14-O-{[(1R,2R,3R)-3-Diethylamino-2-hydroxy-cyclohexylsulfanyl]-acetyl}-mutilin and the (1S,2S,3S) diastereomer thereof 14-O-{[(1R,2R,4S)-4-(Formyl-hydroxy-amino)-2-hydroxy-cyclohexylsulfanyl]-acetyl}-mutilin and the (1S,2S,4R) diastereomer thereof 14-O-{[(1R,2R,5S)-5-(Formyl-hydroxy-amino)-2-hydroxy-cyclohexylsulfanyl]-acetyl}-mutilin and the (1S,2S,5R) diastereomer thereof 14-O-{[(1R,2R,3R/S)-3-(Formyl-hydroxy-amino)-2-hydroxy-cyclohexylsulfanyl]-acetyl}-mutilin and the (1S,2S,3R/S) diastereomer thereof 14-O-{[(1R,2R,5S)-2-Hydroxy-5-methylamino-cyclohexylsulfanyl]-acetyl}-mutilin and the (1S,2S,5R) diastereomer thereof 14-O-{[(1R,2R,5S)-5-Allylamino-2-hydroxy-cyclohexylsulfanyl]-acetyl}-mutilin and the (1S,2S,5R) diastereomer thereof 14-O-{[(1R,2R,5S)-2-Hydroxy-5-(2-methoxy-ethylamino)-cyclohexylsulfanyl]-acetyl}-mutilin and the (1S,2S,5R) diastereomer thereof 14-O-{[(1R,2R,4R*)-2-Hydroxy-4-(2-hydroxy-ethylamino)-cyclohexylsulfanyl]-acetyl}-mutilin and the (1S,2S,4S*) diastereomer thereof 14-O-{[(1R,2R,4R*)-4-Cyclohexylamino-2-hydroxy-cyclohexylsulfanyl]-acetyl}-mutilin and the (1S,2S,4S*) diastereomer thereof 14-O-{[(1R,2R,4R*)-4-Cyclopropylamino-2-hydroxy-cyclohexylsulfanyl]-acetyl}-mutilin and the (1S,2S,4S*) diastereomer thereof 14-O-{[(1R,2R,5S*)-4-Cyclopropylamino-2-hydroxy-cyclohexylsulfanyl]-acetyl}-mutilin and the (1S,2S,5R*) diastereomer thereof 14-O-{[(1R,2R,4S*)-4-Cyclopropylamino-2-hydroxy-cyclohexylsulfanyl]-acetyl}-mutilin and the (1S,2S,4R*) diastereomer thereof 14-O-{[(1R,2R,5R*)-2-Hydroxy-5-morpholin-4-yl-cyclohexylsulfanyl]-acetyl}-mutilin and the (1S,2S,5S*) diastereomer thereof 14-O-{[(1R,2R,5S*)-2-Hydroxy-5-morpholin-4-yl-cyclohexylsulfanyl]-acetyl}-mutilin and the (1S,2S,5R*) diastereomer thereof 14-O-{[(1R,2R,5S)-5-Amino-2-hydroxy-cyclohexylsulfanyl]-acetyl}-19,20-dihydro-mutilin and the (1S,2S,5R) diastereomer thereof 14-O-{[(1R,2R,5S)-5-Ethylamino-2-hydroxy-cyclohexylsulfanyl]-acetyl}-19,20-dihydro-mutilin and the (1S,2S,5R) diastereomer thereof 14-O-{[(1R,2R,5R)-5-Amino-2-hydroxy-cyclohexylsulfanyl]-acetyl}-19,20-dihydro-mutilin and the (1S,2S,5S) diastereomer thereof 14-O-{[(1R,2R)-4-Aminomethyl-2-hydroxy-cyclohexylsulfanyl]-acetyl}-mutilin and the (1S,2S) diastereomers thereof 14-O-{[5-Amino-2-chloro-cyclohexylsulfanyl]-acetyl}-mutilin 14-O-{[4-Amino-2-chloro-cyclohexylsulfanyl]-acetyl}-mutilin 14-O-[(4-Amino-1-hydroxy-cyclohexylmethylsulfanyl)-acetyl]-mutilin 14-O-{[(1R,2R)-2-Hydroxy-5-(3-methylamino-propyl)-cyclohexylsulfanyl]-acetyl}-mutilin and the (1S,2S) diastereomers thereof 14-O-{[(1R,2R)-2-Hydroxy-4-(3-methylamino-propyl)-cyclohexylsulfanyl]-acetyl}-mutilin and the (1S,2S) diastereomers thereof 14-O-{[(1R,2R)-5-(3-Amino-propyl)-2-hydroxy-cyclohexylsulfanyl]-acetyl}-mutilin and the (1S,2S) diastereomers thereof 14-O-{[(1R,2R)-4-(3-Amino-propyl)-2-hydroxy-cyclohexylsulfanyl]-acetyl}-mutilin and the (1S,2S) diastereomer thereof 14-O-{[(6R,8R)-8-Amino-1,4-dioxa-spiro[4.5]dec-6-ylsulfanyl]-acetyl}-mutilin and the (6S,8S) diastereomer thereof 14-O-{[4-Amino-2-methoxy-cyclohexylsulfanyl]-acetyl}-mutilin and 14-O-{([5-Amino-2-methoxy-cyclohexylsulfanyl]-acetyl}-mutilin.

A compound provided by the present invention is herein also designated as "compound(s) of (according to) the present invention". A compound of the present invention includes a compound in any form, e.g. in free form, in the form of a salt, in the form of a solvate and in the form of a salt and a solvate.

According to another aspect, the present invention provides a compound of the present invention in the form of a salt and/or solvate.

The salts include preferably pharmaceutically acceptable salts, although pharmaceutically unacceptable salts are included, e.g. for preparation/isolation/purification purposes.

A salt of a compound of the present invention includes a base salt or an acid addition salt. Pharmaceutically acceptable base salts include ammonium salts such as trimethylammonium salt, alkali metal salts such as those of sodium and potassium, alkaline earth metal salts such as those of calcium and magnesium, and salts with organic bases, including salts of primary, secondary and tertiary amines, such as isopropylamine, diethylamine, ethanolamine, trimethylamine, dicyclohexyl amine and N-methyl-D-glucamine, preferably sodium salts. Acid addition salts include salts of a compound of the present invention with an acid, e.g. hydrogen fumaric acid, fumaric acid, tartaric acid, ethane-1,2-disulphonic acid, maleic acid, naphthalin-1,5-sulphonic acid, acetic acid, maleic acid, succinic acid, salicylic acid, azelaic acid, 2-[(2,6-dichlorophenyl)amino]benzene acetic acid, hydrochloric acid, deuterochloric acid, preferably hydrochloric acid.

A compound of the present invention in free form may be converted into a corresponding compound in the form of a salt, and vice versa. A compound of the present invention in free form or in the form of a salt and/or in the form of a solvate may be converted into a corresponding compound in free form or in the form of a salt in non-solvated form, and vice versa.

A compound of the present invention may exist in the form of isomers and mixtures thereof, e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates or diastereomeric mixtures. Any asymmetric carbon atom may be present in the (R)-, (S)- or (R,S)-configuration, preferably in the (R)- or (S)-configuration.

For example, in a compound of formula I the carbon atom of the cycloalkyl ring which is attached to $(CH_2)_mS$ group, the carbon atom of the cycloalkyl ring which is attached to the $R_3$ group, and the carbon atom of the cycloalkyl ring to which the $(CH_2)_nN(R_1R_2)$ group is attached, all are asymmetric carbon atoms. Substituents attached to such asymmetric carbon atom may thus exist in (R) and (S) configuration, including mixtures thereof. For example, if in a compound of formula I $R_2$ is substituted alkyl and that substituent is attached to a carbon atom of the side chain of such alkyl, the carbon atom to which such substituent is attached is an asymmetric carbon atom and such substituent may be in the (R)- and (S)-configuration, including mixtures thereof.

The configuration of substituents attached to asymmetric carbon atoms of the mutilin-tricyclus is preferably the same as in natural pleuromutilin.

Isomeric mixtures may be separated as appropriate, e.g. according, e.g. analogously, to a method as conventional, to obtain pure isomers. The present invention includes a compound of the present invention in any isomeric form and in any isomeric mixture. The present invention also includes tautomers of a compound of the present invention, where tautomers can exist.

The compounds of the present invention exhibit pharmacological activity and are therefore useful as pharmaceuticals.

For example, the compounds of the present invention show antimicrobial, e.g. antibacterial, activity against gram positive bacteria, such as coagulase positive Staphylococci, e.g. *Staphylococcus aureus*, coagulase negative Staphylococci, e.g. *Staphylococcus epidermidis, Staphylococcus haemolyticus*, and Streptococci, e.g. *Streptococcus pyogenes, Streptococcus pneumoniae*, Enterococci, e.g. *Enterococcus faecium* and *Listeria monocytogenes* and against gram negative bacteria such as *Moraxella*, e.g. *Moraxella catarrhalis*, and *Haemophilus*, e.g. *Haemophilus influenzae*, and *Legionella*, e.g. *Legionella pneumophila*, Neisseriaceae, e.g. *Neisseria gonorrhoeae*, as well as against *Mycoplasms, Chlamydia* and obligatory anaerobes, e.g. *Bacteroides fragilis, Clostridium difficile, Fusobacterium* spp., and *Propionibacterium* spp.

The in vitro activity against aerobic bacteria was determined by Agar Dilution Test or Microdilution Test according to the Clinical and Laboratory Standards Institute (CLSI, former NCCLS) Document M7-A7 Vol. 26, No. 2: "Methods for dilution Antimicrobial Susceptibility Tests for Bacteria that Grow Aerobically—Approved Standard; Seventh Edition (2006)"; and the test against anaerobic bacteria was performed according to the Clinical and Laboratory Standards Institute (CLSI, former NCCLS), Document, M11-A6, Vol. 24, No. 2: "Methods for Antimicrobial Susceptibility Testing of Anaerobic Bacteria—Approved Standard; Sixth Edition (2004)" and the in vivo activity was tested by the septicaemia mouse model against *Staphylococcus aureus*.

Compounds of the present invention are therefore suitable for the treatment and prevention of diseases which are mediated by microbes, e.g. by bacteria. Diseases which may also be treated include e.g. diseases mediated by *Helicobacter*, such as *Helicobacter pylori*, and diseases mediated by *Mycobacterium tuberculosis*. Diseases which may also be treated include in general inflammatory diseases, where microbes are mediating said inflammation, e.g. including acne.

In another aspect the present invention provides a compound of the present invention for use as a pharmaceutical, preferably as an antimicrobial, such as an antibiotic, e.g. and an anti-anaerobic.

In another aspect the present invention provides a compound of the present invention for use in acne treatment.

In a further aspect the present invention provides a compound of the present invention for use in the preparation of a medicament for the treatment of diseases, mediated by microbes, such as bacterials, for example diseases mediated by bacteria, e.g. selected from Staphylococci, Streptococci, Enterococci;

diseases mediated by bacteria, e.g. selected from *Moraxella, Haemophilus, Legionella*, Neisseriaceae;

diseases mediated by *Helicobacter*;

diseases mediated by *Mycobacterium tuberculosis*;

e.g. diseases mediated by *Mycoplasms, Chlamydia* and obligatory anaerobes; and for the treatment of acne.

In a further aspect the present invention provides a method of treatment of diseases mediated by microbes which comprises administering to a subject in need of such treatment an effective amount of a compound of the present invention e.g. in the form of a pharmaceutical composition.

In a further aspect the present invention provides a method of treatment of acne which comprises administering to a subject in need of such treatment an effective amount of a compound of the present invention e.g. in the form of a pharmaceutical composition.

Treatment includes treatment and prophylaxis.

For antimicrobial and acne treatment, the appropriate dosage will, of course, vary depending upon, for example, the chemical nature and the pharmacokinetic data of a compound of the present invention employed, the individual host, the mode of administration and the nature and severity of the conditions being treated. However, in general, for satisfactory results in larger mammals, for example humans, an indicated daily dosage is in the range from about 0.5 mg to 3 g of a compound of the present invention conveniently administered, for example, in divided doses up to four times a day.

A compound of the present invention may be administered by any conventional route, for example enterally, e.g. including nasal, buccal, rectal, oral administration; parenterally, e.g. including intravenous, intramuscular, subcutaneous administration; or topically, e.g. including epicutaneous, intranasal, intratracheal administration, e.g. in form of coated or uncoated tablets, capsules, injectable solutions or suspensions, e.g. in the form of ampoules, vials, in the form of creams, gels, pastes, inhaler powder, foams, tinctures, lip sticks, drops, sprays, or in the form of suppositories, e.g. in analogous manner to macrolides, such as erythromycins, e.g. clarithromycin or azithromycin.

A compound of the present invention may be administered in the form of a pharmaceutically acceptable salt, e.g. an acid addition salt or a base addition salt, e.g. a metal salt, or in free form, optionally in the form of a solvate. A compound of the present invention in the form of a salt exhibits the same order of activity as the compound in free form, optionally in the form of a solvate.

A compound of the present invention may be used for pharmaceutical treatment according to the present invention alone or in combination with one or more other pharmaceutically active agents. Such other pharmaceutically active agents include e.g. other antibiotics and antiinflammatory agents, and, if a compound of the present invention is used in the treatment of acne, other pharmaceutically agents include furthermore agents which are active against acne.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention in free form or in the form of a pharmaceutically acceptable salt and/or in the form of a solvate in association with at least one pharmaceutical, excipient, e.g. carrier or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such pharmaceutical compositions may be manufactured according, e.g. analogously, to a method as conventional, e.g. by mixing, granulating, coating, dissolving or lyophilizing processes. Unit dosage form may contain, for example, from about 0.5 mg to about 2000 mg, such as 10 mg to about 500 mg.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves, e.g., and for diluting fluids for artificial insemination and for egg-dipping techniques.

In another aspect the present invention provides a compound of the present invention for use as a veterinary agent.

In a further aspect the present invention provides a compound of the present invention for the preparation of a veterinary composition which is useful as a veterinary agent.

In another aspect the present invention provides a veterinary method for the prophylaxis and the treatment of microbial, e.g. bacterial diseases which comprises administering to a subject in need of such treatment an effective amount of a compound of the present invention, e.g. in the form of a veterinary composition.

Examples 1 to 37 following thereafter exhibit MICs$\leqq$ 2 µg/ml against *Staphylococcus aureus* ATCC49951 and *Streptococcus pneumoniae* ATCC49619.

The metabolic stability for compounds of the present invention was determined by using cryopreserved primary human hepatocytes, $1\times10^6$ cells/mL were incubated in the absence and the presence of 5 and 25 µg/mL of the test compounds at 37° C., 5% $CO_2$ for 4 hours. To evaluate the in vitro degradation under assay conditions, a sample of each test compound was incubated also in the absence of hepatocytes. The incubation was stopped by freezing the reaction mixture. After ultrafiltration and washing of the filter with acetonitrile, the sample solution was analyzed for parent compound disappearance or metabolite appearance using LC/MS (ion trap). The metabolic stability value corresponds to the detected parent compound in % after incubation.

At the compounds of the present invention, the introduction of the $R_3$ group, preferably a hydroxy group, in vicinal position to the sulphur substituent attached to the cyclohexyl ring reveals unexpected improvements in metabolic stability of the microbiologically active components. Parent compound or active metabolite were more stable after incubation with primary human hepatocytes in comparison to derivatives without the $R_3$ group, preferably the hydroxy group, attached to the cyclohexyl moiety of the pleuromutilin side chain.

For example after 4 h incubation with human hepatocytes at a compound concentration of 5 µg/mL, for a mixture of 14-O-{[(1R,2R,5S)-5-Amino-2-hydroxy-cyclohexylsulfanyl]-acetyl}-mutilin hydrochloride and the (1S,2S,5R) diastereomer hydrochloride thereof—Example 2 of the present invention—66% of parent compounds were found, whereas for mixture of 14-O-{[(1R,3R)-3-Amino-cyclohexylsulfanyl]-acetyl}-mutilin hydrochloride and the (1S,3S) diastereomer hydrochloride thereof—analogous derivative without hydroxyl group—only 24% of parent compounds could be detected.

EXAMPLES

The trivial name mutilin refers to the IUPAC systematic name (1S,2R,3S,4S,6R,7R,8R, 14R)-3,6-dihydroxy-2,4,7,14-tetramethyl-4-vinyl-tricyclo[5.4.3.0$^{1,8}$]tetradecan-9-one. In the examples, pleuromutilin derivatives are numbered in analogy to the mutilin numbering system described by H. Berner (Berner, H.; Schulz, G.; Schneider H. *Tetrahedron* 1980, 36, 1807-1811.):

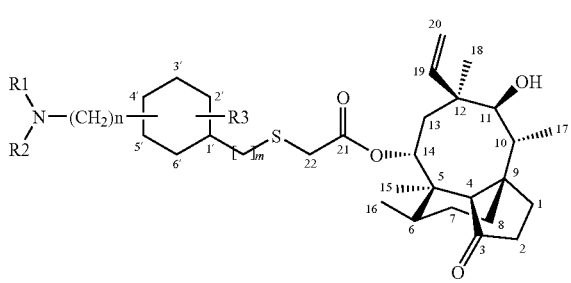

Pleuromutilin thiol and pleuromutilin tosylate are compounds of formulae:

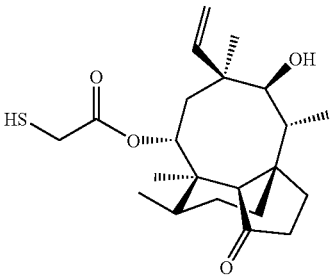

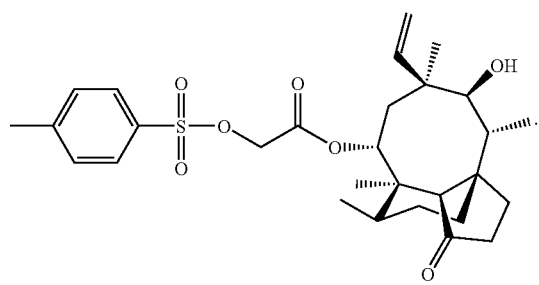

Example 1

14-O-{[(1R,2R,4R)-4-Amino-2-hydroxy-cyclohexylsulfanyl]-acetyl}-mutilin hydrochloride+(1S,2S,4S) Diastereomer Hydrochloride Step A1. 14-O-{[(1R,2R,4R)-4-tert-Butoxycarbonylamino-2-hydroxy-cyclohexylsulfanyl]-acetyl}-mutilin+(1S,2S,4S) Diastereomer and 14-O-{[(1R,2R,5S)-5-tert-Butoxycarbonylamino-2-hydroxy-cyclohexylsulfanyl]-acetyl}-mutilin+(1S,2S,5R) Diastereomer and 14-O-{[(1R,2R,4S)-4-tert-Butoxycarbonylamino-2-hydroxy-cyclohexylsulfanyl]-acetyl}-mutilin+(1S,2S,4R) Diastereomer To a solution of 3,4-epoxycyclohexyl-carbamic acid tert-butyl ester (Gómez-Sánchez, E.; Marco-Contelles J. *Tetrahedron* 2005, 61, 1207-1219.) (4.27 g, 20 mmol) and pleuromutilin thiol (Nagarajan, R. Eli Lilly and Company 1978, U.S. Pat. No. 4,130,709) (7.10 g, 18 mmol) in 200 ml of tetrahydrofuran was added aluminum oxide (40 g, Brockmann activity I, neutral) and the resulting mixture was stirred for 40 hours at room temperature. The suspension was filtered and concentrated under reduced pressure. The residue was subjected to chromatography (silica, cyclohexane/ethyl acetate=1/1) to yield 14-O-{[(1R,2R,4R)-4-tert-butoxycarbonylamino-2-hydroxy-cyclohexylsulfanyl]-acetyl}-mutilin+(1S,2S,4S) diastereomer (a) ($R_f$=0.38, 1.34 g, 12%) as well as a mixture of 14-O-{[(1R,2R,5S)-5-tert-butoxycarbonylamino-2-hydroxy-cyclohexylsulfanyl]-acetyl}-mutilin+(1S,2S,5R) diastereomer and 14-O-{[(1R,2R,4S)-4-tert-butoxycarbonylamino-2-hydroxy-cyclohexylsulfanyl]-acetyl}-mutilin+(1S,2S,4R) diastereomer (b) ($R_f$=0.26, 2.81 g, 25%) as colorless amorphous foams.

(a): $^1$H NMR (400 MHz, DMSO-$d_6$, δ, ppm, inter alia): 6.74 (d, 1H, NH, J=7 Hz), 6.13 (dd, 1H, 19-H, J=11 Hz and 18 Hz), 5.54 (d, 1H, 14-H, J=8 Hz), 5.05 (m, 2H, 20-H), 4.90 (d, 1H, 2'-OH, J=5 Hz), 4.48 (d, 1H, 11-OH, J=6 Hz), 3.55-3.20 (m, 6H, 1'-H, 2'-H, 4'-H, 11-H, 22-H), 2.40 (bs, 1H, 4-H), 1.36 (s, 3H, 15-CH$_3$), 1.35 (s, 9H, tert-butyl), 1.06 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 630 (MNa$^+$), 1237 (2MNa$^+$).

(b): $^1$H NMR (400 MHz, DMSO-$d_6$, δ, ppm, inter alia): 6.70 (d, 1H, NH, J=7 Hz), 6.12 (dd, 1H, 19-H, J=11 Hz and 18 Hz), 5.34 (d, 1H, 14-H, J=8 Hz), 5.05 (m, 2H, 20-H), 4.82, 4.78 (d, 1H, 2'-OH, J=4 Hz), 4.48 (d, 1H, 11-OH, J=6 Hz), 3.55-3.20 (m, 5H, 2'-H, 4'/5'-H, 11-H, 22-H), 2.97 (m, 1H, 1'-H), 2.40 (bs, 1H, 4-H), 1.35 (s, 12H, 15-CH$_3$, tert-butyl), 1.05 (s, 3H, 18-CH$_3$), 0.82 (d, 3H, 17-CH$_3$, J=7 Hz), 0.62 (d, 3H, 16-CH$_3$, J=7 Hz). MS-ESI (m/z): 630 (MNa$^+$), 1237 (2MNa$^+$).

Or Step A2. 14-O-{[(1R,2R,4R)-4-tert-Butoxycarbonylamino-2-hydroxy-cyclohexylsulfanyl]-acetyl}-mutilin+(1S,2S,4S) Diastereomer and 14-O-{[(1R,2R,5S)-5-tert-Butoxycarbonylamino-2-hydroxy-cyclohexylsulfanyl]-acetyl}-mutilin+(1S,2S,5R) Diastereomer and 14-O-{[(1R,2R,4S)-4-tert-Butoxycarbonylamino-2-hydroxy-cyclohexylsulfanyl]-acetyl}-mutilin+(1S,2S,4R) Diastereomer To a solution of 3,4-epoxycyclohexyl-carbamic acid tert-butyl ester (10 g, 47 mmol) and pleuromutilin thiol (16.6 g, 42 mmol) in 200 ml of methanol and 20 ml of dioxane was added 2N NaOH (21 ml, 42 mmol) and the resulting mixture was stirred for 16 hours at room temperature. After completion of the reaction the pH was set to 7 with diluted HCl and the reaction mixture was concentrated under reduced pressure. The residue was diluted with water and brine and extracted three times with ethyl acetate. The organic layers were dried over sodium sulfate and filtered. The filtrate was concentrated under reduced pressure and after chromatography (silica, cyclohexane/ethyl acetate=1/1) 14-O-{[(1R,2R,4R)-4-tert-butoxycarbonylamino-2-hydroxy-cyclohexylsulfanyl]-acetyl}-mutilin+(1S,2S,4S) diastereomer ($R_f$=0.40, 3.1 g, 12% yield) as well as a mixture of 14-O-{[(1R,2R,5S)-5-tert-butoxycarbonylamino-2-hydroxy-cyclohexylsulfanyl]-acetyl}-mutilin+(1S,2S,5R) diastereomer and 14-O-{[(1R,2R,4S)-4-tert-butoxycarbonylamino-2-hydroxy-cyclohexylsulfanyl]-acetyl}-mutilin+(1S,2S,4R) diastereomer ($R_f$=0.25, 6.35 g, 25%) were obtained as colorless amorphous foams.

Or Step A3. 14-O-{[(1R,2R,4R)-4-tert-Butoxycarbonylamino-2-hydroxy-cyclohexylsulfanyl]-acetyl}-mutilin+(1S,2S,4S) Diastereomer and 14-O-{[(1R,2R,5S)-5-tert-Butoxycarbonylamino-2-hydroxy-cyclohexylsulfanyl]-acetyl}-mutilin+(1S,2S,5R) Diastereomer To a solution of Pleuromutilin thiol (9.25 g, 23.5 mmol) in 100 ml of acetonitrile (dried over 4 Å molecular sieve) was added 1,5-diazabicyclo[4.3.0]non-5-ene (DBN, 2.9 µl, 23.5 mmol) and after 1 hour of stirring at room temperature under argon atmosphere the mixture was charged with syn-3,4-epoxycyclohexyl-carbamic acid tert-butyl ester (4.17 g, 19.5 mmol) and stirred for further 16 hours at room temperature. The reaction mixture was concentrated under reduced pressure. The residue was charged with water and brine and extracted three times with dichloromethane. The organic layers were dried over sodium sulphate and filtered. The filtrate was concentrated under reduced pressure and subjected to chromatography (silica, cyclohexane/ethyl acetate=1/1) to yield 14-O-{[(1R,2R,4R)-4-tert-butoxycarbonylamino-2-hydroxy-cyclohexylsulfanyl]-acetyl}-mutilin+(1S,2S,4S) diastereomer ($R_f$=0.38, 5.07 g, 43%) as well as 14-O-{[(1R,2R,5S)-5-tert-butoxycarbonylamino-2-hydroxy-cyclohexylsulfanyl]-acetyl}-mutilin+(1S,2S,5R) diastereomer ($R_f$=0.25, 2.95 g, 16.5%) as colorless amorphous foams.

Step B. 14-O-{[(1R,2R,4R)-4-Amino-2-hydroxy-cyclohexylsulfanyl]-acetyl}-mutilin+(1S,2S,4S) Diastereomer To a solution of 14-O-{[(1R,2R,4R)-4-tert-butoxycarbonylamino-2-hydroxy-cyclohexylsulfanyl]-acetyl}-mutilin+(1S,2S,4S) diastereomer (1.34 g, 2.20 mmol) in 75 ml of dichloromethane was added trifluoroacetic acid-(4 ml) at 4° C. and stirred for 5 hours at room temperature. The reaction mixture was diluted with dichloromethane and cautiously poured into a saturated NaHCO$_3$ solution. The phases were separated and the aqueous layer was washed two times with dichloromethane. The combined organic layers are dried over sodium sulfate and filtered. After chromatography (silica, ethyl acetate/methanol/35% ammonia solution=50/50/1) 14-O-{[(1R,2R,4R)-4-amino-2-hydroxy-cyclohexylsulfanyl]-acetyl}-mutilin+(1S,2S,4S) diastereomer (745 mg, 67% yield) was obtained as colorless amorphous foam.

$^1$H NMR (400 MHz, DMSO-d$_6$, δ, ppm, inter alia): 6.14 (dd, 1H, 19-H, J=11 Hz and 18 Hz), 5.54 (d, 1H, 14-H, J=8 Hz), 5.05 (m, 2H, 20-H), 4.50 (d, 1H, 11-OH, J=6 Hz), 3.50-3.20 (m, 5H, 2'-H, 4'-H, 11-H, 22-H), 2.55 (m, 1H, 1'-H), 2.40 (bs, 1H, 4-H), 1.35 (s, 3H, 15-CH$_3$), 1.06 (s, 3H, 18-CH$_3$), 0.82 (d, 3H, 17-CH$_3$, J=7 Hz), 0.62 (d, 3H, 16-CH$_3$, J=7 Hz). MS-ESI (m/z): 508 (MH$^+$), 530 (MNa$^+$), 1015 (2 MH$^+$), 1037 (2MNa$^+$).

Step C. 14-O-{[(1R,2R,4R)-4-Amino-2-hydroxy-cyclohexylsulfanyl]-acetyl}-mutilin hydrochloride+ (1S,2S,4S) Diastereomer Hydrochloride A solution of 14-O-{[(1R,2R,4R)-4-amino-2-hydroxy-cyclohexylsulfanyl]-acetyl}-mutilin+(1S,2S,4S) diastereomer (325 mg, 0.64 mmol) in 20 ml of dioxane was treated with 1N HCl (0.64 ml, 0.64 mmol). After stirring at room temperature for 30 minutes the solution was lyophilized to obtain 14-O-{[(1R,2R,4R)-4-amino-2-hydroxy-cyclohexylsulfanyl]-acetyl}-mutilin hydrochloride+(1S,2S,4S) diastereomer hydrochloride (quantitative yield) as colorless amorphous solid.

$^1$H NMR (500 MHz, DMSO-d$_6$, δ, ppm, inter alia): 7.6 (bs, 3H, NH$_3^+$), 6.14 (dd, 1H, 19-H, J=11 Hz and 18 Hz), 5.55 (d, 1H, 14-H, J=8 Hz), 5.05 (m, 2H, 20-H), 4.52 (d, 1H, 11-OH, J=6 Hz), 3.50-3.20 (m, 4H, 2'-H, 1-H, 22-H), 3.03 (m, 1H, 4'-H), 2.53 (m, 1H, 1'-H), 2.40 (bs, 1H, 4-H), 1.37 (s, 3H, 15-CH$_3$), 1.06 (s, 3H, 18-CH$_3$), 0.82 (d, 3H, 17-CH$_3$, J=7 Hz), 0.62 (d, 3H, 16-CH$_3$, J=7 Hz). MS-ESI (m/z): 508 (MH$^+$), 530 (MNa$^+$), 1015 (2 MH$^+$), 1037 (2MNa$^+$), 542 (MCl$^-$).

Example 1A

14-O-{[(1S,2S,4S)-4-Amino-2-hydroxy-cyclohexylsulfanyl]-acetyl}-mutilin and 14-O-{[(1R,2R,4R)-4-Amino-2-hydroxy-cyclohexylsulfanyl]-acetyl}-mutilin The mixture of 14-O-{[(1R,2R,4R)-4-Amino-2-hydroxy-cyclohexylsulfanyl]-acetyl}-mutilin+(1S,2S,4S) diastereomer (12 g, 23.6 mmol) from Example 1 Step B was separated on a chiral column (250×20 mm CHIRALCEL OD-H, n-heptane/ethanol/diethylamine=80/20/0.1) to yield 14-O-{[(1S*,2S*,4S*)-4-amino-2-hydroxy-cyclohexylsulfanyl]-acetyl}-mutilin (a) (early eluting compound, 4.76 g, 37% yield, uncorrected) and 14-O-{[(1R*,2R*,4R*)-4-amino-2-hydroxy-cyclohexylsulfanyl]-acetyl}-mutilin (b) (late eluting compound, 3.63 g, 30% yield, uncorrected) as colorless amorphous foams.

(a): $^1$H NMR (400 MHz, DMSO-d$_6$, δ, ppm, inter alia): 6.13 (dd, 1H, 19-H, J=11 Hz and 18 Hz), 5.54 (d, 1H, 14-H, J=8 Hz), 5.05 (m, 2H, 20-H), 4.50 (d, 1H, 11-OH, J=6 Hz), 3.50-3.20 (m, 5H, 2'-H, 4'-H, 11-H, 22-H), 2.55 (m, 1H, 1'-H), 2.40 (bs, 1H, 4-H), 1.35 (s, 3H, 15-CH$_3$), 1.05 (s, 3H, 18-CH$_3$), 0.82 (d, 3H, 17-CH$_3$, J=7 Hz), 0.62 (d, 3H, 16-CH$_3$, J=7 Hz). MS-ESI (m/z): 508 (MH$^+$), 530 (MNa$^+$), 1015 (2 MH$^+$), 1037 (2MNa$^+$), 506 (M-H)$^-$, 542 (MCl$^-$).

(b): $^1$H NMR (400 MHz, DMSO-d$_6$, δ, ppm, inter alia): 6.13 (dd, 1H, 19-H, J=11 Hz and 18 Hz), 5.54 (d, 1H, 14-H, J=8 Hz), 5.05 (m, 2H, 20-H), 4.50 (d, 1H, 11-OH, J=6 Hz), 3.50-3.20 (m, 5H, 2'-H, 4'-H, 1-H, 22-H), 2.55 (m, 1H, 1'-H), 2.40 (bs, 1H, 4-H), 1.35 (s, 3H, 15-CH$_3$), 1.05 (s, 3H, 18-CH$_3$), 0.82 (d, 3H, 17-CH$_3$, J=7 Hz), 0.62 (d, 3H, 16-CH$_3$, J=7 Hz). MS-ESI (m/z): 508 (MH$^+$), 530 (MNa$^+$), 1015 (2 MH$^+$), 1037 (2MNa$^+$), 506 (M-H)$^-$, 542 (MCl$^-$).

Example 2

14-O-{1-[(1R,2R,5S)-5-Amino-2-hydroxy-cyclohexylsulfanyl]-acetyl}-mutilin hydrochloride+(1S,2S,5R) Diastereomer Hydrochloride

Step A. 14-O-{[(1R,2R,5S)-5-Amino-2-hydroxy-cyclohexylsulfanyl]-acetyl}-mutilin+(1S,2S,5R) Diastereomer and 14-O-{[(1R,2R,4S)-4-Amino-2-hydroxy-cyclohexylsulfanyl]-acetyl}-mutilin+(1S,2S,4R) Diastereomer A mixture of 14-O-{[(1R,2R,5S)-5-tert-butoxycarbonylamino-2-hydroxy-cyclohexylsulfanyl]-acetyl}-mutilin+ (1S,2S,5R) diastereomer and 14-O-{[(1R,2R,4S)-4-tert-butoxycarbonylamino-2-hydroxy-cyclohexylsulfanyl]-acetyl}-mutilin+(1S,2S,4R) diastereomer (1.12 g, 1.84 mmol) from Example 1 Step A was treated according to the method of Example 1 Step B. After work up and chromatography of the reaction mixture (silica, ethyl acetate/methanol/35% ammonia solution=50/50/1) 14-O-{[(1R,2R,5S)-5-amino-2-hydroxy-cyclohexylsulfanyl]-acetyl}-mutilin+(1S,2S,5R) diastereomer (a) ($R_f$=0.33, 524 mg, 56% yield) and 14-O-{[(1R,2R,4S)-4-amino-2-hydroxy-cyclohexylsulfanyl]-acetyl}-mutilin+(1S,2S,4R) diastereomer (b) ($R_f$=0.22, 160 mg, 17%) were obtained as colorless amorphous foams.

(a): $^1$H NMR (400 MHz, DMSO-$d_6$, δ, ppm, inter alia): 6.13 (dd, 1H, 19-H, J=11 Hz and 18 Hz), 5.53 (d, 1H, 14-H, J=8 Hz), 5.05 (m, 2H, 20-H), 4.51 (d, 1H, 11-OH, J=6 Hz), 3.48 (m, 1H, 2'-H), 3.42 (m, 1H, 11-H), AB-system ($v_A$=3.37, $v_B$=3.23, 22-H, J=19 Hz), 2.98 (m, 1H, 1'-H), 2.82 (m, 1H, 5'-H), 2.40 (bs, 1H, 4-H), 1.36 (s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=7 Hz).

(b): $^1$H NMR (400 MHz, DMSO-$d_6$, δ, ppm, inter alia): 6.14 (dd, 1H, 19-H, J=11 Hz and 18 Hz), 5.54 (d, 1H, 14-H, J=8 Hz), 5.06 (m, 2H, 20-H), 4.51 (bs, 1H, 11-OH), 3.79 (m, 1H, 2'-H), 3.42 (m, 1H, 11-H), AB-system ($v_A$=3.33, $v_B$=3.23, 22-H, J=15 Hz), 3.04 (m, 1H, 4'-H), 2.82 (m, 1H, 1'-H), 2.40 (bs, 1H, 4-H), 1.37 (s, 3H, 15-CH$_3$), 1.06 (s, 3H, 18-CH$_3$), 0.81 (d, 3H, 17-CH$_3$, J=7 Hz), 0.63 (d, 3H, 16-CH$_3$, J=7 Hz).

Step B. 14-O-{[(1R,2R,5S)-5-Amino-2-hydroxy-cyclohexylsulfanyl]-acetyl}-mutilin hydrochloride+(1S,2S,5R) Diastereomer Hydrochloride 14-O-{[(1R,2R,5S)-5-Amino-2-hydroxy-cyclohexylsulfanyl]-acetyl}-mutilin+(1S,2S,5R) diastereomer (516 mg, 1.02 mmol) was treated according to the method of Example 1 Step C to obtain 14-O-{[(1R,2R,5S)-5-amino-2-hydroxy-cyclohexylsulfanyl]-acetyl}-mutilin hydrochloride+(1S,2S,5R) diastereomer hydrochloride (533 mg, 96% yield) as colorless amorphous solid.

$^1$H NMR (500 MHz, DMSO-$d_6$, δ, ppm, inter alia): 7.7 (bs, 3H, NH$_3$$^+$), 6.13, 6.12 (2dd, 1H, 19-H, J=11 Hz and 18 Hz), 5.55 (d, 1H, 14-H, J=8 Hz), 5.05 (m, 2H, 20-H), 4.53 (d, 1H, 11-OH, J=6 Hz), 3.70 (m, 1H, 2'-H), 3.42 (t, 1H, 11-H, J=6 Hz), 3.35 (m, 2H, 22-H), 3.09 (m, 2H, 1'-H, 5'-H), 2.40 (bs, 1H, 4-H), 1.35 (s, 3H, 15-CH$_3$), 1.05 (s, 3H, 18-CH$_3$), 0.82 (d, 3H, 17-CH$_3$, J=7 Hz), 0.63 (d, 3H, 16-CH$_3$, J=7 Hz). MS-ESI (m/z): 508 (MH$^+$), 530 (MNa$^+$), 1015 (2 MH$^+$), 1037 (2MNa$^+$), 542 (MCl$^-$).

Example 2A

14-O-{[(1R,2R,5S)-5-Amino-2-hydroxy-cyclohexylsulfanyl]-acetyl}-mutilin and 14-O-{[(1S,2S,5R)-5-Amino-2-hydroxy-cyclohexylsulfanyl]-acetyl}-mutilin The mixture of 14-O-{[(1R,2R,5S)-5-Amino-2-hydroxy-cyclohexylsulfanyl]-acetyl}-mutilin+(1S,2S,5R) diastereomer (4.91 g, 9.67 mmol) from Example 2 Step A was separated on a chiral column (250×20 mm CHIRALCEL OD-H, n-heptane/isopropanol/diethylamine=80/20/0.1) to yield 14-O-{[(1R*,2R*, 5S*)-5-amino-2-hydroxy-cyclohexylsulfanyl]-acetyl}-mutilin (a) (early eluting compound, 2.07 g, 42% yield, uncorrected) and 14-O-{[(1S*,2S*, 5R*)-5-amino-2-hydroxy-cyclohexylsulfanyl]-acetyl}-mutilin (b) (late eluting compound, 2.36 g, 48% yield, uncorrected) as colorless amorphous foams.

(a): $^1$H NMR (400 MHz, DMSO-$d_6$, δ, ppm, inter alia): 6.13 (dd, 1H, 19-H, J=11 Hz and 18 Hz), 5.53 (d, 1H, 14-H, J=8 Hz), 5.05 (m, 2H, 20-H), 4.72 (d, 1H, 2'-OH, J=4 Hz), 4.50 (d, 1H, 11-OH, J=6 Hz), 3.47 (m, 1H, 2'-H), 3.45-3.20 (m, 3H, 11-H, 22-H), 2.98 (m, 1H, 1'-H), 2.80 (m, 1H, 5'-H), 2.40 (bs, 1H, 4-H), 1.36 (s, 3H, 15-CH$_3$), 1.06 (s, 3H, 18-CH$_3$), 0.81 (d, 3H, 17-CH$_3$, J=7 Hz), 0.63 (d, 3H, 16-CH$_3$, J=7 Hz). MS-ESI (m/z): 508 (MH$^+$), 530 (MNa$^+$), 1015 (2 MH$^+$), 1037 (2MNa$^+$), 506 (M-H)$^-$, 542 (MCl$^-$).

(b): $^1$H NMR (400 MHz, DMSO-$d_6$, δ, ppm, inter alia): 6.13 (dd, 1H, 19-H, J=11 Hz and 18 Hz), 5.53 (d, 1H, 14-H, J=8 Hz), 5.05 (m, 2H, 20-H), 4.72 (d, 1H, 2'-OH, J=4 Hz), 4.50 (d, 1H, 11-OH, J=6 Hz), 3.47 (m, 1H, 2'-H), 3.45-3.20 (m, 3H, 11-H, 22-H), 2.98 (m, 1H, 1'-H), 2.80 (m, 1H, 5'-H), 2.40 (bs, 1H, 4-H), 1.36 (s, 3H, 15-CH$_3$), 1.06 (s, 3H, 18-CH$_3$), 0.81 (d, 3H, 17-CH$_3$, J=7 Hz), 0.63 (d, 3H, 16-CH$_3$, J=7 Hz). MS-ESI (m/z): 508 (MH$^+$), 530 (MNa$^+$), 1015 (2 MH$^+$), 1037 (2MNa$^+$), 506 (M-H)$^-$, 542 (MCl$^-$).

Example 3

14-O-{[(1R,2R,4S)-4-Amino-2-hydroxy-cyclohexylsulfanyl]-acetyl}-mutilin hydrochloride+(1S,2S,4R) Diastereomer Hydrochloride 14-O-{[(1R,2R,4S)-4-Amino-2-hydroxy-cyclohexylsulfanyl]-acetyl}-mutilin+(1S,2S,4R) diastereomer (152 mg, 0.30 mmol) from Example 2 Step A was treated according to the method of Example 1 Step C to obtain 14-O-{[(1R,2R,4S)-4-amino-2-hydroxy-cyclohexylsulfanyl]-acetyl}-mutilin hydrochloride+(1S,2S,4R) diastereomer hydrochloride (148 mg, 91% yield) as colorless amorphous solid.

$^1$H NMR (500 MHz, DMSO-$d_6$, δ, ppm, inter alia): 7.8 (bs, 3H, NH$_3$$^+$), 6.14, 6.13 (2dd, 1H, 19-H, J=11 Hz and 18 Hz), 5.55 (d, 1H, 14-H, J=8 Hz), 5.20 (d, 1H, 2'-OH), 5.05 (m, 2H, 20-H), 4.53 (d, 1H, 11-OH, J=6 Hz), 3.88 (m, 1H, 2'-H), 3.42 (t, 1H, 11-H, J=6 Hz), 3.32 (m, 2H, 22-H), 3.22 (m, 1H, 4'-H), 2.92 (m, 1H, 1'-H), 2.40 (bs, 1H, 4-H), 1.35 (s, 3H, 15-CH$_3$), 1.05 (s, 3H, 18-CH$_3$), 0.81 (d, 3H, 17-CH$_3$, J=7 Hz), 0.63 (d, 3H, 16-CH$_3$, J=7 Hz). MS-ESI (m/z): 508 (MH$^+$), 530 (MNa$^+$), 1015 (2 MH$^+$), 1037 (2MNa$^+$), 542 (MCl$^-$).

Example 4

14-O-{1-[(1R,2R,5R)-5-Amino-2-hydroxy-cyclohexylsulfanyl]-acetyl}-mutilin+(1S,2S,5S) Diastereomer

Step A. tert-Butyl-dimethyl-(cis-3,4-epoxycyclohexyloxy)-silane

To a solution of 3-cyclohexen-1-ol (Amburgey, J. C.; Shuey, S. W.; Pedersen, I., (G., Hiskey R., *Bioorganic Chem-*

*istry* 1994, 22, 172-197.) (10 g, 102 mmol) in 200 ml of dichloromethane was added vanadyl acetylacetonate (0.5 g, cat.) and tert-butyl hydroperoxide (20.4 ml 5.5M in decane, 112 mmol) and stirred overnight at room temperature. The resulting reaction mixture was treated with tert-butyldimethylsilyl chloride (16.9 g, 112 mmol), imidazole (9.02 g, 132 mmol) and 4-dimethylaminopyridine (2.49 g, 20 mmol) at 4° C. and stirred for 5 hours at room temperature. The reaction mixture was diluted with dichloromethane and subsequently extracted with 10% $NaHSO_3$ solution, saturated $NaHCO_3$ solution and brine. The organic layer was dried over sodium sulfate and filtered. The filtrate was concentrated under reduced pressure and subjected to chromatography (silica, cyclohexane/ethyl acetate=15/1) to yield tert-butyl-dimethyl-(cis-3,4-epoxycyclohexyloxy)-silane ($R_f$=0.35, 18.3 g, 79% yield) as colorless oil.

$^1$H NMR (500 MHz, DMSO-$d_6$, δ, ppm): 3.55 (m, 1H), 3.00 (m, 2H), 2.15 (m, 1H), 2.00 (m, 1H), 1.80 (m, 1H), 1.50 (m, 1H), 1.35 (m, 1H), 1.35 (m, 1H), 1.25 (m, 1H), 0.83 (s, 9H, tert-butyl), 0.0 (s, 9H, Si(CH$_3$)$_2$).

Step B. 14-O-{[(1R,2R,5S)-5-(tert-Butyl-dimethyl-silyloxy)-2-hydroxy-cyclohexylsulfanyl]-acetyl}-mutilin+(1S,2S,5R) Diastereomer tert-Butyl-dimethyl-(cis-3,4-epoxycyclohexyloxy)-silane (6.41 g, 28 mmol) was treated with pleuromutilin thiol according to the method of Example 1 Step A2. Crude 14-O-{[(1R,2R,5S)-5-(tert-butyl-dimethyl-silyloxy)-2-hydroxy-cyclohexylsulfanyl]acetyl}-mutilin+(1S,2S,5R) diastereomer was obtained as colorless amorphous foam which was directly used for the next step.

$^1$H NMR (400 MHz, DMSO-$d_6$, δ, ppm, inter alia): 6.13 (dd, 1H, 19-H, J=11 Hz and 18 Hz), 5.52 (d, 1H, 14-H, J=8 Hz), 5.05 (m, 2H, 20-H), 4.78 (dd, 1H, 2'-OH, J=5 Hz and 6 Hz), 4.48 (d, 1H, 11-OH, J=6 Hz), 3.88 (m, 1H, 5'-H), 3.15-3.45 (m, 4H, 2'-H, 11-H, 22-CH$_2$), 2.92 (m, 1H, 1'-H), 2.38 (bs, 1H, 4-H), 1.36 (s, 3H, 15-CH$_3$), 1.05 (s, 3H, 18-CH$_3$), 0.86 (s, 9H, tert-butyl), 0.81 (d, 3H, 17-CH$_3$, J=7 Hz), 0.63 (d, 3H, 16-CH$_3$, J=7 Hz), 0.0 (s, 6H, Si(CH$_3$)$_2$).

Step C. 14-O-{[(1R,2R,5S)-2,5-Dihydroxy-cyclohexylsulfanyl]-acetyl}-mutilin+(1S,2S,5R) Diastereomer To a solution of 14-O-{[(1R,2R,5S)-5-(tert-butyl-dimethyl-silyloxy)-2-hydroxy-cyclohexylsulfanyl]-acetyl}-mutilin+(1S,2S,5R) diastereomer (9.46 g, 15.1 mmol) in 25 ml of tetrahydrofuran a mixture of acetic acid and water (3:1, 100 ml) was added and stirred for 2 days at 40° C. The reaction mixture was concentrated nearly to dryness under reduced pressure and the residue was dissolved in ethyl acetate and submitted to chromatography (silica, cyclohexane/ethyl acetate=1/3) to yield the 14-O-{[(1R,2R,5S)-2,5-dihydroxy-cyclohexylsulfanyl]-acetyl}-mutilin+(1S,2S,5R) diastereomer ($R_f$=0.27, 7.07 g, 92% yield) as colorless amorphous foam.

$^1$H NMR (400 MHz, DMSO-$d_6$, δ, ppm, inter alia): 6.12 (dd, 1H, 19-H, J=11 Hz and 18 Hz), 5.53 (d, 1H, 14-H, J=8 Hz), 5.05 (m, 2H, 20-H), 4.72 (dd, 1H, 2'-OH, J=2 Hz and 5 Hz), 4.48 (d, 1H, 11-OH, J=6 Hz), 4.43 (t, 1H, 5'-OH), 3.68 (m, 1H, 5'-H), 3.45-3.20 (m, 4H, 2'-H, 1-H, 22-H), 2.94 (m, 1H, 1'-H), 2.38 (bs, 1H, 4-H), 1.36 (s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=7 Hz). MS-ESI (m/z): 531 (MNa$^+$), 1039 (2MNa$^+$).

Step D. 14-O-{1-[(1R,2R,5S)-2-Hydroxy-5-methanesulfonyloxy-cyclohexylsulfanyl]-acetyl}-mutilin+(1S,2S,5R) Diastereomer To a solution of 14-O-{[(1R,2R,5S)-2,5-dihydroxy-cyclohexylsulfanyl]-acetyl}-mutilin+(1S,2S,5R) diastereomer (6.07 g, 11.9 mmol) in 36 ml of pyridine was added methanesulfonyl chloride (1.1 ml, 14.3 mmol) and the resulting mixture was stirred overnight at room temperature. Subsequently the solvent was evaporated under reduced pressure; the residue was diluted with 1N HCl and extracted three times with ethyl acetate. The combined organic layers were washed with brine, dried over sodium sulfate and filtered. The filtrate was concentrated and purified by column chromatography (silica, cyclohexane/ethyl acetate=1/1) to yield 14-O-{[(1R,2R,5S)-2-hydroxy-5-methanesulfonyloxy-cyclohexylsulfanyl]-acetyl}-mutilin+(1S,2S,5R) diastereomer ($R_f$=0.15, 2.55 g, 36% yield) as colorless amorphous foam.

$^1$H NMR (400 MHz, DMSO-$d_6$, δ, ppm, inter alia): 6.12 (dd, 1H, 19-H, J=11 Hz and 18 Hz), 5.54 (d, 1H, 14-H, J=8 Hz), 5.07 (m, 2H, 20-H), 5.00 (t, 1H, 2'-OH, J=5 Hz), 4.78 (m, 1H, 5'-H), 4.50 (d, 1H, 11-OH, J=6 Hz), 3.55-3.25 (m, 4H, 2'-H, 11-H, 22-H), 2.91 (m, 1H, 1'-H), 2.38 (bs, 1H, 4-H), 1.36 (s, 3H, 15-CH$_3$), 1.05 (s, 3H, 18-CH$_3$), 0.80 (d, 3H, 17-CH$_3$, J=7 Hz), 0.63 (d, 3H, 16-CH$_3$, J=7 Hz).

Step E. 14-O-{[(1R,2R,5R)-5-Azido-2-hydroxy-5-methanesulfonyloxy-cyclohexylsulfanyl]-acetyl}-mutilin+(1S,2S,5S) Diastereomer A solution of 14-O-{[(1R,2R,5S)-2-hydroxy-5-methanesulfonyloxy-cyclohexylsulfanyl]-acetyl}-mutilin+(1S,2S,5R) diastereomer (2.55 g, 4.35 mmol) and sodium azide (0.85 g, 13 mmol) in 30 ml of dimethylformamide was heated for 6 hours at 80° C. The reaction mixture was diluted with water and brine and extracted three times with ethyl acetate. The combined organic layers were washed with water and brine, dried over sodium sulfate and filtered. The solvent was removed under reduced pressure and crude 14-O-{[(1R,2R,5R)-5-azido-2-hydroxy-cyclohexylsulfanyl]-acetyl}-mutilin+(1S,2S,5S) diastereomer (quantitative yield, cyclohexane/ethyl acetate=1/1, $R_f$=0.35) was obtained as amorphous foam which was directly used for the next step.

$^1$H NMR (400 MHz, DMSO-$d_6$, δ, ppm, inter alia): 6.15, 6.13 (2dd, 1H, 19-H, J=11 Hz and 18 Hz), 5.56, 5.54 (2d, 1H, 14-H, J=8 Hz), 5.05 (m, 2H, 20-H), 4.90 (d, 1H, 2'-OH, J=5 Hz), 4.50, 4.49 (2d, 1H, 11-OH, J=6 Hz), 3.50-3.25 (m, 5H, 2'-H, 5'-H, 11-H, 22-H), 2.64 (m, 1H, 1'-H), 2.40 (bs, 1H, 4-H), 1.36 (s, 3H, 15-CH$_3$), 1.06 (s, 3H, 18-CH$_3$), 0.81 (d, 3H, 17-CH$_3$, J=7 Hz), 0.63 (d, 3H, 16-CH$_3$, J=7 Hz).

Step F. 14-O-{[(1R,2R,5R)-5-Amino-2-hydroxy-cyclohexylsulfanyl]-acetyl}-mutilin+(1S,2S,5S) Diastereomer Triphenylphosphine (1.18 g, 4.50 mmol) was added to a solution of 14-O-{[(1R,2R,5R)-5-azido-2-hydroxy-cyclohexylsulfanyl]-acetyl}-mutilin+(1S,2S,5S) diastereomer (2.4 g, 4.50 mmol) in 30 ml of tetrahydrofuran and stirred overnight at room temperature. Subsequently water (approx. 3 ml) was added and the reaction mixture was heated for 1 hour at reflux. After evaporation of the solvent the residue was diluted with water and brine and extracted three times with ethyl acetate. The combined organic layers were dried over sodium sulfate, filtered and subjected to chromatography (silica, ethyl acetate/methanol/35% ammonia solution=100/100/1) to yield 14-O-{[(1R,2R,5R)-5-amino-2-hydroxy-cyclohexylsulfanyl]-acetyl}-mutilin+(1S,2S,5S) diastereomer (R$_f$=0.3, 1.74 g, 79% yield) as colorless amorphous foam.

$^1$H NMR (400 MHz, DMSO-d$_6$, δ, ppm, inter alia): 7.25, 6.65 (2bs, 1H, NH), 6.14 (dd, 1H, 19-H, J=11 Hz and 18 Hz), 5.54 (d, 1H, 14-H, J=8 Hz), 5.04 (m, 2H, 20-H), 4.50 (bs, 1H, 11-OH), 3.55-3.10 (m, 5H, 2'-H, 5'-H, 11-H, 22-H), 2.58 (m, 1H, 1'-H), 2.40 (bs, 1H, 4-H), 1.36 (s, 3H, 15-CH$_3$), 1.05 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 508 (MH$^+$), 530 (MNa$^+$), 1037 (2MNa$^+$).

Example 4A

14-O-{[(1R,2R,5R)-5-Amino-2-hydroxy-cyclohexylsulfanyl]-acetyl}-mutilin and 14-O-{[(1S,2S,5S)-5-Amino-2-hydroxy-cyclohexylsulfanyl]-acetyl}-mutilin The mixture of 14-O-{[(1R,2R,5R)-5-Amino-2-hydroxy-cyclohexylsulfanyl]-acetyl}-mutilin+(1S,2S,5S) diastereomer (4 g, 7.87 mmol) from Example 4 Step F was separated on a chiral column (250×20 mm CHIRALPAK IC, n-heptane/tetrahydrofuran/diethylamine=70/30/0.1) to yield 14-O-{[(1S*, 2S*,5S*)-5-amino-2-hydroxy-cyclohexylsulfanyl]-acetyl}-mutilin (late eluting compound, 1.1 g, 28% yield, uncorrected) as colorless amorphous foam.

$^1$H NMR (400 MHz, DMSO-d$_6$, δ, ppm, inter alia): 6.13 (dd, 1H, 19-H, J=11 Hz and 18 Hz), 5.54 (d, 1H, 14-H, J=8 Hz), 5.06 (m, 2H, 20-H), 5.76 (d, 1H, 2'-OH, J=7 Hz), 4.50 (d, 1H, 11-OH, J=7 Hz), 3.55-3.15 (m, 5H, 2'-H, 11-H, 5'-H, 22-H), 2.48 (m, 1H, 1'-H), 2.40 (bs, 1H, 4-H), 1.36 (s, 3H, 15-CH$_3$), 1.05 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 508 (MH$^+$), 1037 (2MNa$^+$), 506 (M-H)$^-$, 542 (MCl$^-$).

Example 5

14-O-{1-[(1R,2R,3R)-3-Amino-2-hydroxy-cyclohexylsulfanyl]-acetyl}-mutilin hydrochloride+(1S,2S,3S) Diastereomer Hydrochloride Step A. 14-O-{[(1R,2R,3R)-3-tert-Butoxycarbonylamino-2-hydroxy-cyclohexylsulfanyl]-acetyl}-mutilin+(1S,2S,3S) Diastereomer (cis)-2,3-Epoxycyclohexyl-carbamic acid tert-butyl ester (O'Brien, P.; Childs, A., C.; Ensor, G. *Organic Letters* 2003, 5(26), 4955-4957.) (1 g, 4.69 mmol) was treated with pleuromutilin thiol according to the method of Example 1 Step A1. After work up and chromatography of the reaction mixture (silica, cyclohexane/ethyl acetate=1/1) 14-O-{[(1R,2R,3R)-3-tert-butoxycarbonylamino-2-hydroxy-cyclohexylsulfanyl]-acetyl}-mutilin+(1S,2S,3S) diastereomer (R$_f$=0.5, 1.32 g, 46%) was obtained as colorless amorphous foam.

$^1$H NMR (400 MHz, DMSO-d$_6$, δ, ppm, inter alia): 6.12 (m, 2H, NH, 19-Hz), 5.54 (d, 1H, 14-H, J=8 Hz), 5.05 (m, 2H, 20-H), 4.96 (d, 1H, 2'-OH, J=4 Hz), 4.50, 4.99 (2d, 1H, 11-OH, J=6 Hz)), 3.65 (m, 1H, 2'-H), 3.57 (m, 1H, 3'-H), 3.42 (t, 1H, 11-H, J=6 Hz), AB-system (ν$_A$=3.30, 3.29, ν$_B$=3.23, 3.22, 22-H, J=15 Hz), 3.06 (m, 1H, 1'-H), 2.40 (bs, 1H, 4-H), 1.36 (s, 12H, tert-butyl, 15-CH$_3$), 1.05 (s, 3H, 18-CH$_3$), 0.82 (d, 3H, 17-CH$_3$, J=7 Hz), 0.63 (d, 3H, 16-CH$_3$, J=6 Hz).

Step B. 14-O-{[(1R,2R,3R)-3-Amino-2-hydroxy-cyclohexylsulfanyl]-acetyl}-mutilin+(1S,2S,3S) Diastereomer 14-O-{[(1R,2R,3R)-3-tert-Butoxycarbonylamino-2-hydroxy-cyclohexylsulfanyl]-acetyl}-mutilin+(1S,2S,3S) diastereomer (400 mg, 0.658 mmol) was treated according to the method of Example 1 Step B. After work up and chromatography of the reaction mixture (silica, ethyl acetate/methanol=1/5) 14-O-{[(1R,2R,3R)-3-amino-2-hydroxy-cyclohexylsulfanyl]-acetyl}-mutilin+(1S,2S,3S) diastereomer (R$_f$=0.1, 249 mg, 75%) was obtained as colorless amorphous foam.

MS-ESI (m/z): 508 (MH$^+$), 530 (MNa$^+$), 1015 (2 MH$^+$), 1037 (2MNa$^+$).

Step C. 14-O-{[(1R,2R,3R)-3-Amino-2-hydroxycyclohexylsulfanyl]-acetyl}-mutilin hydrochloride+(1S,2S,4S) Diastereomer Hydrochloride 14-O-{[(1R,2R,3R)-3-Amino-2-hydroxy-cyclohexylsulfanyl]-acetyl}-mutilin+(1S,2S,3S) diastereomer (249 mg, 0.49 mmol) was treated according to the method of Example 1 Step C to obtain 14-O-{[(1R,2R,3R)-3-amino-2-hydroxy-cyclohexylsulfanyl]-acetyl}-mutilin hydrochloride+(1S,2S,3S) diastereomer hydrochloride (247 mg, 93% yield) as colorless amorphous solid.

$^1$H NMR (400 MHz, DMSO-d$_6$, δ, ppm, inter alia): 7.8 (bs, 3H, NH$_3^+$), 6.13 (d, 2H, 19-Hz, J=11 Hz and 18 Hz), 5.80 (d, 1H, 2'-OH, J=4 Hz), 5.55 (d, 1H, 14-H, J=8 Hz), 5.05 (m, 2H, 20-H), 4.55, 4.54 (2d, 1H, 11-OH, J=6 Hz)), 3.87 (m, 1H, 2'-H), 3.42 (t, 1H, 1-H, J=6 Hz), AB-system (ν$_A$=3.35, ν$_B$=3.24, 22-H, J=15 Hz), 3.20, 3.13 (2m, 1H, 3'-H, 1'-H), 2.40 (bs, 1H, 4-H), 1.36 (s, 3H, 15-CH$_3$), 1.05 (s, 3H, 18-CH$_3$), 0.81 (d, 3H, 17-CH$_3$, J=7 Hz), 0.63 (d, 3H, 16-CH$_3$, J=7 Hz). MS-ESI (m/z): 508 (MH$^+$), 1015 (2 MH$^+$), 542 (MCl$^-$).

Example 6

14-O-{[(1R,2R,4R)-4-Diethylamino-2-hydroxy-cyclohexylsulfanyl]-acetyl}-mutilin+(1S,2S,4S) Diastereomer and 14-O-{[(1R,2R,4R)-4-Ethylamino-2-hydroxy-cyclohexylsulfanyl]-acetyl}-mutilin+(1S,2S,4S) Diastereomer To a solution of 14-O-{[(1R,2R,4R)-4-amino-2-hydroxy-cyclohexylsulfanyl]-acetyl}-mutilin+(1S,2S,4S) diastereomer (900 mg, 1.77 mmol) from Example 1 Step B in 10 ml dichloromethane was added acetaldehyde (2.77 ml, IM in dichloromethane) and acetic acid (77 µl, 1.77 mmol) and stirred for 30 minutes at room temperature. The resulting reaction mixture was treated with sodium triacetoxyborohydride (750 mg, 3.54 mmol) and stirred overnight at room temperature, diluted with dichloromethane and subsequently extracted with NaHCO$_3$ solution and brine. The organic layer was dried over sodium sulfate and filtered. The filtrate was subjected to chromatography (silica, ethyl acetate/methanol/35% ammonia solution=50/50/1) to yield 14-O-{[(1R,2R,4R)-4-diethylamino-2-hydroxy-cyclohexylsulfanyl]-acetyl}-mutilin+(1S,2S,4S) diastereomer (a) (92 mg, 9% yield) and 14-O-{[(1R,2R,4R)-4-ethylamino-2-hydroxy-cyclohexylsulfanyl]-acetyl}-mutilin+(1S,2S,4S) diastereomer (b) (163 mg, 17% yield) as colorless amorphous foams.

(a): $^1$H NMR (400 MHz, DMSO-d$_6$, δ, ppm, inter alia): 6.14 (dd, 1H, 19-H, J=11 Hz and 18 Hz), 5.55 (d, 1H, 14-H, J=8 Hz), 5.05 (m, 2H, 20-H), 4.83 (d, 1H, 2'-OH, J=4 Hz), 4.47 (d, 1H, 11-OH, J=6 Hz), 3.42 (m, 1H, 11-H), AB-system (ν$_A$=3.50, 3.42, ν$_B$=3.30, 3.27, 22-H, J=15 Hz), 3.25 (m, 1H, 2'-H), 2.50 (m, 2H, 1'-H, 4'-H), 2.40 (m, 5H, NCH$_2$, 4-H), 1.36 (s, 3H, 15-CH$_3$), 1.05 (s, 3H, 18-CH$_3$), 0.92 (t, 6H, NCH$_2$CH$_3$, J=7 Hz), 0.81 (d, 3H, 17-CH$_3$, J=7 Hz), 0.63 (d, 3H, 16-CH$_3$, J=7 Hz). MS-ESI (m/z): 564 (MH$^+$), 586 (MNa$^+$), 562 (M-H)$^-$.

(b): $^1$H NMR (400 MHz, DMSO-d$_6$, δ, ppm, inter alia): 6.13 (dd, 1H, 19-H, J=11 Hz and 18 Hz), 5.54 (d, 1H, 14-H, J=8 Hz), 5.05 (m, 2H, 20-H), 4.48 (d, 1H, 11-OH, J=6 Hz), 3.42 (m, 1H, 11-H), AB-system (ν$_A$=3.48, ν$_B$=3.25, 22-H, J=15 Hz), 2.55 (m, 2H, 1'-H, 4'-H), 2.40 (bs, 1H, 4-H), 1.35 (s, 3H, 15-CH$_3$), 1.05 (s, 3H, 18-CH$_3$), 0.95 (t, 3H, NCH$_2$CH$_3$, J=7 Hz), 0.81 (d, 3H, 17-CH$_3$, J=7 Hz), 0.63 (d, 3H, 16-CH$_3$, J=6 Hz). MS-ESI (m/z): 536 (MH$^+$), 558 (MNa$^+$), 534 (M-H)$^-$.

Example 7

14-O-{[(1R,2R,5S)-5-Ethylamino-2-hydroxy-cyclohexylsulfanyl]-acetyl}-mutilin hydrochloride+(1S, 2S,5R) Diastereomer Hydrochloride Step A. N-Ethyl-N-(cyclohex-3-enyl)-carbamic acid tert-butyl ester To a solution of cyclohex-3-enyl-carbamic acid tert-butyl ester (Kampferer, P.; Vasella, A. *Helvetica Chimica Acta* 2004, 87, 2764-2789) (4.34 g, 22 mmol) in 20 ml of DMSO was added sodium hydride (880 mg, 60% dispersion, 22 mmol) and after one hour of stirring ethyl iodide (1.78 ml, 22 mmol). After further stirring for 2 hours at room temperature the reaction mixture was concentrated under reduced pressure. The residue was diluted with water and brine and extracted three times with ethyl acetate. The organic layers were dried over sodium sulfate and filtered. The filtrate was concentrated under reduced pressure and after chromatography (silica, cyclohexane/ethyl acetate=12/1) the title compound (R$_f$=0.30, 2.88 g, 58% yield) was obtained as colorless solid.

$^1$H NMR (400 MHz, CDCl$_3$, δ, ppm): 5.61 (m, 2H, double bond), 4.08 (bs, 1H, NCH), 3.15 (m, 2H, NCH$_2$), 2.15, 1.75 (2m, 6H), 1.47 (s, 9H, tert-butyl), 1.13 (t, 3H, NCH$_2$CH$_3$, J=7 Hz).

Step B. N-ethyl-N-(cis-3,4-epoxycyclohexyl)-carbamic acid tert-butyl ester

N-Ethyl-N-(cyclohex-3-enyl)-carbamic acid tert-butyl ester (2.87 g, 12.7 mmol) was dissolved in 75 ml of dichloromethane and treated with 3-chloroperbenzoic acid (4.50 g, 70%, 19 mmol). After stirring at room temperature for 20 hours the reaction mixture was concentrated under reduced pressure. The residue was diluted with ethyl acetate and subsequently extracted with 10% NaHSO$_3$ solution, saturated NaHCO$_3$ solution and brine. The organic layer was dried over sodium sulfate and filtered. The filtrate was concentrated under reduced pressure and after chromatography (silica, cyclohexane/dioxane=5/1) the title compound (R$_f$=0.2, 1.50 g, 49% yield) was obtained.

$^1$H NMR (400 MHz, CDCl$_3$, δ, ppm): 4.0 (bs, 1H, NCH), 3.14 (m, 2H, NCH$_2$), 3.06 (bs, 2H, epoxide), 2.13, 2.08, 1.88, 1.60, 1.36 (4m, 6H), 1.47 (s, 9H, tert-butyl), 0.08 (t, 3H, NCH$_2$CH$_3$).

Step C. 14-O-{[(1R,2R,5S)-5-(tert-Butoxycarbonyl-ethyl-amino)-2-hydroxy-cyclohexylsulfanyl]-acetyl}-mutilin+(1S,2S,5R) Diastereomer N-Ethyl-N-(cis-3,4-epoxycyclohexyl)-carbamic acid tert-butyl ester (1.5 g, 6.2 mmol) was treated with pleuromutilin thiol according to the method of Example 1 Step A1. After work up and chromatography of the reaction mixture (silica, cyclohexane/dioxane=3/1) 14-O-{[(1R,2R,5S)-5-(tert-butoxycarbonyl-ethyl-amino)-2-hydroxy-cyclohexylsulfanyl]-acetyl}-mutilin+(1S,2S,5R) diastereomer (R$_f$=0.4, 2.57 g, 65% yield) was obtained as colorless amorphous foam.

MS-ESI (m/z): 536 (MH$^+$), 558 (MNa$^+$), 534 (M-H)$^-$.

Step D. 14-O-{[(1R,2R,5S)-5-Ethylamino-2-hydroxy-cyclohexylsulfanyl]-acetyl}-mutilin+(1S,2S, 5R) Diastereomer 14-O-{[(1R,2R,5S)-5-(tert-Butoxycarbonyl-ethyl-amino)-2-hydroxy-cyclohexylsulfanyl]-acetyl}-mutilin+ (1S,2S,5R) diastereomer (2.57 g, 4.04 mmol) was treated according to the method of Example 1 Step B. After work up and chromatography of the reaction mixture (silica, ethyl acetate/methanol/35% ammonia solution=100/100/1) 14-O-{[(1R,2R,5S)-5-ethylamino-2-hydroxy-cyclohexylsulfanyl]-acetyl}-mutilin+(1S,2S,5R) diastereomer (R$_f$=0.3, 1.08 g, 50%) was obtained as colorless amorphous foam.

$^1$H NMR (500 MHz, CDCl$_3$, δ, ppm, inter alia): 6.48 (dd, 1H, 19-H, J=10 Hz and 18 Hz), 5.77 (m, 1H, 14-H), 5.36 (m, 1H, 20-H), 5.22 (d, 1H, 20-H, J=17 Hz), 3.45 (d, 1H, 2'-H), 3.37 (d, 1H, 11-H, J=6 Hz), 3.25 (m, 1H, 22-H), 2.97 (m, 1H, 1'-H), 2.91 (m, 1H, 5'-H), 2.63 (q, 2H, NCH$_2$, J=7 Hz), 2.10 (bs, 1H, 4-H), 1.46 (s, 3H, 15-CH$_3$), 1.18 (s, 3H, 18-CH$_3$), 1.12 (t, 3H, NCH$_2$CH$_3$, J=7 Hz), 0.98 (d, 3H, 17-CH$_3$, J=7 Hz), 0.73 (d, 3H, 16-CH$_3$, J=7 Hz).

Step E. 14-O-{[(1R,2R,5S)-5-Ethylamino-2-hydroxy-cyclohexylsulfanyl]-acetyl}-mutilin hydrochloride+(1S,2S,5R) Diastereomer Hydrochloride 14-O-{[(1R,2R,5S)-5-Ethylamino-2-hydroxy-cyclohexylsulfanyl]-acetyl}-mutilin+(1S,2S,5R) diastereomer (86 mg, 0.16 mmol) was treated according to the method of Example 1 Step C to obtain 14-O-{[(1R,2R,5S)-5-ethylamino-2-hydroxy-cyclohexylsulfanyl]-acetyl}-mutilin hydrochloride+ (1S,2S,5R) diastereomer hydrochloride (83 mg, 90% yield) as colorless amorphous solid.

$^1$H NMR (400 MHz, CDCl$_3$, δ, ppm, inter alia): 9.3 (bs, 2H, NH$_2$$^+$), 6.45 (m, 1H, 19-H), 5.73 (d, 1H, 14-H, J=10 Hz), 5.35 (m, 1H, 20-H), 5.22 (d, 1H, 22-H, J=18H), 3.85 (m, 1H, 2'-H), 3.33 (m, 3H, 1-H, 22-H), 3.07 (m, 2H, NCH$_2$), 2.10 (bs, 1H, 4-H), 1.50 (t, 3H, NCH$_2$CH$_3$, J=7 Hz), 1.45 (s, 3H, 15-CH$_3$), 1.18 (s, 3H, 18-CH$_3$), 0.90 (d, 3H, 17-CH$_3$, J=7 Hz), 0.73 (d, 3H, 16-CH$_3$, J=7 Hz). MS-ESI (m/z): 536 (MH$^+$), 570 (MCl$^-$).

Example 8

14-O-{[(1R,2R,5S)-5-Diethylamino-2-hydroxy-cyclohexylsulfanyl]-acetyl}-mutilin hydrochloride+ (1S,2S,5R) Diastereomer Hydrochloride Step A. 14-O-{[(1R,2R,5S)-5-Diethylamino-2-hydroxy-cyclohexylsulfanyl]-acetyl}-mutilin+(1S,2S, 5R) Diastereomer 14-O-{[(1R,2R,5S)-5-Ethylamino-2-hydroxy-cyclohexylsulfanyl]-acetyl}-mutilin+(1S,2S,5R) diastereomer (250 mg, 0.47 mmol) from Example 7 Step D was treated with acetaldehyde (53 μl, 0.93 mmol) according to the method of Example 6. After work up and chromatography of the reaction mixture (silica, ethyl acetate/methanol=1/1) 14-O-{[(1R, 2R,5S)-5-diethylamino-2-hydroxy-cyclohexylsulfanyl]- acetyl}-mutilin+(1S,2S,5R) diastereomer ($R_f$=0.2, 230 mg, 87%) was obtained as colorless amorphous foam.

$^1$H NMR (400 MHz, CDCl$_3$, δ, ppm, inter alia): 6.48 (dd, 1H, 19-H, J=11 Hz and 17 Hz), 5.77 (d, 1H, 14-H, J=8 Hz), 5.36 (m, 1H, 20-H), 5.22 (d, 1H, 20-H, J=17 Hz), 3.57, 3.36, 3.21, 3.03, 2.72 (5m, 6H, 1'-H, 2'-H, 5'-H, 11-H, 22-H), 2.59 (m, 4H, NCH$_2$), 2.11 (bs, 1H, 4-H), 1.46 (s, 3H, 15-CH$_3$), 1.18 (s, 3H, 18-CH$_3$), 0.98 (t, 6H, NCH$_2$CH$_3$, J=7 Hz), 0.88 (d, 3H, 17-CH$_3$, J=7 Hz), 0.73 (d, 3H, 16-CH$_3$, J=7 Hz).

Step B. 14-O-{[(1R,2R,5S)-5-Diethylamino-2-hydroxy-cyclohexylsulfanyl]-acetyl}-mutilin hydrochloride+(1S,2S,5R) Diastereomer Hydrochloride 14-O-{[(1R,2R,5S)-5-Diethylamino-2-hydroxy-cyclohexylsulfanyl]-acetyl}-mutilin+(1S,2S,5R) diastereomer (230 mg, 0.41 mmol) was treated according to the method of Example 1 Step C to obtain 14-O-{[(1R,2R,5S)-5-diethylamino-2-hydroxy-cyclohexylsulfanyl]-acetyl}-mutilin hydrochloride+(1S,2S,5R) diastereomer hydrochloride (223 mg, 91% yield) as colorless amorphous solid.

$^1$H NMR (400 MHz, CDCl$_3$, δ, ppm, inter alia): 11.5 (bs, 3H, NH$^+$), 6.46 (dd, 1H, 19-H, J=11 Hz and 17 Hz), 5.74 (d, 1H, 14-H, J=8 Hz), 5.34 (m, 1H, 20-H), 5.22 (d, 1H, 22-H, J=17H), 3.98 (m, 1H, 2'-H), 3.60-2.90 (m, 9H, 1'-H, 5'-H, 11-H, 22-H, NCH$_2$), 2.10 (bs, 1H, 4-H), 1.48 (m, 9H, NCH$_2$CH$_3$, 15-CH$_3$), 1.18 (s, 3H, 18-CH$_3$), 0.89 (d, 3H, 17-CH$_3$, J=7 Hz), 0.73 (d, 3H, 16-CH$_3$, J=7 Hz). MS-ESI (m/z): 564 (MH$^+$), 586 (MNa$^+$), 1149 (2MNa$^+$), 598 (MCl$^-$).

Example 9

14-O-{[(1R,2R,4S)-4-Diethylamino-2-hydroxy-cyclohexylsulfanyl]-acetyl}-mutilin+(1S,2S,4R) Diastereomer 14-O-{[(1R,2R,4S)-4-Amino-2-hydroxy-cyclohexylsulfanyl]-acetyl}-mutilin+(1S,2S,4R) diastereomer (680 mg, 1.34 mmol) from Example 2 Step A was treated according to the method of Example 6. After work up and chromatography of the reaction mixture (silica, ethyl acetate/methanol=1/1) 14-O-{[(1R,2R,4S)-4-diethylamino-2-hydroxy-cyclohexylsulfanyl]-acetyl}-mutilin+(1S,2S,4R) diastereomer ($R_f$=0.2, 129 mg, 17%) was obtained as colorless amorphous foam.

$^1$H NMR (500 MHz, DMSO-d$_6$, δ, ppm, inter alia): 6.13 (dd, 1H, 19-H, J=11 Hz and 18 Hz), 5.54 (d, 1H, 14-H, J=8 Hz), 5.05 (m, 2H, 20-H), 4.70 (d, 1H, 2'-OH), 4.49 (d, 1H, 11-OH, J=6 Hz), 3.70 (m, 1H, 2'-H), 3.42 (t, 1H, 11-H, J=6 Hz), AB-system ($v_A$=3.36, $v_B$=3.22, 22-H, J=15 Hz), 2.72 (m, 2H, 1'-H, 4'-H), 2.47 (m, 2H, NCH$_2$), 2.40 (bs, 1H, 4-H), 1.35 (s, 3H, 15-CH$_3$), 1.04 (s, 3H, 18-CH$_3$), 0.95 (t, 3H, NCH$_2$CH$_3$, J=7 Hz), 0.81 (d, 3H, 17-CH$_3$, J=7 Hz), 0.62 (d, 3H, 16-CH$_3$, J=7 Hz). MS-ESI (m/z): 536 (MH$^+$), 558 (MNa$^+$), 534 (M-H)$^-$.

Example 10

14-O-{[(1R,2R,5R)-5-Diethylamino-2-hydroxy-cyclohexylsulfanyl]-acetyl}-mutilin+(1S,2S,5S) Diastereomer 14-O-{[(1R,2R,5R)-5-Amino-2-hydroxy-cyclohexylsulfanyl]-acetyl}-mutilin+(1S,2S,5S) diastereomer (420 mg, 0.827 mmol) from Example 4 Step F was treated according to the method of Example 6. After work up and chromatography of the reaction mixture (silica, ethyl acetate/methanol/35% ammonia solution=50/50/1) 14-O-{[(1R,2R,5R)-5-diethylamino-2-hydroxy-cyclohexylsulfanyl]-acetyl}-mutilin+(1S,2S,5S) diastereomer ($R_f$=0.2, 95 mg, 20%) was obtained as colorless amorphous foam.

$^1$H NMR (400 MHz, DMSO-d$_6$, δ, ppm, inter alia): 6.13 (dd, 1H, 19-H, J=11 Hz and 18 Hz), 5.55 (d, 1H, 14-H, J=8 Hz), 5.05 (m, 2H, 20-H), 4.79 (m, 1H, 2'-OH), 3.55-3.15 (m, 2'-H, 5'-H, 1-H, 22-H), 2.58 (m, 1H, 1'-H), 2.40 (m, 5H, NCH$_2$, 4-H), 1.37 (s, 3H, 15-CH$_3$), 1.06 (s, 3H, 18-CH$_3$), 0.92 (t, 3H, NCH$_2$CH$_3$, J=7 Hz), 0.83 (d, 3H, 17-CH$_3$, J=7 Hz), 0.63 (d, 3H, 16-CH$_3$, J=7 Hz). MS-ESI (m/z): 564 (MH$^+$), 586 (MNa$^+$), 562 (M-H)$^-$, 598 (MCl$^-$).

Example 11

14-O-{[(1R,2R,3R)-3-Ethylamino-2-hydroxy-cyclohexylsulfanyl]-acetyl}-mutilin-1-(1S,2S,3S) Diastereomer Step A. [(1R,2R,3R)-2-Hydroxy-3-(2,4,6-trimethyl-benzylsulfanyl)-cyclohexyl]-carbamic acid tert-butyl ester+(1S,2S,3S) Diastereomer To a solution of (cis)-2,3-epoxycyclohexyl-carbamic acid tert-butyl ether (O'Brien, P.; Childs, A., C.; Ensor, G. *Organic Letters* 2003, 5(26), 4955-4957.) (14.9 g, 68.9 mmol) and 2,4,6-trimethylbenzyl mercaptan (11.5 g, 68.9 mmol) in 50 ml of methanol was added 10N NaOH (5 ml, 50 mmol) and the resulting mixture was stirred for 16 hours at room temperature. The reaction mixture was diluted with water and brine and extracted with ethyl acetate three times. The organic layers were dried over sodium sulfate and filtered. The filtrate was subjected to chromatography (silica, cyclohexane/ethyl acetate=5/1) to yield [(1R,2R,3R)-2-hydroxy-3-(2,4,6-trimethyl-benzylsulfanyl)-cyclohexyl]-carbamic acid tert-butyl ester+(1S,2S,3S) diastereomer ($R_f$=0.25, 5.92 g, 23% yield) as colorless amorphous foam.

$^1$H NMR (400 MHz, DMSO-d$_6$, δ, ppm): 6.78 (s, 2H, aromat.-H), 6.15 (bd, OH), 4.95 (bd, NH), 3.75 (d, 1H, SCH$_2$), 3.68 (m, 2H), 3.02 (m, 1H, SCH), 2.30 (s, 9H, CH$_3$), 2.30, 1.90, 1.40 (3m, 6H), 1.35 (s, 9H, tert-butyl).

Step B. [(1R,2R,3R)-2-(tert-Butyl-dimethyl-silanyloxy)-3-(2,4,6-trimethyl-benzylsulfanyl)-cyclohexyl]-carbamic acid tert-butyl ester+(1S,2S,3S) Diastereomer A solution of [(1R,2R,3R)-2-hydroxy-3-(2,4,6-trimethyl-benzylsulfanyl)-cyclohexyl]-carbamic acid tert-butyl ester+(1S,2S,3S) diastereomer (2.46 g, 6.49 mmol) in 50 ml of dimethylformamide was treated with tert-butyldimethylsilyl chloride (978 mg, 6.49 mmol) and imidazole (552 mg, 8.11 mmol) and stirred at 80° C. for 5 days. The reaction mixture was concentrated under reduced pressure. The residue was diluted with 0.1 N HCl and extracted three times with ethyl acetate. The combined organic layers were washed with brine, dried over sodium sulfate and filtered. After chromatography (silica, cyclohexane/ethyl acetate=10/1) [(1R,2R,3R)-2-(tert-butyl-dimethyl-silanyloxy)-3-(2,4,6-trimethyl-benzylsulfanyl)-cyclo-hexyl]-carbamic acid tert-butyl ester+(1S,2S,3S) diastereomer ($R_f$=0.25, 3.0 g, 94% yield) was obtained.

$^1$H NMR (500 MHz, DMSO-d$_6$, δ, ppm): 6.80 (s, 2H, aromat-H), 6.20 (bd, NH), 3.90, 3.75, 3.63 (3m, 4H, NCH, OCH, SCH$_2$), 2.98 (m, 1H, SCH), 2.30 (s, 9H, CH$_3$), 1.90, 1.50, 1.33 (3m, 6H), 1.35 (s, 9H, C-tert-butyl), 0.85 (s, 9H, Si-tert-butyl), 0.0 (s, 6H, Si(CH$_3$)$_2$).

Step C. [(1R,2R,3R)-2-(tert-Butyl-dimethyl-silanyloxy)-3-(2,4,6-trimethyl-benzylsulfanyl)-cyclohexyl]-ethyl-carbamic acid tert-butyl ester+(1S,2S,3S) Diastereomer A solution of [(1R,2R,3R)-2-(tert-butyl-dimethyl-silanyloxy)-3-(2,4,6-trimethyl-benzylsulfanyl)-cyclohexyl]-carbamic acid tert-butyl ester+(1S,2S,3S) diastereomer (3.0 g, 6.08 mmol) was treated with ethyl iodide according to the method of Example 7 Step A. After work up and chromatography of the reaction mixture (silica, cyclohexane/ethyl acetate=3/1) [(1R,2R,3R)-2-(tert-butyl-dimethyl-silanyloxy)-3-(2,4,6-trimethyl-benzylsulfanyl)-cyclohexyl]-ethyl-carbamic acid tert-butyl ester+(1S,2S,3S) diastereomer (1.20 g, 38%) was obtained.

MS-ESI (m/z): 544 (MNa$^+$), 1065 (2MNa$^+$).

Step D. [(1R,2R,3R)-2-(tert-Butyl-dimethyl-silanyloxy)-3-mercapto-cyclohexyl]-ethyl-carbamic acid tert-butyl ester+(1S,2S,3S) Diastereomer A solution of [(1R,2R,3R)-2-(tert-butyl-dimethyl-silanyloxy)-3-(2,4,6-trimethyl-benzylsulfanyl)-cyclohexyl]-ethyl-carbamic acid tert-butyl ester+(1S,2S,3S) diastereomer (1.20 g, 2.30 mmol) in 10 ml of tetrahydrofuran and 20 ml of liquid ammonia was treated at −78° C. under an argon atmosphere with sodium (106 mg, 4.60 mmol) and stirred at −78° C. for one hour. Then solid ammonium chloride was added and the reaction mixture was warmed to room temperature, diluted with tetrahydrofuran and flushed with nitrogen. The residual mixture was filtered and concentrated under reduced pressure to yield crude [(1R,2R,3R)-2-(tert-butyl-dimethyl-silanyloxy)-3-mercapto-cyclohexyl]-ethyl-carbamic acid tert-butyl ester+(1S,2S,3S) diastereomer (quantitative yield) which was directly used for the next step.

MS-ESI (m/z): 412 (MNa$^+$), 801 (2MNa$^+$).

Step E. 14-O-{[(1R,2R,3R)-3-(tert-Butoxycarbonyl-ethyl-amino)-2-(tert-butyl-dimethyl-silanyloxy)-cyclohexylsulfanyl]-acetyl}-mutilin+(1S,2S,3S) Diastereomer Crude [(1R,2R,3R)-2-(tert-butyl-dimethyl-silanyloxy)-3-mercapto-cyclohexyl]-ethyl-carbamic acid tert-butyl ester+(1S,2S,3S) diastereomer (895 mg, 2.30 mmol) was dissolved in 30 ml of tetrahydrofuran and treated subsequently with pleuromutilin tosylate (979 mg, 1.84 mmol) and potassium tert-butoxide (206 mg, 1.84 mmol) and the resulting mixture was stirred for 16 hours at room temperature. After evaporation of the solvent the residue was diluted with 1N HCl and extracted three times with ethyl acetate. The combined organic layers were washed with NaHCO$_3$ solution and brine, dried over sodium sulfate and filtered. After chromatography (silica, cyclohexane/ethyl acetate=10/1) 14-O-{[(1R,2R,3R)-3-(tert-butoxycarbonyl-ethyl-amino)-2-(tert-butyl-dimethyl-silanyloxy)-cyclohexylsulfanyl]-acetyl}-mutilin+(1S,2S,3S) diastereomer ($R_f$=0.5, 468 mg, 27% yield) was obtained.

$^1$H NMR (400 MHz, DMSO-d$_6$, δ, ppm, inter alia): 6.14 (dd, 1H, 19-H, J=11 Hz and 18 Hz), 5.55 (d, 1H, 14-H, J=8 Hz), 5.05 (m, 2H, 20-H), 4.49 (m, 1H, 11-OH), 3.94 (m, 1H, 2'-H), 3.43 (t, 1H, 11-H, J=6 Hz), 3.28, 3.04 (2m, 5H, 1'-H, 22-H, NCH$_2$), 2.40 (bs, 1H, 4-H), 1.40 (s, 9H, tert-butyl), 1.36, 1.35 (2s, 3H, 15-CH$_3$), 1.05 (s, 3H, 18-CH$_3$), 0.87 (s, 9H, Si-tert-butyl), 0.81 (d, 3H, 17-CH$_3$, J=7 Hz), 0.64, 0.62 (2d, 3H, 16-CH$_3$, J=7 Hz) 0.05, −0.05 (2s, 6H, Si(CH$_3$)$_2$).

Step F. 14-O-{[(1R,2R,3R)-3-Ethylamino-2-(tert-butyl-dimethyl-silanyloxy)-cyclohexylsulfanyl]-acetyl}-mutilin+(1S,2S,3S) Diastereomer and 14-O-{[(1R,2R,3R)-3-Ethylamino-2-hydroxy-cyclohexylsulfanyl]-acetyl}-mutilin+(1S,2S,3S) Diastereomer 14-O-{[(1R,2R,3R)-3-(tert-Butoxycarbonyl-ethyl-amino)-2-(tert-butyl-dimethyl-silanyloxy)-cyclohexylsulfanyl]-acetyl}-mutilin+(1S,2S,3S) diastereomer (468 mg, 0.624 mmol) was treated with trifluoroacetic acid overnight according to, the method of Example 1 Step B. After work up and chromatography of the reaction mixture (silica, ethyl acetate/methanol=1/2) 14-O-{[(1R,2R,3R)-3-ethylamino-2-(tert-butyl-dimethyl-silanyloxy)-cyclohexylsulfanyl]-acetyl}-mutilin+(1S,2S,3S) diastereomer (a) ($R_f$=0.6, 144 mg, 36% yield) and 14-O-{[(1R,2R,3R)-3-ethylamino-2-hydroxy-cyclohexylsulfanyl]-acetyl}-mutilin+(1S,2S,3S) diastereomer (b) ($R_f$=0.25, 177 mg, 53% yield) were obtained as colorless solids.

(a): MS-ESI (m/z): 672 (MNa$^+$), 1321 (2MNa$^+$).

(b): $^1$H NMR (400 MHz, DMSO-d$_6$, δ, ppm, inter alia): 6.14 (dd, 1H, 19-H, J=11 Hz and 18 Hz), 5.54 (d, 1H, 14-H, J=8 Hz), 5.05 (m, 2H, 20-H), 4.76 (m, 1H, 2'-OH), 4.49, 4.48 (2d, 1H, 11-OH, J=6 Hz), 3.55 (m, 1H, 2'-H), 3.42 (t, 1H, 1-H, J=6 Hz), AB-system (ν$_A$=3.37, ν$_B$=3.18, 22-H, J=15 Hz), 3.05 (m, 1H, 3'-H), 2.66 (m, 1H, 1'-H), 2.50 (m, 2H, NCH$_2$), 2.40 (bs, 1H, 4-H), 1.36 (s, 3H, 15-CH$_3$), 1.05 (s, 3H, 18-CH$_3$), 0.98 (t, 3H, NCH$_2$CH$_3$, J=7 Hz), 0.81 (d, 3H, 17-CH$_3$, J=7 Hz), 0.62 (d, 3H, 16-CH$_3$, J=7 Hz). MS-ESI (m/z): 536 (MH$^+$), 558 (MNa$^+$), 1071 (2 MH$^+$), 1093 (2MNa$^+$), 534 (M-H)$^-$.

Example 12

14-O-{[(1R,2R,3R)-3-Diethylamino-2-hydroxy-cyclohexylsulfanyl]-acetyl}-mutilin+(1S,2S,3S) Diastereomer

Step A. 14-O-{[(1R,2R,3R)-3-Diethylamino)-2-(tert-butyl-dimethyl-silanyloxy)-cyclohexylsulfanyl]-acetyl}-mutilin+(1S,2S,3S) Diastereomer 14-O-{[(1R,2R,3R)-3-Ethylamino-2-(tert-butyl-dimethyl-silanyloxy)-cyclohexylsulfanyl]-acetyl}-mutilin+(1S,2S,3S) diastereomer (144 mg, 0.222 mmol) from Example 11 Step F was treated with acetaldehyde (25 μl, 0.444 mmol) according to the method of Example 6. After work up and chromatography of the reaction mixture (silica, ethyl acetate/methanol 2/1) 14-O-{[(1R,2R,3R)-3-diethylamino)-2-(tert-butyl-dimethyl-silanyloxy)-cyclohexylsulfanyl]-acetyl}-mutilin+(1S,2S,3S) diastereomer ($R_f$=0.5, 110 mg, 73%) was obtained as colorless amorphous foam.

$^1$H NMR (400 MHz, DMSO-d$_6$, δ, ppm, inter alia): 6.14 (dd, 1H, 19-H, J=1 Hz and 18 Hz), 5.53 (d, 1H, 14-H, J=7 Hz), 5.05 (m, 2H, 20-H), 4.98 (m, 1H, 11-OH), 3.97 (m, 1H, 2'-H), 3.42 (t, 1H, 11-H, J=6 Hz), 3.24 (m, 2H, H-22), 3.00 (m, 1H, 1'-H), 2.70 (m, 1H, 3'-H), 2.55 (m, 4H, NCH$_2$), 2.40 (bs, 1H, 4-H), 1.36 (s, 3H, 15-CH$_3$), 1.05 (s, 3H, 18-CH$_3$), 0.87 (m, 15H, NCH$_2$CH$_3$, Si-tert-butyl), 0.81 (d, 3H, 17-CH$_3$, J=7 Hz), 0.62, 0.60 (2d, 3H, 16-CH$_3$, J=7 Hz), 0.07 (s, 6H, Si(CH$_3$)$_2$).

Step B. 14-O-{[(1R,2R,3R)-3-Diethylamino-2-hydroxy-cyclohexylsulfanyl]-acetyl}-mutilin+(1S,2S,3S) Diastereomer To a solution of 14-O-{[(1R,2R,3R)-3-diethylamino-2-(tert-butyl-dimethyl-silanyloxy)-cyclohexylsulfanyl]- acetyl}-mutilin+(1S,2S,3S) diastereomer (101 mg, 0.149 mmol) in 5 ml of tetrahydrofuran was added tetrabutylammonium fluoride (0.44 ml, IM in tetrahydrofuran, 0.447 mmol). After stirring at room temperature for 2 days the reaction mixture was concentrated under reduced pressure, diluted with NaHCO$_3$ solution and extracted two times with ethyl acetate. The combined organic layers were dried over sodium sulfate and filtered. The filtrate was subjected to chromatography (silica, ethyl acetate/methanol=1/2) to obtain 14-O-{[(1R,2R,3R)-3-diethylamino-2-hydroxy-cyclohexylsulfanyl]-acetyl}-mutilin+(1S,2S,3S) diastereomer (R$_f$=0.2, 8 mg, 10% yield) as colorless amorphous foam.

$^1$H NMR (400 MHz, DMSO-d$_6$, δ, ppm, inter alia): 6.15, 6.14 (2dd, 1H, 19-H, J=11 Hz and 18 Hz), 5.54 (d, 1H, 14-H, J=8 Hz), 5.05 (m, 2H, 20-H), 4.99, 4.42 (2m, 2H, 11-OH, 2'-OH), 3.87 (m, 1H, 2'-H), 3.42 (t, 1H, 11-H, J=6 Hz), 3.25 (m, 2H, H-22), 3.05 (m, 1H, 1'-H), 2.60 (m, 3H, 3'-H, NCH$_2$), 2.40 (bs, 1H, 4-H), 1.35 (s, 3H, 15-CH$_3$), 1.05 (s, 3H, 18-CH$_3$), 0.90 (m, 6H, NCH$_2$CH$_3$), 0.81 (d, 3H, 17-CH$_3$, J=7 Hz), 0.62, 0.61 (2d, 3H, 16-CH$_3$, J=7 Hz). MS-ESI (m/z): 564 (MH$^+$), 586 (MNa$^+$), 1149 (2MNa$^1$), 562 (M-H)$^-$.

Example 13

14-O-{[(1R,2R,4S)-4-(Formyl-hydroxy-amino)-2-hydroxy-cyclohexylsulfanyl]-acetyl}-mutilin+(1S, 2S,4R) Diastereomer Step A1. 14-O-{[(7R,8R)-7-Hydroxy-1,4-dioxa-spiro [4.5]dec-8-ylsulfanyl]-acetyl}-mutilin+(7S,8S) Diastereomer 7,8-Epoxy-1,4-dioxa-spiro[4.5]decane (Zhang, L.; Koreeda, M. *Organic Letters* 2002, 4(21), 3755-3758.) (6.25 g, 40 mmol) and pleuromutilin thiol (8 g, 20 mmol) were treated according to the method of Example 1 Step A2. After work up and chromatography of the reaction mixture (silica, cyclohexane/ethyl acetate=1/1) 14-O-{[(7R,8R)-7-hydroxy-1,4-dioxa-spiro[4.5]dec-8-ylsulfanyl]-acetyl}-mutilin+(7S, 8S) diastereomer (R$_f$=0.3, 8.40 g, 76% yield) was obtained as colorless amorphous foam.

$^1$H NMR (500 MHz, DMSO-d$_6$, δ, ppm, inter alia): 6.14 (dd, 1H, 19-H, J=11 Hz and 18 Hz), 5.55 (d, 1H, 14-H, J=8 Hz), 5.05 (m, 2H, 20-H), 4.95 (d, 1H, 2'-OH, J=6 Hz), 4.50 (d, 1H, 11-OH, J=6 Hz), 3.82 (m, 4H, OCH$_2$CH$_2$O), 3.55-3.25 (m, 4H, 2'-H, 11-H, H-22), 2.58 (m, 1H, 1'-H), 2.40 (bs, 1H, 4-H), 1.35, 1.34 (2s, 3H, 15-CH$_3$), 1.05 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 573 (MNa$^+$), 549 (M-H)$^-$.

Or Step A2. 14-O-{[(7R,8R)-7-Hydroxy-1,4-dioxa-spiro[4.5]dec-8-ylsulfanyl]-acetyl}-mutilin+(7S,8S) Diastereomer and 14-O-{[(7R,8R)-8-Hydroxy-1,4-dioxa-spiro[4.5]dec-7-ylsulfanyl]-acetyl}-mutilin+ (7S,8S) Diastereomer 7,8-Epoxy-1,4-dioxa-spiro[4.5]decane (6.24 g, 39.95 mmol) and pleuromutilin thiol (16.4 g, 41.7 mmol) were treated according to the method of Example 1 Step A3. After work up and chromatography of the reaction (silica, ethyl acetate/toluene=1/1) a mixture of 14-O-{[(7R,8R)-7-hydroxy-1,4-dioxa-spiro[4.5]dec-8-ylsulfanyl]-acetyl}-mutilin+(7S,8S) diastereomer as well as 14-O-{[(7R,8R)-8-hydroxy-1,4-dioxa-spiro[4.5]dec-7-ylsulfanyl]-acetyl}-mutilin+(7S,8S) diastereomer (R$_f$=0.24, 4.40 g, 20% yield) was obtained as colorless solid.

$^1$H NMR (500 MHz, DMSO-d$_6$, δ, ppm, inter alia): 6.14, 6.12 (2dd, 1H, 19-H, J=11 Hz and 18 Hz), 5.55, 5.53 (2d, 1H, 14-H, J=8 Hz), 5.05 (m, 2H, 20-H), 4.95, 4.87 (d+dd, 1H, 2'-OH, J=6 Hz), 4.50, 4.49 (2d, 1H, 11-OH, J=6 Hz), 3.83 (m, 4H, OCH$_2$CH$_2$O), 3.55-3.25 (m, 4H, 2'-H, 11-H, H-22), 2.77, 2.57 (2m, 1H, 1'-H), 2.40 (bs, 1H, 4-H), 1.36, 1.36 (2s, 3H, 15-CH$_3$), 1.05 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 573 (MNa$^+$), 549 (M-H)$^-$.

Step B. 14-O-{[(7R,8R)-7-(tert-Butyl-diphenyl-silanyloxy)-1,4-dioxa-spiro[4.5]dec-8-ylsulfanyl]-acetyl}-mutilin+(7S,8S) Diastereomer A solution of 14-O-{[(7R,8R)-7-hydroxy-1,4-dioxa-spiro [4.5]dec-8-ylsulfanyl]-acetyl}-mutilin+(7S,8S) diastereomer (8.4 g, 15.3 mmol) from Step A1 in 50 ml of dimethylformamide was treated with tert-butyldiphenylsilyl chloride (5.16 ml, 19.8 mmol) and imidazole (1.66 g, 24.4 mmol) and stirred overnight at 80° C. The reaction mixture was concentrated under reduced pressure. The residue was diluted with water and brine and extracted three times with ethyl acetate. The combined organic layers were washed with water and brine, dried over sodium sulfate and filtered. After chromatography (silica, cyclohexane/ethyl acetate=1/1) 14-O-{[(7R, 8R)-7-(tert-butyl-diphenyl-silanyloxy)-1,4-dioxa-spiro[4.5] dec-8-ylsulfanyl]-acetyl}-mutilin+(7S,8S) diastereomer (R$_f$=0.7, 8.03 g, 67% yield) was obtained.

$^1$H NMR (400 MHz, DMSO-d$_6$, δ, ppm, inter alia): 7.7-7.35 (m, 10H, aromat.-H), 6.15, 6.13 (2dd, 1H, 19-H, J=11 Hz and 18 Hz), 5.57, 5.53 (2d, 1H, 14-H, J=7 Hz), 5.05 (m, 2H, 20-H), 4.50 (m, 1H, 11-OH), 3.30 (m, 1H, 2'-H), 3.70-2.80 (m, 8H, OCH$_2$CH$_2$O, 1'-H, 11-H, 22-H), 2.40 (bs, 1H, 4-H), 1.39, 1.36 (2s, 3H, 15-CH$_3$), 1.05 (s, 3H, 18-CH$_3$), 1.00 (s, 9H, Si-tert-butyl), 0.81 (d, 3H, 17-CH$_3$, J=7 Hz), 0.62, 0.60 (2d, 3H, 16-CH$_3$, J=7 Hz). MS-ESI (m/z): 811 (MNa$^+$).

Step C. 14-O-{[(1R,2R)-2-(tert-Butyl-diphenyl-silanyloxy)-4-oxo-cyclohexylsulfanyl]-acetyl}-mutilin+ (1S,2S) Diastereomer 14-O-{[(7R,8R)-7-(tert-Butyl-diphenyl-silanyloxy)-1,4-dioxa-spiro[4.5]dec-8-ylsulfanyl]-acetyl}-mutilin+(7S,8S) diastereomer (8.03 g, 10.2 mmol) was dissolved in 100 ml of dichloromethane and treated with montmorillonite K10 (10 g) for 3 days at room temperature. After filtration over celite the reaction mixture was concentrated under reduced pressure and subjected to chromatography (silica, cyclohexane/ ethyl acetate=2/1) to yield 14-O-{[(1R,2R)-2-(tert-butyl-diphenyl-silanyloxy)-4-oxo-cyclohexylsulfanyl]-acetyl}-mutilin+(1S,2S) diastereomer (R$_f$=0.38, 5.24 g, 69% yield).

$^1$H NMR (400 MHz, DMSO-d$_6$, δ, ppm, inter alia): 7.65-7.40 (m, 10H, aromat.-H), 6.15, 6.13 (2dd, 1H, 19-H, J=11 Hz and 18 Hz), 5.53 (d, 1H, 14-H, J=7 Hz), 5.00 (m, 2H, 20-H), 4.47 (m, 1H, 11-OH), 4.24 (m, 1H, 2'-H), 3.41 (t, 1H, 11-H, J=6 Hz), 3.20-3.00 (m, 2H, 22-H), 2.60 (m, 1H, 1'-H), 2.40 (bs, 1H, 4-H), 1.35, 1.33 (2s, 3H, 15-CH$_3$), 1.06 (s, 3H, 18-CH$_3$), 0.97 (s, 9H, Si-tert-butyl), 0.81 (d, 3H, 17-CH$_3$, J=7 Hz), 0.58 (d, 3H, 16-CH$_3$, J=7 Hz).

Step D. 14-O-{[(1R,2R)-2-(tert-Butyl-diphenyl-silanyloxy)-4-hydroxyimino-cyclohexylsulfanyl]-acetyl}-mutilin+(1S,2S) Diastereomer To a solution of 14-O-{[(1R,2R)-2-(tert-butyl-diphenyl-silanyloxy)-4-oxo-cyclohexylsulfanyl]-acetyl}-mutilin+(1S, 2S) diastereomer (2.50 g, 3.36 mmol) in 10 ml of dimethylformamide was added hydroxylamine hydrochloride (233 mg, 3.36 mmol) and triethylamine (0.47 ml, 3.36 mmol) and stirred at room temperature overnight. The reaction mixture was concentrated under reduced pressure, diluted with water and brine and extracted three times with ethyl acetate. The combined organic layers were washed twice with water and dried over sodium sulfate and filtered. The solvent was removed under reduced pressure and crude 14-O-{[(1R,2R)-2-(tert-butyl-diphenyl-silanyloxy)-4-hydroxyimino-cyclohexylsulfanyl]-acetyl}-mutilin+(1S,2S) diastereomer (quantitative yield, cyclohexane/ethyl acetate=2/1, $R_f$=0.25, 0.35) is obtained which was used for the next step without further purification.

Step E. 14-O-{[(1R,2R,4S)-2-(tert-Butyl-diphenyl-silanyloxy)-4-hydroxyamino-cyclohexylsulfanyl]-acetyl}-mutilin+(1S,2S,4R) Diastereomer and 14-O-{[(1R,2R,4R)-2-(tert-Butyl-diphenyl-silanyloxy)-4-hydroxyamino-cyclohexylsulfanyl]-acetyl}-mutilin+(1S,2S,4S) Diastereomer 14-O-{[(1R,2R)-2-(tert-Butyl-diphenyl-silanyloxy)-4-hydroxyimino-cyclohexylsulfanyl]-acetyl}-mutilin+(1S,2S) diastereomer (2.55 g, 3.36 mmol) was dissolved in 10 ml of acetic acid and treated with sodium cyanoborohydride (210 mg, 3.36 mmol) for 90 minutes at room temperature. The reaction mixture was concentrated under reduced pressure. The residue was diluted with NaHCO$_3$ solution and extracted three times with ethyl acetate. The combined organic layers were dried over sodium sulfate and filtered. The filtrate was submitted to chromatography (silica, cyclohexane/ethyl acetate=2/3) to yield 14-O-{[(1R,2R,4S)-2-(tert-butyl-diphenyl-silanyloxy)-4-hydroxyamino-cyclohexylsulfanyl]-acetyl}-mutilin+(1S,2S,4R) diastereomer (a) ($R_f$=0.5, 590 mg, 23% yield) and 14-O-{[(1R,2R,4R)-2-(tert-butyl-diphenyl-silanyloxy)-4-hydroxyamino-cyclohexylsulfanyl]-acetyl}-mutilin+(1S,2S,4S) diastereomer (b) ($R_f$=0.3, 670 mg, 26% yield).

(a): $^1$H NMR (400 MHz, DMSO-d$_6$, δ, ppm, inter alia): 7.6-7.35 (m, 10H, aromat.-H), 6.93 (bs, 1H, NH/OH), 6.12, 6.08 (2dd, 11H, 19-H, J=11 Hz and 18 Hz), 5.50 (m, 2H, 14-H, NH/OH), 5.00 (m, 2H, 20-H), 4.47 (m, 1H, 11-OH), 3.95 (m, 1H, 2'-H), 3.40 (t, 1H, 11-H, J=6 Hz), 3.10-2.60 (m, 4H, 1'-H, 4'-H, 22-H), 2.40 (bs, 1H, 4-H), 1.31, 1.30 (2s, 3H, 15-CH$_3$), 1.00 (s, 12H, 18-CH$_3$, Si-tert-butyl), 0.81 (d, 3H, 17-CH$_3$, J=7 Hz), 0.55 (d, 3H, 16-CH$_3$, J=7 Hz).

(b): $^1$H NMR (400 MHz, DMSO-d$_6$, δ, ppm, inter alia): 7.7-7.35 (m, 10H, aromat.-H), 6.85 (s, 1H, NH/OH), 6.16, 6.04 (2dd, 1H, 19-H, J=11 Hz and 18 Hz), 5.55 (m, 2H, 14-H, NH/OH), 5.05 (m, 2H, 20-H), 4.49 (d, 1H, 11-OH, J=6 Hz), 3.55 (m, 1H, 2'-H), 3.42 (t, 1H, 11-H, J=6 Hz), AB-system ($v_A$=3.37, $v_B$=3.18, 22-H, J=14 Hz), 2.88 (m, 1H, 1'-H), 2.54 (m, 1H, 4'-H), 2.40 (bs, 1H, 4-H), 1.39, 1.37 (2s, 3H, 15-CH$_3$), 1.06 (s, 3H, 18-CH$_3$), 1.00 (s, 9H, Si-tert-butyl), 0.83 (d, 3H, 17-CH$_3$, J=7 Hz), 0.64, 0.62 (2d, 3H, 16-CH$_3$, J=7 Hz).

Step F. 14-O-{[(1R,2R,4S)-2-(tert-Butyl-diphenyl-silanyloxy)-4-(formyl-hydroxy-amino-cyclohexyl-sulfanyl]-acetyl}-mutilin+(1S,2S,4R) Diastereomer To a solution of 14-O-{[(1R,2R,4S)-2-(tert-butyl-diphenyl-silanyloxy)-4-hydroxyamino-cyclohexylsulfanyl]-acetyl}-mutilin+(1S,2S,4R) diastereomer (474 mg, 0.622 mmol) in 15 ml of tert-butyl methyl ether was added 2,2,2-trifluoroethyl formate (594 µl, 6.22 mmol) and heated to reflux for 5 hours. The reaction mixture was cooled to room temperature and added dropwise to 150 ml of heptane. The resulting precipitate was isolated by filtration to give 14-O-{[(1R,2R,4S)-2-(tert-butyl-diphenyl-silanyloxy)-4-(formyl-hydroxy-amino-cyclohexylsulfanyl]-acetyl}-mutilin+(1S,2S,4R) diastereomer (307 mg, 62% yield, cyclohexane/ethyl acetate=1/3, $R_f$=0.5) as colorless solid.

$^1$H NMR (400 MHz, DMSO-d$_6$, δ, ppm, inter alia): 9.6, 9.2 (2bs, 1H, NOH), 8.2, 7.9 (2s, 1H, CHO), 7.65-7.35 (m, 10H, aromat.-H), 6.12, 6.08 (2dd, 1H, 19-H, J=11 Hz and 18 Hz), 5.50 (d, 1H, 14-H, J=7 Hz), 5.05 (m, 2H, 20-H), 4.47 (m, 1H, 11-OH), 3.40 (t, 1H, 11-H, J=6 Hz), 2.37 (bs, 1H, 4-H), 1.31, 1.30 (2s, 3H, 15-CH$_3$), 1.03 (s, 12H, 18-CH$_3$, Si-tert-butyl), 0.81 (d, 3H, 17-CH$_3$, J=7 Hz), 0.55 (d, 3H, 16-CH$_3$, J=6 Hz).

Step G. 14-O-{[(1R,2R,4S)-4-(Formyl-hydroxy-amino)-2-hydroxy-cyclohexylsulfanyl]-acetyl}-mutilin+(1S,2S,4R) Diastereomer 14-O-{[(1R,2R,4S)-2-(tert-Butyl-diphenyl-silanyloxy)-4-(formyl-hydroxy-amino-cyclohexyl-sulfanyl]-acetyl}-mutilin+(1S,2S,4R) diastereomer (215 mg, 0.272 mmol) in 10 ml of tetrahydrofuran was treated with tetrabutylammonium fluoride (1.36 ml, 1M in THF, 1.36 mmol) and stirred for 24 hours at room temperature. The reaction was diluted with a mixture of water, NaHCO$_3$ solution and brine (1:1:1) and extracted three times with ethyl acetate. The combined organic layers were dried over sodium sulfate, filtered and concentrated under reduced pressure. The residue was added dropwise to 250 ml heptane. The resulting precipitate was isolated by filtration to yield 14-O-{[(1R,2R,4S)-4-(formyl-hydroxy-amino)-2-hydroxy-cyclohexylsulfanyl]-acetyl}-mutilin+(1S,2S,4R) diastereomer (97 mg, 65% yield, dichloromethane/methanol=9/1, $R_f$=0.4) as colorless solid.

$^1$H NMR (400 MHz, DMSO-d$_6$, δ, ppm, inter alia): 9.65, 9.25 (2bs, 1H, NOH), 8.2, 7.9 (2s, 1H, CHO), 6.13 (m, 1H, 19-H), 5.54 (d, 1H, 14-H, J=8 Hz), 5.05 (m, 2H, 20-H), 4.49 (d, 1H, 11-OH, J=6 Hz), 3.42 (t, 1H, 11-H, J=6 Hz), 2.40 (bs, 1H, 4-H), 1.36 (s, 3H, 15-CH$_3$), 1.06 (s, 12H, 18-CH$_3$), 0.81 (d, 3H, 17-CH$_3$, J=7 Hz), 0.63 (d, 3H, 16-CH$_3$, J=6 Hz). MS-ESI (m/z): 574 (MNa$^+$), 550 (M-H)$^-$, 1101 (2M-H)$^-$.

Example 14

14-O-{[(1R,2R,5S)-5-(Formyl-hydroxy-amino)-2-hydroxy-cyclohexylsulfanyl]-acetyl}-mutilin+(1S, 2S,5R) Diastereomer Step A. (7R,8R)-8-(2,4,6-Trimethylbenzylsufanyl)-1,4-dioxa-spiro[4.5]decan-7-ol+(7S,8S) Diastereomer 7,8-Epoxy-1,4-dioxa-spiro[4.5]decane (Zhang, L.; Koreeda, M. *Organic Letters* 2002, 4(21), 3755-3758.) (22 g, 120 mmol) was treated with 2,4,6-trimethylbenzyl mercaptan (20 g, 120 mmol) according to the method of Example 1 Step A2. After work up and chromatography of the reaction mixture (silica, cyclohexane/ethyl acetate=2/1) (7R,8R)-8-(2,4,6-trimethylbenzylsufanyl)-1,4-dioxa-spiro[4.5]decan-7-ol+(7S,8S) diastereomer ($R_f$=0.4, 33 g, 85% yield) was obtained as oil.

MS-ESI (m/z): 345 (MNa$^+$), 667 (2MNa$^+$).

Step B. Acetic acid (7R,8R)-7-(2,4,6-trimethylbenzylsufanyl)-1,4-dioxa-spiro[4.5]dec-8-yl ester+(7S, 8S) Diastereomer To a solution of triphenylphosphine (26.5 g, 101 mmol) in 500 ml of tetrahydrofuran under argon atmosphere was added isopropyl azodicarboxylate (19.6 ml, 101 mmol) and stirred for 30 minutes. Then (7R,8R)-8-(2,4,6-trimethylbenzylsufanyl)-1,4-dioxa-spiro[4.5]decan-7-ol+(7S,8S) diastereomer (27.7 g, 86 mmol) in 150 ml of tetrahydrofuran and acetic acid (7.7 ml, 135 mmol) were added and the reaction mixture was heated to 80° C. for 24 hours. The resulting reaction mixture was concentrated under reduced pressure and subjected to chromatography (silica, cyclohexane/ethyl acetate/methanol=3/1) to yield acetic acid (7R,8R)-7-(2,4,6-trimethylbenzylsufanyl)-1,4-dioxa-spiro[4.5]dec-8-yl ester+(7S,8S) diastereomer ($R_f$=0.4, 7.0 g, 22% yield).

$^1$H NMR (500 MHz, CDCl$_3$, δ, ppm): 6.81 (s, 2H, aromat.-H), 4.85 (m, 1H, CHO), 3.96 (m, 4H, OCH$_2$CH$_2$O), AB-system ($v_A$=3.83, $v_B$=3.79, J=11 Hz, SCH$_2$), 2.99 (m, 1H, CHS), 2.36 (s, 6H, CH$_3$), 2.23 (s, 3H, CH$_3$), 2.18 (m, 1H), 2.12 (m, 1H), 2.11 (s, 3H, COCH$_3$), 1.90-1.58 (m, 4H). MS-ESI (m/z): 387 (MNa$^+$).

Step C. (7R,8R)-7-Mercapto-1,4-dioxa-spiro[4.5]decan-8-ol+(7S,8S) Diastereomer Acetic acid (7R,8R)-7-(2,4,6-trimethylbenzylsufanyl)-1,4-dioxa-spiro[4.5]dec-8-yl ester+(7S,8S) diastereomer (6.33 g, 17.4 mmol) was treated with sodium (1.6 g, 69.5 mmol) according to the method of Example 11 Step D. After work up and chromatography of the reaction mixture (silica, cyclohexane/ethyl acetate=1/1) (7R,8R)-7-mercapto-1,4-dioxa-spiro[4.5]decan-8-ol+(7S,8S) diastereomer ($R_f$=0.4, 1.36 g, 38%) was obtained.

$^1$H NMR (400 MHz, DMSO-d$_6$, δ, ppm): 4.89 (d, 1H, OH), 3.83 (m, 4H, OCH$_2$CH$_2$O), 3.17 (m, 1H, CHO), 2.76 (m, 1H, CHS), 2.43 (s, 1H, SH), 1.90-1.30, 6H). MS-ESI (m/z): 189 (M-H)$^-$.

Step D. 14-O-{[(7R,8R)-8-Hydroxy-1,4-dioxa-spiro[4.5]dec-7-ylsulfanyl]-acetyl}-mutilin+(7S,8S) Diastereomer (7R,8R)-7-Mercapto-1,4-dioxa-spiro[4.5]decan-8-ol+(7S,8S) diastereomer (1.36 g, 7.15 mmol) was treated with pleuromutilin tosylate (3.8 g, 7.15 mmol) according to the method of Example 11 Step E. After work up and chromatography of the reaction mixture (silica, cyclohexane/ethyl acetate=1/1) 14-O-{[(7R,8R)-8-hydroxy-1,4-dioxa-spiro[4.5]dec-7-ylsulfanyl]-acetyl}-mutilin+(7S,8S) diastereomer ($R_f$=0.25, 1.90 g, 48%) was obtained as colorless amorphous foam.

MS-ESI (m/z): 573 (MNa$^+$), 1123 (2MNa$^+$), 549 (M-H)$^-$, 585 (MCl$^-$).

Step E. 14-O-{1-[(7R,8R)-8-(tert-Butyl-diphenyl-silanyloxy)-1,4-dioxa-spiro[4.5]dec-7-ylsulfanyl]-acetyl}-mutilin+(7S,8S) Diastereomer 14-O-{[(7R,8R)-8-Hydroxy-1,4-dioxa-spiro[4.5]dec-7-ylsulfanyl]-acetyl}-mutilin+(7S,8S) diastereomer (1.90 g, 3.45 mmol) was treated according to the method of Example 13 Step B. After work up and chromatography of the reaction mixture (silica, cyclohexane/ethyl acetate=3/2) 14-O-{[(7R,8R)-8-(tert-butyl-diphenyl-silanyloxy)-1,4-dioxa-spiro[4.5]dec-7-ylsulfanyl]-acetyl}-mutilin+(7S,8S) diastereomer ($R_f$=0.6, 1.65 g, 61%) was obtained as colorless amorphous foam.

$^1$H NMR (400 MHz, DMSO-d$_6$, δ, ppm, inter alia): 7.7-7.35 (m, 10H, aromat.-H), 6.13, 6.12 (2dd, 1H, 19-H, J=11 Hz and 18 Hz), 5.53 (d, 1H, 14-H, J=7 Hz), 5.05 (m, 2H, 20-H), 4.50 (m, 1H, 11-OH), 3.78 (m, 4H, OCH$_2$CH$_2$O), 3.70 (m, 1H, 1'-H), 3.42 (m, 1H, 1-H), 3.05 (m, 3H, 2'-H, 22-H), 2.40 (bs, 1H, 4-H), 1.36, 1.34 (2s, 3H, 15-CH$_3$), 1.05 (s, 3H, 18-CH$_3$), 1.00 (s, 9H, Si-tert-butyl), 0.81 (d, 3H, 17-CH$_3$, J=7 Hz), 0.60, 0.58 (2d, 3H, 16-CH$_3$, J=7 Hz).

Step F. 14-O-{[(1R,2R)-2-(tert-Butyl-diphenyl-silanyloxy)-5-oxo-cyclohexylsulfanyl]-acetyl}-mutilin+(1S,2S) Diastereomer 14-O-{[(7R,8R)-8-(tert-Butyl-diphenyl-silanyloxy)-1,4-dioxa-spiro[4.5]dec-7-ylsulfanyl]-acetyl}-mutilin+(7S,8S) diastereomer (1.65 g, 2.09 mmol) was treated according to the method of Example 13 Step C. Crude 14-O-{[(1R,2R)-2-(tert-butyl-diphenyl-silanyloxy)-5-oxo-cyclohexylsulfanyl]-acetyl}-mutilin+(1S,2S) diastereomer (1.34 g, 86% yield, cyclohexane/ethyl acetate=2/1, $R_f$=0.3) was obtained as colorless amorphous foam which was directly used for the next step.

$^1$H NMR (400 MHz, DMSO-d$_6$, δ, ppm, inter alia): 7.7-7.35 (m, 10H, aromat.-H), 6.11, 6.09 (2dd, 1H, 19-H, J=11 Hz and 18 Hz), 5.48 (d, 1H, 14-H, J=7 Hz), 4.98 (m, 2H, 20-H), 4.47 (m, 1H, 11-OH), 4.03 (m, 1H, 1'-H), 3.45-2.95 (m, 4H, 11-H, 2'-H, 22-H), 2.37 (bs, 1H, 4-H), 1.31, 1.29 (2s, 3H, 15-CH$_3$), 1.02 (s, 12H, 18-CH$_3$, Si-tert-butyl), 0.81 (d, 3H, 17-CH$_3$, J=7 Hz), 0.53 (d, 3H, 16-CH$_3$, J=7 Hz). MS-ESI (m/z): 767 (MNa$^+$), 779 (MCl$^-$).

Step G. 14-O-{[(1R,2R)-2-(tert-Butyl-diphenyl-silanyloxy)-5-hydroxyimino-cyclohexylsulfanyl]-acetyl}-mutilin+(1S,2S) Diastereomer 14-O-{[(1R,2R)-2-(tert-Butyl-diphenyl-silanyloxy)-5-oxo-cyclohexylsulfanyl]-acetyl}-mutilin+(1S,2S) diastereomer (1.34 g, 1.80 mmol) was treated according to the method of Example 13 Step D. Crude 14-O-{[(1R,2R)-2-(tert-butyl-diphenyl-silanyloxy)-5-hydroxyimino-cyclohexylsulfanyl]-acetyl}-mutilin+(1S,2S) diastereomer (quantitative yield, cyclohexane/ethyl acetate=1/1, $R_f$=0.6) was obtained as colorless amorphous foam which was directly used for the next step.

Step H. 14-O-{[(1R,2R,5S)-2-(tert-Butyl-diphenyl-silanyloxy)-5-hydroxyamino-cyclohexylsulfanyl]-acetyl}-mutilin+(1S,2S,5R) Diastereomer and 14-O-{[(1R,2R,5R)-2-(tert-Butyl-diphenyl-silanyloxy)-5-hydroxyamino-cyclohexylsulfanyl]-acetyl}-mutilin+(1S,2S,5S) Diastereomer 14-O-{[(1R,2R)-2-(tert-butyl-diphenyl-silanyloxy)-5-hydroxyimino-cyclohexylsulfanyl]-acetyl}-mutilin+(1S,2S) diastereomer (2.55 g, 3.36 mmol) was treated according to the method of Example 13 Step E. After work up and chromatography of the reaction mixture (silica, cyclohexane/ethyl acetate=1/3) 14-O-{[(1R,2R,5S)-2-(tert-butyl-diphenyl-silanyloxy)-5-hydroxyamino-cyclohexylsulfanyl]-acetyl}-mutilin+(1S,2S,5R) diastereomer (a) ($R_f$=0.4, 220 mg, 16% yield) and 14-O-{[(1R,2R,5R)-2-(tert-butyl-diphenyl-silanyloxy)-5-hydroxyamino-cyclohexylsulfanyl]-acetyl}-mutilin+(1S,2S,5S) diastereomer (b) ($R_f$=0.25, 560 mg, 41% yield) were obtained.

(a): $^1$H NMR (400 MHz, DMSO-d$_6$, δ, ppm, inter alia): 7.65-7.35 (m, 10H, aromat.-H), 7.00 (bs, 1H, NH/OH), 6.11, 6.09 (2dd, 1H, 19-H, J=11 Hz and 18 Hz), 5.50 (d, 1H, 14-H, J=8 Hz), 5.00 (m, 2H, 20-H), 4.47 (m, 1H, 11-OH), 3.80 (m, 1H, 2'-H), 3.40 (t, 1H, 11-H, J=6 Hz), 3.00 (m, 1H, 1'-H), AB-system ($v_A$=3.93, $v_B$=3.80, 22-H, J=15 Hz), 2.68 (m, 1H, 5'-H), 2.40 (bs, 1H, 4-H), 1.31, 1.29 (2s, 3H, 15-CH$_3$), 1.00 (s, 12H, 18-CH$_3$, Si-tert-butyl), 0.81 (d, 3H, 17-CH$_3$, J=7 Hz), 0.55 (d, 3H, 16-CH$_3$, J=7 Hz).

(b): $^1$H NMR (400 MHz, DMSO-d$_6$, δ, ppm, inter alia): 7.7-7.35 (m, 10H, aromat.-H), 6.97 (s, 1H, NH/OH), 6.16, 6.14 (2dd, 1H, 19-H, J=11 Hz and 18 Hz), 5.56 (m, 2H, 14-H), 5.40 (bs, 1H, NH/OH), 5.07 (m, 2H, 20-H), 4.49, 4.48 (2d, 1H, 11-OH, J=6 Hz), 3.48 (m, 1H, 2'-H), 3.43 (t, 1H, 11-H, J=6 Hz), 3.24 (m, 2H, 22-H), 2.79 (m, 1H, 1'-H), 2.40 (bs, 1H, 4-H), 2.33 (m, 1H, 5'-H), 1.38, 1.35 (2s, 3H, 15-CH$_3$), 1.05 (s, 3H, 18-CH$_3$), 0.98 (s, 9H, Si-tert-butyl), 0.81 (d, 3H, 17-CH$_3$, J=7 Hz), 0.63, 0.61 (2d, 3H, 16-CH$_3$, J=6 Hz).

Step I. 14-O-{1-[(1R,2R,5S)-2-(tert-Butyl-diphenyl-silanyloxy)-5-(formyl-hydroxy-amino-cyclohexyl-sulfanyl]-acetyl}-mutilin+(1S,2S,5R) Diastereomer 14-O-{[(1R,2R,5S)-2-(tert-butyl-diphenyl-silanyloxy)-5-hydroxyamino-cyclohexylsulfanyl]-acetyl}-mutilin+(1S,2S,5R) diastereomer (215 mg, 0.282 mmol) was treated according to the method of Example 13 Step F. Isolation of the precipitate by filtration resulted in 14-O-{[(1R,2R,5S)-2-(tert-butyl-diphenyl-silanyloxy)-5-(formyl-hydroxy-amino-cyclohexylsulfanyl]-acetyl}-mutilin+(1S,2S,5R) diastereomer (135 mg, 61% yield, cyclohexane/ethyl acetate=1/3, R$_f$=0.65) as colorless solid.

$^1$H NMR (400 MHz, DMSO-d$_6$, δ, ppm, inter alia): 9.8, 9.3 (2bs, 1H, NOH), 8.2, 7.9 (2bs, 1H, CHO), 7.60-7.35 (m, 101H, aromat.-H), 6.11, 6.09 (2dd, 1H, 19-H, J=11 Hz and 18 Hz), 5.50 (d, 1H, 14-H, J=8 Hz), 5.00 (m, 2H, 20-H), 4.47 (d, 1H, 11-OH, J=6 Hz), 3.40 (t, 1H, 11-H, J=6 Hz), 2.37 (bs, 1H, 4-H), 1.32, 1.30 (2s, 3H, 15-CH$_3$), 1.03 (s, 12H, 18-CH$_3$, Si-tert-butyl), 0.82, 0.80 (d, 3H, 17-CH$_3$, J=7 Hz), 0.55 (d, 3H, 16-CH$_3$, J=6 Hz).

Step J. 14-O-{[(1R,2R,5S)-5-(Formyl-hydroxy-amino)-2-hydroxy-cyclohexylsulfanyl]-acetyl}-mutilin+(1S,2S,5R) Diastereomer 14-O-{[(1R,2R,5S)-2-(tert-Butyl-diphenyl-silanyloxy)-5-(formyl-hydroxy-amino-cyclohexyl-sulfanyl]-acetyl}-mutilin+(1S,2S,5R) diastereomer (130 mg, 0.164 mmol) was treated according to the method of Example 13 Step G. Isolation of the precipitate by filtration resulted in 14-O-{[(1R,2R,5S)-5-(formyl-hydroxy-amino)-2-hydroxy-cyclohexylsulfanyl]-acetyl}-mutilin+(1S,2S,5R) diastereomer (77 mg, 85% yield, dichloromethane/methanol=9/1, R$_f$=0.4) as colorless solid.

$^1$H NMR (400 MHz, DMSO-d$_6$, δ, ppm, inter alia): 9.7, 9.3 (2bs, 11H, NOH), 8.2, 7.9 (2s, 11H, CHO), 6.13 (dd, 11H, 19-H, J=11 Hz and 18 Hz), 5.53 (d, 11H, 14-H, J=8 Hz), 5.06 (m, 2H, 20-H), 4.91 (d, 1H, 2'-OH), 4.49 (d, 11H, 11-OH, J=6 Hz), 4.2, 3.7 (2m, 2H, 2'-H, 5'-H), 3.41 (t, 11H, 11-H, J=6 Hz), 3.28 (m, 2H, 22-H), 3.13 (m, 11H, 1'-H), 2.40 (bs, 11H, 4-H), 1.35 (s, 3H, 15-CH$_3$), 1.06 (s, 12H, 18-CH$_3$), 0.81 (d, 3H, 17-CH$_3$, J=7 Hz), 0.63 (d, 3H, 16-CH$_3$, J=6 Hz). MS-ESI (m/z): 574 (MNa$^+$), 1125 (MNa$^+$), 550 (M-H)$^-$, 1101 (2M-H)$^-$.

Example 15

14-O-{[(1R,2R,3R/S)-3-(Formyl-hydroxy-amino)-2-hydroxy-cyclohexylsulfanyl]-acetyl}-mutilin+(1S,2S,3R/S) Diastereomer Step A. 14-O-{[(6R,7R)-6-Hydroxy-1,4-dioxa-spiro[4.5]dec-7-ylsulfanyl]-acetyl}-mutilin+(6S,7S) Diastereomer 6,7-Epoxy-1,4-dioxa-spiro[4.5]decane (Vankar, Y. D.; Reddy M. V.; Chaudhuri, N. C. *Tetrahedron* 1994, 50(37), 11057-11078.) (16.24 g, 104 mmol) and pleuromutilin thiol (20.5 g, 52 mmol) were treated according to the method of Example 1 Step A1. After work up and chromatography of the reaction mixture (silica, cyclohexane/dioxane=2/1) 14-O-{[(6R,7R)-6-hydroxy-1,4-dioxa-spiro[4.5]dec-7-ylsulfanyl]-acetyl}-mutilin+(6S,7S) diastereomer (R$_f$=0.5, 15.6 g, 55% yield) was obtained as colorless amorphous foam.

$^1$H NMR (400 MHz, DMSO-d$_6$, δ, ppm, inter alia): 6.13 (dd, 1H, 19-H, J=11 Hz and 18 Hz), 5.53 (d, 1H, 14-H, J=7 Hz), 5.05 (m, 2H, 20-H), 4.90 (m, 1H, 2'-OH), 4.47 (m, 1H, 1-OH), 3.97 (m, 1H, 2'-H), 3.32 (m, 1H, 11-H), 3.50-3.20 (m, 2H, 22-H), 2.80 (m, 1H, 1'-H), 2.40 (bs, 1H, 4-H), 1.35, 1.34 (2s, 3H, 15-CH$_3$), 1.05 (s, 3H, 18-CH$_3$), 0.81 (d, 3H, 17-CH$_3$, J=7 Hz), 0.62 (d, 3H, 16-CH$_3$, J=6 Hz).

Step B. 14-O-{[(1R,2R)-2-Hydroxy-3-oxo-cyclohexylsulfanyl]-acetyl}-mutilin+(1S,2S) Diastereomer 14-O-{[(6R,7R)-6-Hydroxy-1,4-dioxa-spiro[4.5]dec-7-ylsulfanyl]-acetyl}-mutilin+(6S,7S) diastereomer (15.6 g, 28.4 mmol) was treated according to the method of Example 13 Step C. After work up and chromatography of the reaction mixture (silica, cyclohexane/ethyl acetate=1/1) 14-O-{[(1R,2R)-2-hydroxy-3-oxo-cyclohexylsulfanyl]-acetyl}-mutilin+(1S,2S) diastereomer (R$_f$=0.4, 3.14 g, 22% yield) was obtained as colorless amorphous foam.

$^1$H NMR (400 MHz, DMSO-d$_6$, δ, ppm, inter alia): 6.13 (dd, 1H, 19-H, J=11 Hz and 18 Hz), 5.55 (d, 1H, 14-H, J=8 Hz), 5.23 (m, 1H, 2'-OH), 5.05 (m, 2H, 20-H), 4.49 (d, 1H, 11-OH, J=6 Hz), 4.00 (m, 1H, 2'-H), 3.50-3.30 (m, 3H, 1-H, 22-H), 2.86 (m, 1H, 1'-H), 2.40 (bs, 1H, 4-H), 1.35 (s, 3H, 15-CH$_3$), 1.06 (s, 3H, 18-CH$_3$), 0.80 (d, 3H, 17-CH$_3$, J=7 Hz), 0.61 (d, 3H, 16-CH$_3$, J=7 Hz). MS-ESI (m/z): 529 (MNa$^+$), 1035 (2MNa$^+$).

Step C. 14-O-{[(1R,2R)-2-Hydroxy-3-hydroxy-imino-cyclohexylsulfanyl]-acetyl}-mutilin+(1S,2S) Diastereomer 14-O-{[(1R,2R)-2-Hydroxy-3-oxo-cyclohexylsulfanyl]-acetyl}-mutilin+(1S,2S) diastereomer (3.14 g, 6.19 mmol) was treated according to the method of Example 13 Step D. After work up and chromatography of the reaction mixture (silica, cyclohexane/ethyl acetate=1/1) 14-O-{[(1R,2R)-2-hydroxy-3-hydroxyimino-cyclohexylsulfanyl]-acetyl}-mutilin+(1S,2S) diastereomer (R$_f$=0.2, 1.75 g, 54% yield) was obtained as colorless amorphous foam.

$^1$H NMR (400 MHz, DMSO-d$_6$, δ, ppm, inter alia): 10.5 (s, 1H, NOH), 6.13, 6.12 (2dd, 1H, 19-H, J=11 Hz and 18 Hz), 5.54 (d, 1H, 14-H, J=8 Hz), 5.33 (d, 1H, 2'-OH, J=4 Hz), 5.05 (m, 2H, 20-H), 4.50 (m, 1H, 11-OH), 3.96 (m, 1H, 2'-H), 3.42 (t, 1H, 11-H, J=6 Hz), 3.25 (m, 2H, 22-H), 3.14 (m, 1H, 1'-H), 2.40 (bs, 1H, 4-H), 1.35 (s, 3H, 15-CH$_3$), 1.05 (s, 3H, 18-CH$_3$), 0.81 (d, 3H, 17-CH$_3$, J=7 Hz), 0.63 (d, 3H, 16-CH$_3$, J=7 Hz).

Step D. 14-O-{[(1R,2R,3R/S)-2-Hydroxy-3-hydroxyamino-cyclohexylsulfanyl]-acetyl}-mutilin+(1S,2S,3R/S) Diastereomer 14-O-{[(1R,2R)-2-Hydroxy-3-hydroxyimino-cyclohexylsulfanyl]-acetyl}-mutilin+(1S,2S) diastereomer (1.75 g, 3.35 mmol) was treated according to the method of Example 13 Step E. After work up and chromatography of the reaction mixture (silica, ethyl acetate/methanol=10/1) 14-O-{[(1R,2R,3R/S)-2-hydroxy-3-hydroxyamino-cyclohexylsulfanyl]- acetyl}-mutilin+(1S,2S,3R/S) diastereomer (R$_f$=0.2, 1.34 g, 65% yield) was obtained as colorless amorphous foam.

$^1$H NMR (400 MHz, DMSO-d$_6$, δ, ppm, inter alia): 7.1 (bs, 1H, NH/OH), 6.12, 6.11 (2dd, 1H, 19-H, J=11 Hz and 18 Hz), 5.53 (d, 1H, 14-H, J=8 Hz), 5.05 (m, 2H, 20-H), 4.90 (m, 1H, 2'-OH), 4.5 (m, 1H, 11-OH), 3.41 (t, 1H, 11-H, J=6 Hz), 3.73, 3.53, 3.30, 3.14, 3.01, 2.87 (6m, 5H, 1'-H, 2'-H, 3'-H, 22-H), 2.40 (bs, 1H, 4-H), 1.35 (2s, 3H, 15-CH$_3$), 1.05 (s, 3H, 18-CH$_3$), 0.81 (d, 3H, 17-CH$_3$, J=7 Hz), 0.63 (d, 3H, 16-CH$_3$, J=7 Hz).

Step E. 14-O-{[(1R,2R,3R/S)-3-(Formyl-hydroxy-amino)-2-hydroxy-cyclohexylsulfanyl]-acetyl}-mutilin+(1S,2S,3R/S) Diastereomer 14-O-{[(1R,2R,3R/S)-2-hydroxy-3-hydroxyamino-cyclohexylsulfanyl]-acetyl}-mutilin+(1S,2S,3R/S) diastereomer (899 mg, 1.72 mmol) was treated according to the method of Example 13 Step F. After isolation of the precipitate by filtration 14-O-{[(1R,2R,3R/S)-3-(formyl-hydroxyamino)-2-hydroxy-cyclohexylsulfanyl]-acetyl}-mutilin+(1S,2S,3R/S) diastereomer (724 mg, 76% yield, dichloromethane/methanol=9/1, R$_f$=0.5) was obtained as colorless solid.

$^1$H NMR (400 MHz, DMSO-d$_6$, δ, ppm, inter alia): 9.6, 9.9.4, 9.1 (3bs, 1H, NOH), 8.2, 7.9 (2s, 1H, CHO), 6.13, 6.11 (2dd, 1H, 19-H, J=11 Hz and 18 Hz), 5.54 (d, 1H, 14-H, J=8 Hz), 5.24 (m, 1H, 2'-OH), 5.05 (m, 2H, 20-H), 4.49 (m, 1H, 11-OH), 3.86, 3.60 (2m, 1H, 2'-H), 3.39 (t, 1H, 11-H, J=6 Hz), 3.28, 3.13, 2.64 (3m, 4H, 1'-H, 3'-H, 22-H), 2.38 (bs, 1H, 4-H), 1.36 (s, 3H, 15-CH$_3$), 1.06 (s, 12H, 18-CH$_3$), 0.81 (d, 3H, 17-CH$_3$, J=7 Hz), 0.63 (d, 3H, 16-CH$_3$, J=7 Hz). MS-ESI (m/z): 574 (MNa$^+$), 1125 (2MNa$^+$), 550 (M-H)$^-$, 1101 (2M-H)$^-$.

Example 16

14-O-{[(1R,2R,5S)-2-Hydroxy-5-methylamino-cyclohexylsulfanyl]-acetyl}-mutilin hydrochloride+(1S,2S,5R) Diastereomer Hydrochloride

Step A. N-Methyl-N-(cyclohex-3-enyl)-carbamic acid tert-butyl ester

Cyclohex-3-enyl-carbamic acid tert-butyl ester (Kampferer, P.; Vasella, A. *Helvetica Chimica Acta* 2004, 87, 2764-2789) (3 g, 15.2 mmol) and methyl iodide (0.95 ml, 15.2 mmol) were treated for 1 hour according to the method of Example 7 Step A. After work up and chromatography of the reaction mixture (silica, cyclohexane/ethyl acetate=10/1) the title compound (R$_f$=0.22, 2.04 g, 64% yield) was obtained as colorless solid.

$^1$H NMR (200 MHz, CDCl$_3$, δ, ppm): 5.64 (bs, 2H, double bond), 4.17 (bs, 1H, NCH), 2.74 (s, 3H, NCH$_3$), 2.13, 1.70 (2m, 6H), 1.47 (s, 9H, tert-butyl).

Step B. N-Methyl-N-(cis-3,4-epoxycyclohexyl)-carbamic acid tert-butyl ester

N-Methyl-N-(cyclohex-3-enyl)-carbamic acid tert-butyl ester (2 g, 9.5 mmol) and 3-chloroperbenzoic acid (2.2 g, 70%, 8.9 mmol) were treated for 1 hour according to the method of Example 7 Step B. After work up the crude title compound (silica, cyclohexane/ethyl acetate=3/1, R$_f$=0.25, 1.70 g, 79% yield) was obtained.

$^1$H NMR (200 MHz, CDCl$_3$, δ, ppm): 4.0 (bs, 11H, NCH), 3.15 (bs, 2H, epoxide), 2.67 (s, 3H, NCH$_3$), 2.30-1.10 (m, 6H), 1.45 (s, 9H, tert-butyl).

Step C. 14-O-{[(1R,2R,5S)-5-(tert-Butoxycarbonyl-methyl-amino)-2-hydroxy-cyclohexylsulfanyl]-acetyl}-mutilin+(1S,2S,5R) Diastereomer N-Methyl-N-(cis-3,4-epoxycyclohexyl)-carbamic acid tert-butyl ester (1.7 g, 7.5 mmol) was treated with pleuromutilin thiol (2.95 g, 7.5 mmol) according to the method of Example 1 Step A3. After work up and chromatography of the reaction mixture (silica, cyclohexane/ethyl acetate=2/1) 14-O-{[(1R,2R,5S)-5-(tert-Butoxycarbonyl-methyl-amino)-2-hydroxy-cyclohexylsulfanyl]-acetyl}-mutilin+(1S,2S,5R) diastereomer (R$_f$=0.23, 1.3 g, 28% yield) was obtained as colorless solid.

$^1$H NMR (400 MHz, DMSO-d$_6$, δ, ppm, inter alia): 6.12 (2dd, 1H, 19-H, J=11 Hz and 18 Hz), 5.54 (d, 1H, 14-H, J=8 Hz), 5.05 (m, 2H, 20-H), 4.9 (d, 1H, 2'-OH, J=4 Hz), 4.47 (d, 1H, 11-OH, J=6 Hz), 3.97 (m, 1H, 5'-H), 3.70 (bs, 1H, 2'-H), 3.42 (m, 1H, 11-H), 3.28 (m, 2H, 22-H), 3.11 (m, 1H, 1'-H), 2.62 (s, 3H, NCH$_3$), 2.40 (bs, 1H, 4-H), 1.37 (s, 9H, tert-butyl), 1.35 (s, 3H, 15-CH$_3$), 1.04 (s, 3H, 18-CH$_3$), 0.81 (d, 3H, 17-CH$_3$, J=7 Hz), 0.63 (d, 3H, 16-CH$_3$, J=7 Hz).

Step D. 14-O-{[(1R,2R,5S)-2-Hydroxy-5-methylamino-cyclohexylsulfanyl]-acetyl}-mutilin+(1S,2S,5R) Diastereomer 14-O-{[(1R,2R,5S)-5-(tert-Butoxycarbonyl-methyl-amino)-2-hydroxy-cyclohexylsulfanyl]-acetyl}-mutilin+(1S,2S,5R) diastereomer (1.3 g, 2.1 mmol) was treated according to the method of Example 1 Step B. After work up and chromatography of the reaction mixture (silica, dichloromethane/methanol/1-propanol/water/acetic acid=80/20/6/3/2) with subsequent basic extraction 14-O-{[(1R,2R,5S)-2-hydroxy-5-methylamino-cyclohexylsulfanyl]-acetyl}-mutilin+(1S,2S,5R) diastereomer (R$_f$=0.4, 690 mg, 63%) was obtained as colorless solid.

$^1$H NMR (500 MHz, DMSO-d$_6$, δ, ppm, inter alia): 6.14 (dd, 1H, 19-H, J=11 Hz and 18 Hz), 5.54 (d, 1H, 14-H, J=8 Hz), 5.06 (m, 2H, 20-H), 4.81 (bs, 1H, 2'-OH), 4.52 (d, 1H, 11-OH, J=6 Hz), 3.51 (m, 1H, 2'-H), 3.43 (m, 1H, 11-H), 3.30 (m, 2H, 22-H), 3.00 (m, 1H, 1'-H), 2.63 (m, 1H, 5'-H), 2.41 (bs, 1H, 4-H), 2.29 (s, 3H, NCH$_3$), 1.37 (s, 3H, 15-CH$_3$), 1.06 (s, 3H, 18-CH$_3$), 0.82 (d, 3H, 17-CH$_3$, J=7 Hz), 0.64 (d, 3H, 16-CH$_3$, J=7 Hz).

Step E. 14-O-{[(1R,2R,5S)-2-Hydroxy-5-methylamino-cyclohexylsulfanyl]-acetyl}-mutilin hydrochloride+(1S,2S,5R) Diastereomer Hydrochloride 14-O-{[(1R,2R,5S)-2-Hydroxy-5-methylamino-cyclohexylsulfanyl]-acetyl}-mutilin+(1S,2S,5R) diastereomer (690 mg, 1.32 mmol) was treated according to the method of Example 1 Step C to obtain 14-O-{[(1R,2R,5S)-2-hydroxy-5-methylamino-cyclohexylsulfanyl]-acetyl}-mutilin hydrochloride+(1S,2S,5R) diastereomer hydrochloride (731 mg, quantitative yield) as colorless solid.

$^1$H NMR (400 MHz, DMSO-d$_6$, δ, ppm, inter alia): 8.65 (1's, 2H, NH$_2^+$), 6.14 (2dd, 1H, 19-H, J=11 Hz and 18 Hz), 5.54 (d, 1H, 14-H, J=8 Hz), 5.06 (m, 2H, 20-H), 4.51 (d, 1H, 11-OH, J=6 Hz), 3.72 (m, 1H, 2'-H), 3.43 (m, 1H, 11-H), 3.37-3.00 (m, 4H, 22-H, 1'-H, 5'-H), 2.50 (s, 3H, NCH$_3$), 2.40 (bs, 1H, 4-H), 1.36 (s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=7 Hz). MS-ESI (m/z): 522 (MH$^+$), 556 (MCl$^-$).

Example 17

14-O-{[(1R,2R,5S)-5-Allylamino-2-hydroxy-cyclohexylsulfanyl]-acetyl}-mutilin hydrochloride+(1S,2S,5R) Diastereomer Hydrochloride Step A. N-Allyl-N-(cyclohex-3-enyl)-carbamic acid tert-butyl ester Cyclohex-3-enyl-carbamic acid tert-butyl ester (Kampferer, P.; Vasella, A. *Helvetica Chimica Acta* 2004, 87, 2764-2789) (3 g, 15.2 mmol) and allyl iodide (1.4 ml, 15.2 mmol) were treated overnight according to the method of Example 7 Step A. After work up and chromatography of the reaction mixture (silica, cyclohexane/ethyl acetate=10/1) the title compound (R$_f$=0.55, 2.0 g, 55% yield) was obtained as colorless solid.
$^1$H NMR (200 MHz, CDCl$_3$, δ, ppm): 5.60 (m, 2H, double bond), 5.80, 5.10, 3.64 (3m, 5H, allyl), 4.18 (bs, 1H, NCH), 2.14, 1.74 (2m, 6H), 1.45 (s, 9H, tert-butyl).

Step B. N-Allyl-N-(cis-3,4-epoxycyclohexyl)-carbamic acid tert-butyl ester

N-Allyl-N-(cyclohex-3-enyl)-carbamic acid tert-butyl ester (2 g, 8.4 mmol) and 3-chloroperbenzoic acid (2.2 g, 70%, 8.9 mmol) were treated overnight according to the method of Example 7 Step B. After work up the crude title compound (silica, cyclohexane/ethyl acetate=3/1, R$_f$=0.31, 1.90 g, 89% yield) was obtained.
$^1$H NMR (200 MHz, CDCl$_3$, δ, ppm): 5.76, 5.10, 3.66 (3m, 5H, allyl), 4.04 (bs, 1H, NCH), 3.12 (bs, 2H, epoxide), 2.30-1.20 (m, 6H), 1.47 (s, 9H, tert-butyl).

Step C. 14-O-{1-[(1R,2R,5S)-5-(tert-Butoxycarbonyl-allyl-amino)-2-hydroxy-cyclohexylsulfanyl]-acetyl}-mutilin+(1S,2S,5R) Diastereomer N-Allyl-N-(cis-3,4-epoxycyclohexyl)-carbamic acid tert-butyl ester (1.9 g, 7.5 mmol) was treated with Pleuromutilin thiol (2.95 g, 7.5 mmol) according to the method of Example 1 Step A2. After work up and chromatography of the reaction (silica, cyclohexane/ethyl acetate=3/1->1/1) a mixture of 14-O-{[(1R,2R,5S)-5-(tert-Butoxycarbonyl-allyl-amino)-2-hydroxy-cyclohexylsulfanyl]-acetyl}-mutilin+(1S,2S,5R) diastereomer and Pleuromutilin disulfide (cyclohexane/ethyl acetate=1/1, R$_f$=0.21, 2.49 g) was obtained.
$^1$H NMR (400 MHz, DMSO-d$_6$, δ, ppm, inter alia): 6.12 (2dd, 1H, 19-H, J=11 Hz and 18 Hz), 5.74 (m, 1H, NCH$_2$CHCH$_2$), 5.54 (d, 1H, 14-H, J=8 Hz), 5.05 (m, 4H, 20-H, NCH$_2$CHCH$_2$), 4.87 (d, 1H, 2'-OH, J=3 Hz), 4.49 (d, 1H, 11-OH, J=6 Hz), 3.95 (m, 1H, 5'-H), 3.68 (bs, 3H, 2'-H, NCH$_2$CHCH$_2$), 3.42 (t, 1H, 11-H, J=6 Hz), 3.26 (m, 1H, 22-H), 3.09 (m, H, 1'-H), 2.39 (bs, 1H, 4-H), 1.37 (s, 9H, tert-butyl), 1.35 (s, 3H, 15-CH$_3$), 1.05 (s, 3H, 18-CH$_3$), 0.81 (d, 3H, 17-CH$_3$, J=7 Hz), 0.63 (d, 3H, 16-CH$_3$, J=7 Hz). MS-ESI (m/z): 670 (MNa$^+$), 1317 (2MNa$^+$), 646 (M-H)$^-$.

Step D. 14-O-{[(1R,2R,5S)-5-Allylamino-2-hydroxy-cyclohexylsulfanyl]-acetyl}-mutilin+(1S,2S,5R) Diastereomer The mixture of 14-O-{[(1R,2R,5S)-5-(tert-Butoxycarbonyl-allyl-amino)-2-hydroxy-cyclohexylsulfanyl]-acetyl}-mutilin+(1S,2S,5R) diastereomer and Pleuromutilin disulfide (2.4 g) was treated according to the method of Example 1 Step B. After work up and chromatography of the reaction mixture (silica, dichloromethane/methanol/1-propanol/water/acetic acid=80/20/6/3/2) with subsequent basic extraction 14-O-{[(1R,2R,5S)-5-allylamino-2-hydroxy-cyclohexylsulfanyl]-acetyl}-mutilin+(1S,2S,5R) diastereomer (R$_f$=0.5, 250 mg) was obtained as colorless solid.
$^1$H NMR (500 MHz, DMSO-d$_6$, δ, ppm, inter alia): 6.14 (dd, 1H, 19-H, J=11 Hz and 18 Hz), 5.82 (m, 1H, NCH$_2$CHCH$_2$), 5.55 (d, 1H, 14-H, J=8 Hz), 5.10 (m, 4H, 20-H, NCH$_2$CHCH$_2$), 4.77 (m, 1H, 2'-OH), 4.51 (d, 1H, 11-OH, J=6 Hz), 3.50-3.10 (m, 6H, 2'-H, 11-H, 22-H, NCH$_2$CHCH$_2$), 2.99 (m, 1H, 1'-H), 2.68 (m, 1H, 5'-H), 2.40 (bs, 1H, 4-H), 1.37 (s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=7 Hz). MS-ESI (m/z): 548 (MH$^+$), 546 (M-H)$^-$, 582 (MCl$^-$).

Step E. 14-O-{[(1R,2R,5S)-5-Allylamino-2-hydroxy-cyclohexylsulfanyl]-acetyl}-mutilin hydrochloride+(1S,2S,5R) Diastereomer Hydrochloride 14-O-{[(1R,2R,5S)-5-Allylamino-2-hydroxy-cyclohexylsulfanyl]-acetyl}-mutilin+(1S,2S,5R) diastereomer (250 mg, 0.46 mmol) was treated according to the method of Example 1 Step C to obtain 14-O-{[(1R,2R,5S)-2-hydroxy-5-ethylamino-cyclohexylsulfanyl]-acetyl}-mutilin hydrochloride+(1S,2S,5R) diastereomer hydrochloride (273 mg, quant. yield uncorrected) as colorless solid.
$^1$H NMR (400 MHz, DMSO-d$_6$, δ, ppm, inter alia): 8.85 (bs, 2H, NH$_2^+$), 6.13 (2dd, 1H, 19-H, J=11 Hz and 18 Hz), 5.87 (m, 1H, NCH$_2$CHCH$_2$), 5.55 (d, 1H, 14-H, J=8 Hz), 5.47, 5.37 (2d, 2H, NCH$_2$CHCH$_2$, J=17 Hz and 10 Hz), 5.06 (m, 2H, 20-H), 4.51 (d, 1H, 11-OH, J=6 Hz), 3.72 (m, 1H, 2'-H), 3.56 (d, 2H, NCH$_2$CHCH$_2$, J=6 Hz), 3.43 (t, 1H, 11-H, J=6 Hz), 3.34 (m, 2H, 22-H), 3.13 (m, 2H, 1'-H, 5'-H), 2.40 (bs, 1H, 4-H), 1.36 (s, 3H, 15-CH$_3$), 1.06 (s, 3H, 18-CH$_3$), 0.81 (d, 3H, 17-CH$_3$, J=7 Hz), 0.63 (d, 3H, 16-CH$_3$, J=7 Hz). MS-ESI (m/z): 548 (MH$^+$), 582 (MCl$^-$).

Example 18

14-O-{[(1R,2R,5S)-2-Hydroxy-5-(2-methoxy-ethylamino)-cyclohexylsulfanyl]-acetyl}-mutilin hydrochloride+(1S,2S,5R) Diastereomer Hydrochloride Step A. N-(2-methoxy-ethyl)-N-(cyclohex-3-enyl)-carbamic acid tert-butyl ester Cyclohex-3-enyl-carbamic acid tert-butyl ester (Kampferer, P.; Vasella, A. *Helvetica Chimica Acta* 2004, 87, 2764-2789) (3 g, 15.2 mmol) and 2-bromoethyl methyl ether (1.43 ml, 15.2 mmol) were treated overnight to the method of Example 7 Step A. After work up and chromatography of the reaction mixture (silica, cyclohexane/ethyl acetate=7/1) the title compound (R$_f$=0.33, 1.2 g, 31% yield) was obtained as colorless solid.
$^1$H NMR (200 MHz, CDCl$_3$, δ, ppm): 5.61 (m, 2H, double bond), 4.10 (bs, 1H, NCH), 3.50-3.15 (m, 7H, NCH$_2$CH$_2$OCH$_3$), 2.15, 1.72 (2m, 6H), 1.47 (s, 9H, tert-butyl).

Step B. N-(2-Methoxy-ethyl)-N-(cis-3,4-epoxycyclohexyl)-carbamic acid tert-butyl ester N-(2-Methoxy-ethyl)-N-(cyclohex-3-enyl)-carbamic acid tert-butyl ester (1.2 g, 4.7 mmol) and 3-chloroperbenzoic acid (1.2 g, 70%, 4.87 mmol) were treated over the weekend according to the method of Example 7 Step B. After work up the crude title compound (silica, cyclohexane/ethyl acetate=3/1, $R_f$=0.33, 1.08 g, 85% yield) was obtained.

$^1$H NMR (200 MHz, CDCl$_3$, δ, ppm): 3.94 (bs, 1H, NCH), 3.50-3.05 (m, 9H, NCH$_2$CH$_2$OCH$_3$, epoxide), 2.30-1.20 (m, 6H), 1.45 (s, 9H, tert-butyl).

Step C. 14-O-{[(1R,2R,5S)-5-(tert-Butoxycarbonyl-(2-methoxy-ethyl)-amino)-2-hydroxy-cyclohexylsulfanyl]-acetyl}-mutilin+(1S,2S,5R) Diastereomer N-(2-Methoxy-ethyl)-N-(cis-3,4-epoxycyclohexyl)-carbamic acid tert-butyl ester (1.08 g, 4.0 mmol) was treated with pleuromutilin thiol (1.57 g, 4.0 mmol) according to the method of Example 1 Step A2. After work up and chromatography of the reaction mixture (silica, cyclohexane/ethyl acetate=1/2) 14-O-{[(1R,2R,5S)-5-(tert-Butoxycarbonyl-(2-methoxy-ethyl)-amino)-2-hydroxy-cyclohexylsulfanyl]-acetyl}-mutilin+(1S,2S,5R) diastereomer ($R_f$=0.5, 500 mg, 19% yield) was obtained as colorless solid.

$^1$H NMR (400 MHz, DMSO-d$_6$, δ, ppm, inter alia): 6.13 (2dd, 1H, 19-H, J=11 Hz and 18 Hz), 5.54 (d, 1H, 14-H, J=8 Hz), 5.05 (m, 2H, 20-H), 4.88 (d, 1H, 2'-OH, J=4 Hz), 4.48 (d, 1H, 11-OH, J=6 Hz), 3.85 (m, 1H, 5'-H), 3.68 (bs, 1H, 2'-H), 3.42 (t, 1H, 11-H, J=6 Hz), 3.35-3.05 (m, 10H, 22-H, NCH$_2$CH$_2$OCH$_3$, 1'-H), 2.40 (bs, 1H, 4-H), 1.38 (s, 9H, tert-butyl), 1.35 (s, 3H, 15-CH$_3$), 1.05 (s, 3H, 18-CH$_3$), 0.81 (d, 3H, 17-CH$_3$, J=7 Hz), 0.63 (d, 3H, 16-CH$_3$, J=7 Hz).

Step D. 14-O-{[(1R,2R,5S)-2-Hydroxy-5-(2-methoxy-ethylamino-3-cyclohexylsulfanyl]-acetyl}-mutilin+(1S,2S,5R) Diastereomer 14-O-{[(1R,2R,5S)-5-(tert-Butoxycarbonyl-(2-methoxy-ethyl)-amino)-2-hydroxy-cyclohexylsulfanyl]-acetyl}-mutilin+(1S,2S,5R) diastereomer (500 mg, 0.75 mmol) was treated according to the method of Example 1 Step B. After work up and chromatography of the reaction mixture (silica, dichloromethane/methanol/1-propanol/water/acetic acid=80/20/6/3/2) with subsequent basic extraction 14-O-{[(1R,2R,5S)-2-hydroxy-5-(2-methoxy-ethylamino)-cyclohexylsulfanyl]-acetyl}-mutilin+(1S,2S,5R) diastereomer ($R_f$=0.6, 330 mg, 78%) was obtained as colorless solid.

$^1$H NMR (500 MHz, DMSO-d$_6$, δ, ppm, inter alia): 6.14 (dd, 1H, 19-H, J=11 Hz and 18 Hz), 5.54 (d, 1H, 14-H, J=8 Hz), 5.06 (m, 2H, 20-H), 4.74 (m, 1H, 2'-OH), 4.51 (2d, 1H, 11-OH, J=6 Hz), 3.50-3.20 (m, 9H, 11-H, 2'-H, 22-H, NCH$_2$CH$_2$OCH$_3$), 2.97 (m, 1H, 1'-H), 2.63 (m, 3H, 5'-H, NCH$_2$CH$_2$OCH$_3$), 2.40 (bs, 1H, 4-H), 1.37 (s, 3H, 15-CH$_3$), 1.06 (s, 3H, 18-CH$_3$), 0.82 (d, 3H, 17-CH$_3$, J=7 Hz), 0.63 (d, 3H, 16-CH$_3$, J=7 Hz).

Step E. 14-O-{1-[(1R,2R,5S)-2-Hydroxy-5-(2-methoxy-ethylamino)-cyclohexylsulfanyl]-acetyl}-mutilin hydrochloride+(1S,2S,5R) Diastereomer Hydrochloride 14-O-{[(1R,2R,5S)-2-Hydroxy-5-(2-methoxy-ethylamino)-cyclohexylsulfanyl]-acetyl}-mutilin+(1S,2S,5R) diastereomer (330 mg, 0.58 mmol) was treated according to the method of Example 1 Step C to obtain 14-O-{[(1R,2R,5S)-2-hydroxy-5-(2-methoxy-ethylamino)-cyclohexylsulfanyl]-acetyl}-mutilin hydrochloride+(1S,2S,5R) diastereomer hydrochloride (355 mg, quant. yield, uncorrected) as colorless solid.

$^1$H NMR (400 MHz, DMSO-d$_6$, δ, ppm, inter alia): 8.65 (bs, 2H, NH$_2^+$), 6.13 (2dd, 1H, 19-H, J=11 Hz and 18 Hz), 5.55 (d, 1H, 14-H, J=8 Hz), 5.06 (m, 2H, 20-H), 4.51 (d, 1H, 11-OH, J=6 Hz), 3.71 (m, 1H, 2'-H), 3.57 (m, 5H, NCH$_2$CH$_2$OCH$_3$), 3.42 (t, 1H, 11-H, J=6 Hz), 3.33 (m, 2H, 22-H), 3.20-3.00 (m, 4H, 1'-H, 5'-H, NCH$_2$CH$_2$OCH$_3$), 2.40 (bs, 1H, 4-H), 1.36 (s, 3H, 15-CH$_3$), 1.05 (s, 3H, 18-CH$_3$), 0.81 (d, 3H, 17-CH$_3$, J=7 Hz), 0.63 (2d, 3H, 16-CH$_3$, J=7 Hz). MS-ESI (m/z): 566 (MH$^+$), 600 (MCl$^-$).

Example 19

14-O-{[(1R,2R,4R*)-2-Hydroxy-4-(2-hydroxy-ethylamino)-cyclohexylsulfanyl]-acetyl}-mutilin hydrochloride+(1S,2S,4S*) Diastereomer Hydrochloride Step A. 14-O-{[(1R,2R,4R/S)-2-(tert-Butyl-diphenyl-silanyloxy)-4-(2-hydroxy-ethylamino)-cyclohexylsulfanyl]-acetyl}-mutilin+(1S,2S,4R/S) Diastereomer To a solution of 14-O-{[(1R,2R)-2-(tert-butyl-diphenyl-silanyloxy)-4-oxo-cyclohexylsulfanyl]-acetyl}-mutilin+(1S,2S) diastereomer (1.50 g, 2.01 mmol) from Example 13 Step C in 20 ml of dichloromethane was added ethanolamine (0.12 ml, 2.01 mmol) and titanium(IV)isopropoxide (0.7 ml, 2.52 mmol) and stirred for 2 hours at room temperature. The resulting reaction mixture was treated with sodium cyanoborohydride (126 mg, 2 mmol) overnight at room temperature, diluted with further dichloromethane and extracted with NaHCO$_3$ solution. The organic layer was dried over sodium sulphate and filtered. The filtrate was subjected to chromatography (silica, dichloromethane/methanol=30/1) to yield 14-O-{[(1R,2R,4R/S)-2-(tert-butyl-diphenyl-silanyloxy)-4-(2-hydroxy-ethylamino)-cyclohexylsulfanyl]-acetyl}-mutilin+(1S,2S,4R/S) diastereomer ($R_f$=0.3, 230 mg, 14% yield).

$^1$H NMR (500 MHz, CDCl$_3$, δ, ppm, inter alia): 7.8-7.30 (m, 10H, aromat.-H), 6.47 (m, 1H, 19-H), 5.75, 5.69 (2d, 1H, 14-H, J=8 Hz), 5.40-5.15 (m, 1H, 20-H), 4.04, 3.65 (2m, 1H, 2'-H), 3.64, 3.51 (2m, 2H, NCH$_2$CH$_2$OH), 3.36 (m, 1H, 11-H), 2.74, 2.54 (2m, 2H, NCH$_2$CH$_2$OH), 2.11 (bs, 1H, 4-H), 1.44, 1.45 (2s, 3H, 15-CH$_3$), 1.17, 1.16 (s, 3H, 18-CH$_3$), 1.08 (s, 9H, Si-tert-butyl), 0.88 (2d, 3H, 17-CH$_3$), 0.75-0.65 (m, 3H, 16-CH$_3$). MS-ESI (m/z): 790 (MH$^+$), 824 (MCl$^-$).

Step B. 14-O-{[(1R,2R,4R*)-2-Hydroxy-4-(2-hydroxy-ethylamino)-cyclohexylsulfanyl]-acetyl}-mutilin+(1S,2S,4S*) Diastereomer To a solution of 14-O-{[(1R,2R,4R/S)-2-(tert-butyl-diphenyl-silanyloxy)-4-(2-hydroxy-ethylamino)-cyclohexylsulfanyl]-acetyl}-mutilin+(1S,2S,4R/S) diastereomer (230 mg, 0.29 mmol) in 15 ml of acetonitrile was treated with HF (40% aqueous, 2 drops) and stirred overnight at room temperature. The reaction was charged with NaHCO$_3$ solution and extracted with dichloromethane. The combined organic layers were dried over sodium sulfate, filtered and concentrated under reduced pressure. After chromatography (silica, dichloromethane/methanol=6/1) the title compound ($R_f$=0.4, 50 mg, 31% yield) was obtained.

$^1$H NMR (400 MHz, CDCl$_3$, δ, ppm, inter alia): 6.48 (dd, 1H, 19-H, J=11 Hz and 17 Hz), 5.76, 5.68 (2d, 1H, 14-H, J=8 Hz), 5.40-5.15 (m, 1H, 20-H), 3.66 (t, 2H, NCH$_2$CH$_2$OH, J=5 Hz), 3.50-3.15 (m, 4H, 2'-H, 1-H, 22H), 2.80 (m, 2H, NCH$_2$CH$_2$OH), 2.63 (m, 2H, 1'-H, 4'-H), 2.11 (bs, 1H, 4-H), 1.46 (s, 3H, 15-CH$_3$), 1.18 (s, 3H, 18-CH$_3$), 0.89 (d, 3H, 17-CH$_3$), 0.73 (2d, 3H, 16-CH$_3$). MS-ESI (m/z): 552 (MH$^+$).

Step C. 14-O-{[(1R,2R,4R*)-2-Hydroxy-4-(2-hydroxy-ethylamino)-cyclohexylsulfanyl]-acetyl}-mutilin hydrochloride+(1S,2S,4S*) Diastereomer Hydrochloride 14-O-{[(1R,2R,4R*)-2-Hydroxy-4-(2-hydroxy-ethylamino)-cyclohexylsulfanyl]-acetyl}-mutilin+(1S,2S,4S*) diastereomer (50 mg, 0.091 mmol) was treated according to the method of Example 1 Step C to obtain 14-O-{[(1R,2R,4R*)-2-Hydroxy-4-(2-hydroxy-ethylamino)-cyclohexylsulfanyl]-acetyl}-mutilin hydrochloride+(1S,2S,4S*) diastereomer hydrochloride (43 mg, 80% yield) as colorless solid.

$^1$H NMR (500 MHz, CDCl$_3$, δ, ppm, inter alia): 6.46 (dd, 1H, 19-H, J=11 Hz and 17 Hz), 5.76 (d, 1H, 14-H, J=8 Hz), 5.37 (d, 1H, 20-H, J=11 Hz), 5.23 (d, 1H, 20-H, J=17 Hz), 3.95 (m, 2H, NCH$_2$CH$_2$OH, J=5 Hz), 3.58 (m, 1H, 2'-H), 3.40-3.10 (m, 5H, 11-H, 22H, NCH$_2$CH$_2$OH), 2.72 (m, 1H, 1'-H), 2.11 (bs, 1H, 4-H), 1.46 (s, 3H, 15-CH$_3$), 1.18 (s, 3H, 18-CH$_3$), 0.89 (d, 3H, 17-CH$_3$, J=7 Hz), 0.73 (d, 3H, 16-CH$_3$, J=7 Hz). MS-ESI (m/z): 552 (MH$^+$), 586 (MCl$^-$).

Example 20

14-O-{1-[(1R,2R,4R*)-4-Cyclohexylamino-2-hydroxy-cyclohexylsulfanyl]-acetyl}-mutilin hydrochloride+(1S,2S,4S*) Diastereomer Hydrochloride Step A. 14-O-{[(1R,2R,4R*)-2-(tert-Butyl-diphenyl-silanyloxy)-4-(2-hydroxy-ethylamino)-cyclohexylsulfanyl]-acetyl}-mutilin+(1S,2S,4S*) Diastereomer 14-O-{[(1R,2R)-2-(tert-butyl-diphenyl-silanyloxy)-4-oxo-cyclohexylsulfanyl]-acetyl}-mutilin+(1S,2S) diastereomer (1.50 g, 2.01 mmol) from Example 13 Step C was reacted with cyclohexylamine (0.23 ml, 1.01 mmol) according to the method of Example 19 Step A. After work up and chromatography of the reaction mixture (silica, dichloromethane/methanol=30/1) 14-O-{[(1R,2R,4R*)-2-(tert-butyl-diphenyl-silanyloxy)-4-cyclohexylamino-cyclohexylsulfanyl]-acetyl}-mutilin+(1S,2S,4S*) diastereomer (R$_f$=0.13, 150 mg, 9% yield) was obtained.

$^1$H NMR (500 MHz, CDCl$_3$, δ, ppm, inter alia): 7.8-7.3 (m, 10H, aromat.-H), 6.48 (dd, 1H, 19-H, J=11 Hz and 17 Hz), 5.76 (d, 11H, 14-H, J=8 Hz), 5.40-5.15 (m, 1H, 20-H), 3.62 (m, 1H, 2'-H), 3.40-3.10 (m, 3H, 11-H, 22-H), 2.77 (m, 1H, 1'-H), 2.11 (bs, 1H, 4-H), 1.46 (s, 3H, 15-CH$_3$), 1.16 (s, 3H, 18-CH$_3$), 1.07 (s, 9H, Si-tert-butyl), 0.88 (2d, 3H, 17-CH$_3$), 0.74, 0.73 (2d, 3H, 16-CH$_3$). MS-ESI (m/z): 828 (MH$^+$), 862 (MCl$^-$).

Step B. 14-O-{[(1R,2R,4R*)-4-Cyclohexyl-2-hydroxy-cyclohexylsulfanyl]-acetyl}-mutilin+(1S,2S,4S*) Diastereomer 14-O-{[(1R,2R,4R*)-2-(tert-butyl-diphenyl-silanyloxy)-4-cyclohexylamino-cyclohexylsulfanyl]-acetyl}-mutilin+(1S,2S,4S*) diastereomer (100 mg, 0.121 mmol) was treated with HF (40% aqueous, 30 drops) for 5 hours according to the method of Example 19 Step B. After work up and chromatography of the reaction mixture (silica, dichloromethane/methanol=10/1) the title compound (R$_f$=0.13, 23 mg, 32% yield) was obtained.

$^1$H NMR (500 MHz, CDCl$_3$, δ, ppm, inter alia): 6.46 (dd, 1H, 19-H, J=11 Hz and 17 Hz), 5.75 (m, 1H, 14-H), 5.40-5.15 (m, 1H, 20-H), 3.49 (m, 1H, 2'-H), 3.35 (m, 1H, 11-H), AB-system (v$_A$=3.30, v$_B$=3.20, 22-H, J=15 Hz), 3.01 (m, 1H, 4'-H), 2.67 (m, 1H, 1'-H), 2.09 (bs, 1H, 4-H), 1.45 (s, 3H, 15-CH$_3$), 1.16 (s, 3H, 18-CH$_3$), 0.87 (d, 3H, 17-CH$_3$, J=7 Hz), 0.72 (d, 3H, 16-CH$_3$, J=7 Hz). MS-ESI (m/z): 591 (MH$^+$).

Step C. 14-O-{1-[(1R,2R,4R*)-4-Cyclohexyl-2-hydroxy-cyclohexylsulfanyl]-acetyl}-mutilin hydrochloride+(1S,2S,4S*) Diastereomer Hydrochloride 14-O-{[(1R,2R,4R*)-4-Cyclohexyl-2-hydroxy-cyclohexylsulfanyl]-acetyl}-mutilin+(1S,2S,4S*) diastereomer (23 mg, 0.039 mmol) was treated according to the method of Example 1 Step C to obtain 14-O-{[(1R,2R,4R*)-4-Cyclohexyl-2-hydroxy-cyclohexylsulfanyl]acetyl}-mutilin hydrochloride+(1S,2S,4S*) diastereomer hydrochloride (26 mg, quantitative yield, uncorrected) as colorless solid.

$^1$H NMR (500 MHz, CDCl$_3$, δ, ppm, inter alia): 9.3 (bs, 2H, NH$_2$$^+$), 6.46 (dd, 1H, 19-H, J=11 Hz and 17 Hz), 5.75 (d, 1H, 14-H, J=8 Hz), 5.38 (d, 1H, 20-H, J=12 Hz), 5.22 (d, 1H, 20-H, J=17 Hz), 3.50-3.00 (m, 6H, 2'-H, 1-H, 22H, NcHex), 2.65 (m, 2H, 1'-H, 3a'-H), 2.10 (bs, 1H, 4-H), 1.45 (s, 3H, 15-CH$_3$), 1.18 (s, 3H, 18-CH$_3$), 0.88 (d, 3H, 17-CH$_3$, J=7 Hz), 0.73 (d, 3H, 16-CH$_3$, J=7 Hz). MS-ESI (m/z): 591 (MH$^+$), 624 (MCl$^-$).

Example 21

14-O-{[(1R,2R,4R*)-4-Cyclopropylamino-2-hydroxy-cyclohexylsulfanyl]-acetyl}-mutilin+(1S,2S,4S*) Diastereomer Step A. 14-O-{[(1R,2R,4R*)-2-(tert-Butyl-diphenyl-silanyloxy)-4-cyclopropylamino-cyclohexylsulfanyl]-acetyl}-mutilin+(1S,2S,4S*) Diastereomer 14-O-{[(1R,2R)-2-(tert-butyl-diphenyl-silanyloxy)-4-oxo-cyclohexylsulfanyl]-acetyl}-mutilin+(1S,2S) diastereomer (750 mg, 1.01 mmol) from Example 13 Step C was reacted with cyclopropylamine (0.07 ml, 1.01 mmol) in 40 ml of dichloromethane according to the method of Example 19 Step A. After the treatment of sodium cyanoborohydride ethanol was added (0.7 ml) and the mixture was stirred overnight at room temperature. After work up and chromatography of the reaction mixture (silica, dichloromethane/methanol=30/1) 14-O-{[(1R,2R,4R*)-2-(tert-butyl-diphenyl-silanyloxy)-4-cyclopropylamino-cyclohexylsulfanyl]-acetyl}-mutilin+(1S,2S,4S*) diastereomer (R$_f$=0.35, 283 mg, 36% yield) was obtained.

$^1$H NMR (500 MHz, DMSO-d$_6$, δ, ppm, inter alia): 7.65-7.35 (m, 10H, aromat.-H), 6.12 (m, 1H, 19-H), 5.5.2, 5.51 (2d, 1H, 14-H, J=8 Hz), 5.00 (m, 1H, 20-H), 4.50 (t, 1H, 11-OH, J=5.5 Hz), 3.94 (m, 1H, 2'-H), 3.41 (m, 1H, 11-H), 3.05-2.80 (m, 4H, 22-H, 1'-H, 4'-H), 2.39 (bs, 1H, 4-H), 1.86 (m, 1H, cPr), 1.33 (2s, 3H, 15-CH$_3$), 1.12 (s, 12H, 18-CH$_3$, Si-tert-butyl), 0.81 (d, 3H, 17-CH$_3$, J=7 Hz), 0.57, 0.56 (2d, 3H, 16-CH$_3$, J=7 Hz), 0.25, 0.06 (2m, 4H, cPr). MS-ESI (m/z): 786 (MH$^+$), 784 (M-H)$^-$.

Step B. 14-O-{[(1R,2R,4R*)-4-Cyclopropylamino-2-hydroxy-cyclohexylsulfanyl]-acetyl}-mutilin+(1S,2S,4S*) Diastereomer 14-O-{[(1R,2R,4R*)-2-(tert-butyl-diphenyl-silanyloxy)-4-cyclopropyl-amino-cyclohexylsulfanyl]-acetyl}-mutilin+(1S,2S,4S*) diastereomer (223 mg, 0.284 mmol) was treated overnight with tetrabutylammonium fluoride according to the method of Example 13 Step G. After work up and chromatography of the reaction mixture (silica, dichloromethane/methanol=10/1) the title compound ($R_f$=0.2, 10 mg, 6% yield) was obtained.

$^1$H NMR (500 MHz, DMSO-$d_6$, δ, ppm, inter alia): 6.13 (dd, 1H, 19-H, J=11 Hz and 17 Hz), 5.50 (d, 1H, 14-H, J=7 Hz), 5.05 (m, 1H, 20-H), 4.87 (m, 1H, 2'-OH), 4.50 (d, 1H, 11-OH, J=6 Hz), 3.55-3.20 (m, 4H, 22-H, 2'-H, 1'-H), 2.50 (m, 2H, 1'-H, 4'-H), 2.40 (bs, 1H, 4-H), 2.01 (m, 1H, cPr), 1.35 (s, 3H, 15-CH$_3$), 1.04 (s, 3H, 18-CH$_3$), 0.81 (d, 3H, 17-CH$_3$, J=7 Hz), 0.62 (d, 3H, 16-CH$_3$, J=−6 Hz), 0.32, 0.15 (2m, 4H, cPr). MS-ESI (m/z): 548 (MH$^+$), 1095 (2 MH$^+$), 1117 (2MNa$^+$), 582 (MCl$^-$).

Example 22

14-O-{[(1R,2R,5S*)-4-Cyclopropylamino-2-hydroxy-cyclohexylsulfanyl]-acetyl}-mutilin hydrochloride+(1S,2S,5R*) Diastereomer Hydrochloride Step A. 14-O-{[(1R,2R)-2-Hydroxy-4-oxo-cyclohexylsulfanyl]-acetyl}-mutilin+(1S,2S) Diastereomer and 14-O-{[(1R,2R)-2-Hydroxy-5-oxo-cyclohexylsulfanyl]-acetyl}-mutilin+(1S,2S) Diastereomer 14-O-{[(7R,8R)-7-hydroxy-1,4-dioxa-spiro[4.5]dec-8-ylsulfanyl]-acetyl}-mutilin+(7S,8S) diastereomer as well as 14-O-{[(7R,8R)-8-hydroxy-1,4-dioxa-spiro[4.5]dec-7-ylsulfanyl]-acetyl}-mutilin+(7S,8S) diastereomer (3.96 g, 7.19 mmol) was dissolved in 50 ml of dioxane and treated with 4N HCl (5 ml, 20 mmol) for 6 hours at room temperature. The reaction mixture was concentrated under reduced pressure, charged with NaHCO$_3$ solution and extracted tree times with ethyl acetate. The organic layers were dried over sodium sulphate and filtered. The filtrate was concentrated under reduced pressure and subjected to chromatography (silica, cyclohexane/dioxane=2/1) to yield a mixture of the title compounds ($R_f$=0.30, 860 mg, 24% yield).

$^1$H NMR (500 MHz, DMSO-$d_6$, δ, ppm, inter alia): 6.13 (m, 1H, 19-H), 5.56, 5.54 (2d, 1H, 14-H, J=8 Hz), 5.38, 5.32 (2m, 1H, 2'-OH), 5.05 (m, 2H, 20-H), 4.50 (d, 1H, 11-OH, J=5 Hz), 3.95, 3.83 (2m, 1H, 2'-H), 3.50-3.20 (m, 3H, 11-H, 22-H), 3.17, 3.07 (2m, 1H, 1'-H), 2.40 (bs, 1H, 4-H), 1.35, 1.33 (2s, 3H, 15-CH$_3$), 1.05 (s, 3H, 18-CH$_3$), 0.81 (d, 3H, 17-CH$_3$, J=7 Hz), 0.63, 0.62 (2d, 3H, 16-CH$_3$). 529 (MNa$^+$), 505 (M-H)$^-$.

Step B. 14-O-{[(1R,2R,5S*)-5-Cyclopropylamino-2-hydroxy-cyclohexylsulfanyl]-acetyl}-mutilin+(1S,2S,4R*) Diastereomer and 14-O-{[(1R,2R,4S*)-4-Cyclopropylamino-2-hydroxy-cyclohexylsulfanyl]-acetyl}-mutilin+(1S,2S,4R*) Diastereomer 14-O-{[(1R,2R)-2-Hydroxy-4-oxo-cyclohexylsulfanyl]-acetyl}-mutilin+(1S,2S) diastereomer and 14-O-{[(1R,2R)-2-hydroxy-5-oxo-cyclohexylsulfanyl]-acetyl}-mutilin+(1S,2S) diastereomer (250 mg, 0.493 mmol) was reacted with cyclopropylamine (0.03 ml, 0.493 mmol) in 15 ml of dichloromethane according to the method of Example 19 Step A. After the treatment of sodium cyanoborohydride ethanol was added (0.7 ml) and the mixture was stirred overnight at room temperature. After work up and chromatography of the reaction mixture (silica, dichloromethane/methanol=20/1) 14-O-{[(1R,2R,5S*)-4-cyclopropylamino-2-hydroxy-cyclohexylsulfanyl]-acetyl}-mutilin+(1S,2S,5R*) diastereomer (a) (dichloromethane/methanol=10/1, $R_f$=0.22, 34 mg, 13% yield) and 14-O-{[(1R,2R,4S*)-4-cyclopropylamino-2-hydroxy-cyclohexylsulfanyl]-acetyl}-mutilin+(1S,2S,4R*) diastereomer (b) (dichloromethane/methanol=10/1, $R_f$=0.13, 26 mg, 4% yield) were obtained.

(a): $^1$H NMR (500 MHz, DMSO-$d_6$, δ, ppm, inter alia): 6.13 (m, 1H, 19-H, J=11 and 18 Hz), 5.53 (d, 1H, 14-H, J=8 Hz), 5.06 (m, 1H, 20-H), 4.67 (t, 1H, 2'-OH), 4.47 (d, 1H, 11-OH, J=6 Hz), 3.50-3.20 (m, 4H, 11-H, 2'-H, 22-H), 2.92 (m, 1H, 1'-H), 2.71 (m, 1H, 5'-H), 2.39 (bs, 1H, 4-H), 1.96 (m, 1H, cPr), 1.36 (s, 3H, 15-CH$_3$), 1-0.05 (s, 3H, 18-CH$_3$), 0.81 (d, 3H, 17-CH$_3$, J=7 Hz), 0.62 (d, 3H, 16-CH$_3$, J=7 Hz), 0.32, 0.16 (2m, 4H, cPr). MS-ESI (m/z): 548 (MH$^+$), 546 (M-H)$^-$.

(b): $^1$H NMR (500 MHz, DMSO-$d_6$, δ, ppm, inter alia): 6.13 (m, 1H, 19-H, J=11 and 18 Hz), 5.54 (d, 1H, 14-H, J=8 Hz), 5.05 (m, 1H, 20-H), 4.70 (d, 1H, 2'-OH; J=5 Hz), 4.47 (d, 1H, 11-OH, J=6 Hz), 3.68 (m, 1H, 2'-H), 3.45-3.15 (m, 3H, 11-H, 22-H), 2.86 (m, 1H, 4'-H), 2.71 (m, 1H, 1'-H), 2.39 (bs, 1H, 4-H), 1.96 (m, 1H, cPr), 1.35 (s, 3H, 15-CH$_3$), 1.05 (s, 3H, 18-CH$_3$), 0.81 (d, 3H, 17-CH$_3$, J=7 Hz), 0.62 (d, 3H, 16-CH$_3$, J=7 Hz), 0.32, 0.15 (2m, 4H, cPr). MS-ESI (m/z): 548 (MH$^+$), 546 (M-H)$^-$.

Step C. 14-O-{[(1R,2R,5S*)-5-Cyclopropylamino-2-hydroxy-cyclohexylsulfanyl]-acetyl}-mutilin hydrochloride+(1S,2S,5R*) Diastereomer Hydrochloride 14-O-{[(1R,2R,5S*)-4-Cyclopropylamino-2-hydroxy-cyclohexylsulfanyl]-acetyl}-mutilin+(1S,2S,5R*) diastereomer (34 mg, 0.062 mmol) was treated according to the method of Example 1 Step C to obtain 14-O-{[(1R,2R,5R*)-4-Cyclopropylamino-2-hydroxy-cyclohexylsulfanyl]-acetyl}-mutilin hydrochloride+(1S,2S,5S*) diastereomer hydrochloride (24 mg, 66% yield) as colorless solid.

$^1$H NMR (500 MHz, DMSO-$d_6$, δ, ppm, inter alia): 6.13 (m, 1H, 19-H, J=11 and 18 Hz), 5.55 (d, 1H, 14-H, J=8 Hz), 5.05 (m, 1H, 20-H), 5.00 (m, 1H, 2'-OH), 4.54 (d, 1H, 11-OH, J=6 Hz), 3.66 (m, 1H, 2'-H), 3.45-3.05 (m, 5H, 11-H, 22-H, 1'-H, 5'-H), 2.41 (bs, 1H, 4-H), 1.36 (s, 3H, 15-CH$_3$), 1.06 (s, 3H, 18-CH$_3$), 0.82 (d, 3H, 17-CH$_3$, J=7 Hz), 0.63 (m, 7H, 16-CH$_3$, cPr). MS-ESI (m/z): 548 (MH$^+$), 582 (MCl$^-$).

Example 23

14-O-{[(1R,2R,4S*)-4-Cyclopropylamino-2-hydroxy-cyclohexylsulfanyl]-acetyl}-mutilin hydrochloride+(1S,2S,4R*) Diastereomer Hydrochloride 14-O-{[(1R,2R,4S*)-4-Cyclopropylamino-2-hydroxy-cyclohexylsulfanyl]-acetyl}-mutilin+(1S,2S,4R*) diastereomer (10 mg, 0.018 mmol) from Example 21 Step B was treated according to the method of Example 1 Step C to obtain the title compound (20 mg, quantitative yield, uncorrected) as colorless solid.

$^1$H NMR (500 MHz, DMSO-$d_6$, δ, ppm, inter alia): 8.6 (bs, 2H, NH$_2^+$), 6.13 (m, 1H, 19-H, J=11 and 18 Hz), 5.55 (d, 1H, 14-H, J=8 Hz), 5.26 (m, 1H, 2'-OH), 5.05 (m, 1H, 20-H), 4.52 (d, 1H, 11-OH, J=6 Hz), 3.93 (m, 1H, 2'-H), 3.45-3.20 (m, 4H, 11-H, 22-H, 4'-H), 2.95 (m, 1H, 11'-H), 2.64 (m, 1H, cPr), 2.40 (bs, 1H, 4-H), 1.36 (s, 3H, 15-CH$_3$), 1.05 (s, 3H, 18-CH$_3$), 0.81 (d, 3H, 17-CH$_3$, J=7 Hz), 0.74 (m, 4H, cPr), 0.62 (d, 3H, 16-CH$_3$, J=7 Hz). MS-ESI (m/z): 548 (MH$^+$), 582 (MCl$^-$).

Example 24

**14-O-{[(1R,2R,5R*)-2-Hydroxy-5-morpholin-4-yl-cyclohexylsulfanyl]-acetyl}-mutilin hydrochloride+ (1S,2S,5S*) Diastereomer Hydrochloride**

Step A. 14-O-{[(1R,2R,5R*)-2-Hydroxy-5-morpholin-4-yl-cyclohexylsulfanyl]-acetyl}-mutilin+(1S,2S, 5S*) Diastereomer and 14-O-{[(1R,2R,5S*)-2-Hydroxy-5-morpholin-4-yl-cyclohexylsulfanyl]-acetyl}-mutilin+(1S,2S,5R*) Diastereomer 14-O-{[(1R,2R)-2-Hydroxy-4-oxo-cyclohexylsulfanyl]-acetyl}-mutilin+(1S,2S) diastereomer and 14-O-{[(1R,2R)-2-hydroxy-5-oxo-cyclohexylsulfanyl]-acetyl}-mutilin+(1S, 2S) diastereomer (270 mg, 0.533 mmol) from Example 22 Step A was reacted with morpholine (0.05 ml, 0.533 mmol) in 10 ml of dichloromethane according to the method of Example 19 Step A. After addition of sodium cyanoborohydride ethanol was added (0.6 ml) and the mixture was stirred overnight at room temperature. After work up and chromatography of the reaction mixture (silica, dichloromethane/methanol=20/1) 14-O-{[(1R,2R,5R*)-2-Hydroxy-5-morpholin-4-yl-cyclohexylsulfanyl]-acetyl}-mutilin+(1S,2S, 5S*) diastereomer (a) (dichloromethane/methanol=10/1, $R_f$=0.32, 23 mg, 7% yield) and 14-O-{[(1R,2R,5S*)-2-Hydroxy-5-morpholin-4-yl-cyclohexylsulfanyl]-acetyl}-mutilin+(1S,2S,5R*) diastereomer (b) (dichloromethane/methanol=10/1, $R_f$=0.27, 40 mg, 13% yield) were obtained.

(a): $^1$H NMR (500 MHz, CDCl$_3$, δ, ppm, inter alia): 6.47 (m, 1H, 19-H), 5.77, 5.75 (2d, 1H, 14-H, J=8 Hz), 5.35 (dd, 11H, 20-H, J=3 and 11 Hz), 5.21 (d, 1H, 20-H, J=17 Hz), 3.70 (s, 4H, morpholine), 3.40-3.15 (m, 4H, 2'-H, 11-H, 22H), 2.53 (m, 5H, 1'-H, morpholine), 2.10 (bs, 1H, 4-H), 1.45 (s, 3H, 15-CH$_3$), 1.17 (s, 3H, 18-CH$_3$), 0.87 (d, 3H, 17-CH$_3$, J=7 Hz), 0.73, 0.72 (2d, 3H, 16-CH$_3$, J=7 Hz). MS-ESI (m/z): 578 (MH$^+$), 600 (MNa$^+$), 576 (M-H)$^-$, 612 (MCl$^-$).

(b): $^1$H NMR (500 MHz, CDCl$_3$, δ, ppm, inter alia): 6.47 (m, 11H, 19-H), 5.77, 5.75 (2d, 1H, 14-H, J=8 Hz), 5.40-5.15 (m, 2H, 20-H), 3.70 (s, 4H, morpholine), 3.47 (m, 1H, 2'-H), 3.35 (m, 1H, 11-H), 3.22 (m, 2H, 22-H), 2.98 (m, 1H, 1'-H), 2.54, 2.45 (2m, 4H, morpholine), 2.10 (bs, 1H, 4-H), 1.45 (s, 3H, 15-CH$_3$), 1.17 (s, 3H, 18-CH$_3$), 0.88 (d, 3H, 17-CH$_3$, J=6 Hz), 0.72 (d, 3H, 16-CH$_3$, J=7 Hz). MS-ESI (m/z): 578 (MH$^+$), 600 (MNa$^+$), 576 (M-H)$^-$, 612 (MCl$^-$).

Step B. 14-O-{[(1R,2R,5R*)-2-Hydroxy-5-morpholin-4-yl-cyclohexylsulfanyl]-acetyl}-mutilin hydrochloride+(1S,2S,5S*) Diastereomer Hydrochloride 14-O-{[(1R,2R,5R*)-2-Hydroxy-5-morpholin-4-yl-cyclohexylsulfanyl]-acetyl}-mutilin+(1S,2S,5S*) diastereomer (10 mg, 0.017 mmol) was treated according to the method of Example 1 Step C to obtain 14-O-{[(1R,2R,5R*)-2-Hydroxy-5-morpholin-4-yl-cyclohexylsulfanyl]-acetyl}-mutilin hydrochloride+(1S,2S,5S*) diastereomer hydrochloride (20 mg, quantitative yield, uncorrected) as colorless solid.

$^1$H NMR (500 MHz, CDCl$_3$, δ, ppm, inter alia): 13 (bs, 11H, NH$^+$), 6.47 (m, 11H, 19-H), 5.78, 5.76 (2d, 11H, 14-H, J=9 Hz), 5.36 (dd, 11H, 20-H, J=4 and 11 Hz), 5.23 (d, 11H, 20-H; J=17 Hz), 4.40, 3.98 (2bs, 4H, morpholine), 3.45-3.20 (m, 4H, 2'-H, 11-H, 22-H), 2.91, 2.56 (2m, 5H, morpholine, 1'-H), 2.11 (bs, 11H, 4-H), 1.46 (s, 3H, 15-CH$_3$), 1.20, 1.19 (2s, 3H, 18-CH$_3$), 0.89 (d, 3H, 17-CH$_3$, J=7 Hz), 0.74, 0.73 (2d, 3H, 16-CH$_3$, J=7 Hz). MS-ESI (m/z): 578 (MH$^+$), 600 (MNa$^+$), 612 (MCl$^-$).

Example 25

**14-O-{[(1R,2R,5S*)-2-Hydroxy-5-morpholin-4-yl-cyclohexylsulfanyl]-acetyl}-mutilin hydrochloride+ (1S,2S,5R*) Diastereomer Hydrochloride**

14-O-{[(1R,2R,5S*)-2-Hydroxy-5-morpholin-4-yl-cyclohexylsulfanyl]acetyl}-mutilin+(1S,2S,5R*) diastereomer (26 mg, 0.045 mmol) from Example 24 Step A was treated according to the method of Example 1 Step C to obtain the title compound (15 mg, 54% yield) as colorless solid.

$^1$H NMR (500 MHz, CDCl$_3$, δ, ppm, inter alia): 12.8 (bs, 1H, NH$^+$), 6.47 (m, 1H, 19-H), 5.75 (m, 1H, 14-H), 5.40-5.15 (m, 2H, 20-H), 4.40, 3.98 (2bs, 4H, morpholine, 2'-H), 3.50-3.15 (m, 6H, 5'-H, 11-H, 22-H, morpholine), 2.98 (m, 2H, morpholine), 2.11 (bs, 1H, 4-H), 1.46 (s, 3H, 15-CH$_3$), 1.19 (s, 3H, 18-CH$_3$), 0.89 (d, 3H, 17-CH$_3$, J=7 Hz), 0.74 (d, 3H, 16-CH$_3$, J=7 Hz). MS-ESI (m/z): 578 (MH$^+$), 606 (MNa$^+$), 612 (MCl$^-$).

Example 26

14-O-{[(1R,2R,5S)-5-Amino-2'-hydroxy-cyclohexylsulfanyl]-acetyl}-19,20-dihydro-mutilin hydrochloride+(1S,2S,5R) Diastereomer Hydrochloride

Step A. 14-O-{[(1R,2R,5S)-5-tert-Butoxycarbonylamino-2-hydroxy-cyclohexylsulfanyl]-acetyl}-19, 20-dihydro-mutilin+(1S,2S,5R) Diastereomer To a solution of 14-O-{[(1R,2R,5S)-5-tert-butoxycarbonylamino-2-hydroxy-cyclohexylsulfanyl]-acetyl}-mutilin+ (1S,2S,5R) diastereomer (1 g, 1.65 mmol) from Example 1 Step A in 20 ml of ethanol was added palladium on charcoal (10%, 515 mg, 0.48 mmol) and hydrogenated overnight at room temperature. The reaction mixture was treated with dichloromethane, filtered and the filtrate was concentrated to dryness under reduced pressure to obtain 14-O-{[(1R,2R, 5S)-5-tert-butoxycarbonylamino-2-hydroxy-cyclohexylsulfanyl]-acetyl}-19,20-dihydro-mutilin+(1S,2S,5R) diastereomer (1 g, quantitative yield) as colorless solid.

MS-ESI (m/z): 632 (MNa$^+$).

Step B. 14-O-{[(1R,2R,5S)-5-Amino-2-hydroxy-cyclohexylsulfanyl]-acetyl}-19,20-dihydro-mutilin+ (1S,2S,5R) Diastereomer 14-O-{[(1R,2R,5S)-5-tert-butoxycarbonylamino-2-hydroxy-cyclohexylsulfanyl]-acetyl}-19,20-dihydro-mutilin+ (1S,2S,5R) diastereomer (1 g, 1.64 mmol) was treated according to the method of Example 1 Step B. After work up and chromatography of the reaction mixture (silica, ethyl acetate/methanol/35% ammonia solution=33/66/1) 14-O-{[(1R,2R,5S)-5-amino-2-hydroxy-cyclohexylsulfanyl]-acetyl}-19,20-dihydro-mutilin+(1S,2 S,5R) diastereomer ($R_f$=0.35, 590 mg, 71% yield) was obtained as colorless solid.

$^1$H NMR (400 MHz, DMSO-d$_6$, δ, ppm, inter alia): 5.51 (d, 1H, 14-H, J=8 Hz), 4.74 (bs, 1H, 2'-OH), 4.37 (m, 1H, 11-OH), 3.49 (m, 1H, 2'-H), 3.45-3.15 (m, 3H, 11-H, 22-H), 3.00 (m, 1H, 1'-H), 2.82 (m, 1H, 5'-H), 2.35 (bs, 1H, 4-H), 1.34 (s, 3H, 15-CH$_3$), 0.85 (s, 3H, 18-CH$_3$), 0.80 (d, 3H, 17-CH$_3$, J=7 Hz), 0.63 (m, 6H, 16-CH$_3$, 20-H).

Step C. 14-O-{[(1R,2R,5S)-5-Amino-2-hydroxy-cyclohexylsulfanyl]-acetyl}-19,20-dihydro-mutilin hydrochloride+(1S,2S,5R) Diastereomer Hydrochloride 14-O-{[(1R,2R,5S)-5-Amino-2-hydroxy-cyclohexylsulfanyl]-acetyl}-19,20-dihydro-mutilin+(1S,2S,5R) diastereomer (590 mg, 1.16 mmol) was treated according to the method of Example 1 Step C to obtain 14-O-{[(1R,2R,5S)-5-amino-2-hydroxy-cyclohexylsulfanyl]-acetyl}-19,20-dihydro-mutilin hydrochloride+(1S,2S,5R) diastereomer hydrochloride (566 mg, 89% yield) as colorless solid.

$^1$H NMR (500 MHz, DMSO-d$_6$, δ, ppm, inter alia): 7.9 (bs, 3H, NH$_3^+$), 5.52 (d, 1H, 14-H, J=8 Hz), 3.80-3.00 (m, 6H, 2'-H, 11-H, 22-H, 1'-H, 5'-H), 2.35 (bs, 1H, 4-H), 1.35 (s, 3H, 15-CH$_3$), 0.85 (s, 3H, 18-CH$_3$), 0.80 (d, 3H, 17-CH$_3$, J=7 Hz), 0.63 (m, 6H, 16-CH$_3$, 20-H). MS-ESI (m/z): 510 (MH$^+$), 544 (MCl$^-$).

Example 27

14-O-{[(1R,2R,5S)-5-Ethylamino-2-hydroxy-cyclohexylsulfanyl]-acetyl}-19,20-dihydro-mutilin hydrochloride+(1S,2S,5R) Diastereomer Hydrochloride

Step A. 19,20-Dihydro-pleuromutilin thiol

A solution of 19,20-dihydro-pleuromutilin tosylate (Egger, H.; Reinshagen, H. *Journal of Antibiotics* 1976, 29, 915-927.) (11.5 g, 22.2 mmol) in 50 ml of acetone was treated with thiourea (1.69 g, 22.2 mmol) under reflux for 1.5 hours. The reaction mixture was evaporated to dryness under reduced pressure and dissolved in ethanol. The solution was charged with sodium metabisulfite (4.57 g, 24.0 mmol) dissolved in 20 ml of water, and 100 ml of ethyl acetate. The biphasic mixture was refluxed for 1.5 hours under vigorous stirring. After cooling to room temperature the phases were seperated and the aqueous phase was extracted three times with ethyl acetate. The combined organic layers were dried over sodium sulfate, filtered and the solvent evaporated under reduced pressure. After chromatography (silica, cyclohexane/ethyl acetate=2/1) 19,20-dihydro-pleuromutilin thiol (cyclohexane/ethyl acetate=4/3, R$_f$=0.24, 3 g, 34% yield) were obtained.

$^1$H NMR (500 MHz, DMSO-d$_6$, δ, ppm, inter alia): 5.53 (d, 1H, 14-H, J=8 Hz), 4.40 (d, 1H, 11-OH, J=6 Hz), 3.36 (t, 1H, 11-H, J=6 Hz), 3.25 (m, 2H, 22-H), 2.85 (t, 1H, SH, J=8 Hz), 2.38 (bs, 1H, 4-H), 1.37 (s, 3H, 15-CH$_3$), 0.87 (s, 3H, 18-CH$_3$), 0.83 (d, 3H, 17-CH$_3$, J=7 Hz), 0.65 (m, 6H, 16-CH$_3$, 20-H).

Step B. 14-O-{[(1R,2R,5S)-5-(tert-Butoxycarbonyl-ethyl-amino)-2-hydroxy-cyclohexylsulfanyl]-acetyl}-19,20-dihydro-mutilin+(1S,2S,5R) Diastereomer N-Ethyl-N-(cis-3,4-epoxycyclohexyl)-carbamic acid tert-butyl ester (2.8 g, 11.6 mmol) from Example 7 Step B was treated with 19,20-dihydro-pleuromutilin thiol (4.60 g, 11.6 mmol) according to the method of Example 1 Step A3 over the weekend at room temperature. After work up and chromatography of the reaction mixture (silica, cyclohexane/ethyl acetate=1/1) 14-O-{[(1R,2R,5S)-5-(tert-Butoxycarbonyl-ethyl-amino)-2-hydroxy-cyclohexylsulfanyl]-acetyl}-19,20-dihydro-mutilin+(1S,2S,5R) diastereomer (R$_f$=0.35, 1.98 g, 27% yield) was obtained.

Step C. 14-O-{[(1R,2R,5S)-5-Ethylamino-2-hydroxy-cyclohexylsulfanyl]-acetyl}-19,20-dihydro-mutilin+(1S,2S,5R) Diastereomer 14-O-{[(1R,2R,5S)-5-(tert-Butoxycarbonyl-ethyl-amino)-2-hydroxy-cyclohexylsulfanyl]-acetyl}-19,20-dihydro-mutilin+(1S,2S,5R) diastereomer (1.98 g, 3.10 mmol) was treated according to the method of Example 1 Step B. After work up and chromatography of the reaction mixture (silica, ethyl acetate/methanol/35% ammonia solution=100/10/1) 14-O-{[(1R,2R,5S)-5-ethylamino-2-hydroxy-cyclohexylsulfanyl]-acetyl}-19,20-dihydro-mutilin+(1S,2S,5R) diastereomer (ethyl acetate/methanol/35% ammonia solution=100/100/1, R$_f$=0.7, 150 mg, 9% yield) was obtained as colorless solid.

$^1$H NMR (400 MHz, DMSO-d$_6$, δ, ppm, inter alia): 5.52 (d, 1H, 14-H, J=7 Hz), 4.72 (m, 1H, 2'-OH), 4.36 (d, 1H, 11-OH, J=6 Hz), 3.50-3.15 (m, 4H, 2'-H, 11-H, 22-H), 2.97 (m, 1H, 1'-H), 2.62 (m, 1H, 5'-H), 2.47 (m, 2H, NCH$_2$), 2.35 (bs, 1H, 4-H), 1.35 (s, 3H, 15-CH$_3$), 0.98 (m, 3H, NCH$_2$CH$_3$), 0.85 (s, 3H, 18-CH$_3$), 0.80 (d, 3H, 17-CH$_3$, J=7 Hz), 0.63 (m, 6H, 16-CH$_3$, 20-H). MS-ESI (m/z): 538 (MH$^+$), 560 (MNa$^+$), 536 (M-H)$^-$, 572 (MCl$^-$).

Step D. 14-O-{[(1R,2R,5S)-5-Ethylamino-2-hydroxy-cyclohexylsulfanyl]-acetyl}-19,20-dihydro-mutilin hydrochloride+(1S,2S,5R) Diastereomer Hydrochloride 14-O-{[(1R,2R,5S)-5-Ethylamino-2-hydroxy-cyclohexylsulfanyl]-acetyl}-19,20-dihydro-mutilin+(1S,2S,5R) diastereomer (38 mg, 0.071 mmol) was treated according to the method of Example 1 Step C to obtain the title compounds (40 mg, quantitative yield) as colorless solid.

$^1$H NMR (400 MHz, DMSO-d, δ, ppm, inter alia): 5.53 (d, 1H, 14-H, J=8 Hz), 4.97 (m, 1H, 2'-OH), 4.40 (d, 1H, 11-OH, J=6 Hz), 3.64 (m, 1H, 2'-H), 3.45-3.20 (m, 3H, 11-H, 22-H), 2.98 (m, 1H, 1'-H), 2.94 (m, 1H, 5'-H), 2.88 (m, 2H, NCH$_2$), 2.37 (bs, 1H, 4-H), 1.34 (s, 3H, 15-CH$_3$), 0.98 (t, 3H, NCH$_2$CH$_3$, J=7 Hz), 0.85 (s, 3H, 18-CH$_3$), 0.80 (d, 3H, 17-CH$_3$, J=7 Hz), 0.63 (m, 6H, 16-CH$_3$, 20-H). MS-ESI (m/z): 538 (MH$^+$).

Example 28

14-O-{[(1R,2R,5R)-5-Amino-2-hydroxy-cyclohexylsulfanyl]-acetyl}-19,20-dihydro-mutilin+(1S,2S,5S) Diastereomer

Step A. 14-O-{[(1R,2R,5S)-5-(tert-Butyl-dimethyl-silyloxy)-2-hydroxy-cyclohexylsulfanyl]-acetyl}-19,20-dihydro-mutilin+(1S,2S,5R) Diastereomer tert-Butyl-dimethyl-(cis-3,4-epoxycyclohexyloxy)-silane (864 mg, 3.78 mmol) from Example 4 Step A was treated with 19,20-dihydro-pleuromutilin thiol (1.5 g, 3.78 mmol) from Example 27 Step A according to the method of Example 1 Step A3. After work up and chromatography of the reaction mixture (silica, cyclohexane/ethyl acetate=3:1) 14-O-{[(1R,2R,5S)-5-(tert-butyl-dimethyl-silyloxy)-2-hydroxy-cyclohexylsulfanyl]-acetyl}-19,20-dihydro-mutilin+(1S,2S,5R) diastereomer (cyclohexane/ethyl acetate=1/1, R$_f$=0.45, 1.2 g, 51% yield) was obtained as colorless solid.

$^1$H NMR (500 MHz, DMSO-d, δ, ppm, inter alia): 5.50 (d, 1H, 14-H, J=8 Hz), 4.81 (m, 1H, 2'-OH), 4.38 (d, 1H, 11-OH, J=6 Hz), 3.88 (m, 1H, 5'-H), 3.50-3.20 (m, 4H, 2'-H, 11-H, 22-H), 2.95 (m, 1H, 1'-H), 2.34 (bs, 1H, 4-H), 1.34 (s, 3H, 15-CH$_3$), 0.84 (m, 12H, 18-CH$_3$, tert-butyl), 0.80 (d, 3H, 17-CH$_3$, J=7 Hz), 0.63 (m, 6H, 16-CH$_3$, 20-H), 0.02 (s, 6H, Si(CH$_3$)$_2$).

Step B. 14-O-{[(1R,2R,5S)-2,5-Dihydroxy-cyclohexylsulfanyl]-acetyl}-19,20-dihydro-mutilin+(1S,2S,5R) Diastereomer 14-O-{[(1R,2R,5S)-5-(tert-butyl-dimethyl-silyloxy)-2-hydroxy-cyclohexylsulfanyl]-acetyl}-19,20-dihydro-mutilin+(1S,2S,5R) diastereomer (1.2 g, 1.92 mmol) was treated according to the method of Example 4 Step C. After work up and chromatography of the reaction mixture (silica, cyclohexane/ethyl acetate=1/4) 14-O-{[(1R,2R,5S)-2,5-dihydroxy-cyclohexylsulfanyl]-acetyl}-19,20-dihydro-mutilin+(1S,2S,5R) diastereomer (cyclohexane/ethyl acetate=1:1, R$_f$=0.2, 720 mg, 73% yield) was obtained as colorless solid.

$^1$H NMR (500 MHz, DMSO-d$_6$, δ, ppm, inter alia): 5.50 (d, 1H, 14-H, J=8 Hz), 4.74 (d, 1H, 2'-OH, J=3 Hz), 4.42 (m, 1H, 5'-OH), 4.38 (d, 1H, 11-OH, J=6 Hz), 3.67 (m, 1H, 5'-H), 3.50-3.20 (m, 4H, 2'-H, 1-H, 22-H), 2.96 (m, 1H, 1'-H), 2.34 (bs, 1H, 4-H), 1.34 (s, 3H, 15-CH$_3$), 0.84 (s, 3H, 18-CH$_3$), 0.80 (d, 3H, 17-CH$_3$, J=7 Hz), 0.63 (m, 6H, 16-CH$_3$, 20-H).

Step C. 14-O-{[(1R,2R,5S)-2-Hydroxy-5-methanesulfonyloxy-cyclohexylsulfanyl]-acetyl}-19,20-dihydro-mutilin+(1S,2S,5R) Diastereomer 14-O-{[(1R,2R,5S)-2,5-dihydroxy-cyclohexylsulfanyl]-acetyl}-19,20-dihydro-mutilin+(1S,2S,5R) diastereomer (720 mg, 1.41 mmol) was treated according to the method of Example 4 Step D. After work up and chromatography of the reaction mixture (silica, cyclohexane/ethyl acetate=1/1) 14-O-{[(1R,2R,5S)-2-hydroxy-5-methanesulfonyloxy-cyclohexylsulfanyl]-acetyl}-19,20-dihydro-mutilin+(1S,2S,5R) diastereomer (cyclohexane/ethyl acetate=1/2, R$_f$=0.4, 640 g, 77% yield) was obtained as colorless solid.

$^1$H NMR (500 MHz, DMSO-d$_6$, δ, ppm, inter alia): 5.51 (d, 1H, 14-H, J=8 Hz), 4.79 (m, 1H, 5'-H), 4.38 (bs, 1H, 11-OH), 3.60-3.20 (m, 7H, 2'-H, 11-H, 22-H, SO$_2$CH$_3$), 2.93 (m, 1H, 1'-H), 2.35 (bs, 1H, 4-H), 1.35 (s, 3H, 15-CH$_3$), 0.84 (s, 3H, 18-CH$_3$), 0.80 (d, 3H, 17-CH$_3$, J=7 Hz), 0.63 (m, 6H, 16-CH$_3$, 20-H).

Step D. 14-O-{[(1R,2R,5R)-5-Azido-2-hydroxy-cyclohexylsulfanyl]-acetyl}-19,20-dihydro-mutilin+(1S,2S,5S) Diastereomer 14-O-{[(1R,2R,5S)-2-hydroxy-5-methanesulfonyloxy-cyclohexylsulfanyl]-acetyl}-19,20-dihydro-mutilin+(1S,2S,5R) diastereomer (640 mg, 1.09 mmol) was treated with sodium azide according to the method of Example 4 Step E. After work up crude 14-O-{[(1R,2R,5R)-5-azido-2-hydroxy-cyclohexylsulfanyl]-acetyl}-19,20-dihydro-mutilin+(1S,2S,5S) diastereomer (quantitative yield, cyclohexane/ethyl acetate=1/2, R$_f$=0.7) was obtained which was directly used for the next step.

Step E. 14-O-{[(1R,2R,5R)-5-Amino-2-hydroxy-cyclohexylsulfanyl]-acetyl}-19,20-dihydro-mutilin+(1S,2S,5S) Diastereomer 14-O-{[(1R,2R,5R)-5-Azido-2-hydroxy-cyclohexylsulfanyl]-acetyl}-19,20-dihydro-mutilin+(1S,2S,5S) diastereomer (584 mg, 1.09 mmol) was treated with triphenylphosphine (342 mg, 1.30 mmol) according to the method of Example 4 Step F. After work up and chromatography (silica, dichloromethane/methanol/1-propanol/water/acetic acid=80/20/6/3/2) with subsequent basic extraction 14-O-{[(1R,2R,5R)-5-amino-2-hydroxy-cyclohexylsulfanyl]-acetyl}-19,20-dihydro-mutilin+(1S,2S,5S) diastereomer (silica, dichloromethane/methanol/35% ammonia solution=100/10/1, R$_f$=0.3, 50.5 mg, 9% yield) was obtained as colorless foam.

$^1$H NMR (500 MHz, DMSO-d$_6$, δ, ppm, inter alia): 5.51 (d, 1H, 14-H, J=8 Hz), 4.77 (m, 1H, 2'-OH), 4.38 (d, 1H, 11-OH, J=8 Hz), 3.60-3.15 (m, 4H, 2'-H, 11-H, 22-H), 2.60 (m, 1H, 1'-H), 2.50 (m, 1H, 5'-H), 2.35 (bs, 1H, 4-H), 1.34 (s, 3H, 15-CH$_3$), 0.84 (s, 3H, 18-CH$_3$), 0.80 (d, 3H, 17-CH$_3$, J=7 Hz), 0.63 (m, 6H, 16-CH$_3$, 20-H). MS-ESI (m/z): 510 (MH$^+$).

Example 29

14-O-{[(1R,2R)-4-Aminomethyl-2-hydroxy-cyclohexylsulfanyl]-acetyl}-mutilin diastereomers+(1S,2S) Diastereomers

Step A. Cyclohex-3-enylmethyl-carbamic acid tert-butyl ester

To a solution of C-Cyclohex-3-enyl-methylamine (3.28 g, 29.5 mmol) and N-methyl-morpholine (2.98 g, 29.5 mmol) in 70 ml of anhydrous dichloromethane was added di-tert-butyldicarbonate (6.44 g, 29.5 mmol) under cooling. The resulting mixture was stirred for 20 hours at room temperature and the solvent was removed under reduced pressure. The residue was diluted with ethyl acetate and washed with 1N HCl. The aqueous phase was extracted three times with ethyl acetate and the combined organic phases were washed with water and brine. The resulting organic phase was dried over magnesium sulfate, filtered and the solvent was removed under reduced pressure to yield 6.57 g of a brown oil. Column chromatography (silica, petrol ether/ethyl acetate=12/1 to 8/1) resulted in cyclohex-3-enylmethyl-carbamic acid tert-butyl ester (petrol ether/ethyl acetate=10/1, R$_f$=0.62, 3.06 g, 49% yield) as colorless solid.

$^1$H NMR (200 MHz, DMSO-d$_6$, δ, ppm, inter alia): 6.90-6.83 (m, 1H, NH), 5.66-5.63 (m, 2H, olef. H), 2.86 (t, 2H, CH$_2$N, J=6 Hz), 2.21-1.50 (m, 6H, 2×CH$_2$), 2.21-0.95 (m, 16H, tert-butyl, 3×CH$_2$ and CH).

Step B. (7-Oxa-bicyclo[4.1.0]hept-3-ylmethyl)-carbamic acid tert-butyl ester To a solution of cyclohex-3-enylmethyl-carbamic acid tert-butyl ester (1.5 g, 7.10 mmol) in 20 ml of anhydrous dichloromethane was added 3-chloroperoxybenzoic acid (2.45 g, 14.2 mmol) under cooling. The resulting mixture was stirred for 19 hours at room temperature and washed with saturated sodium bicarbonate and 0.5M aqueous solution of sodium thiosulphate. The aqueous phase was extracted three times with dichloromethane and the combined organic phases were washed with brine. The resulting organic phase was dried over magnesium sulfate, filtered and the solvent was removed under reduced pressure to yield 1.48 g of crude product. Column chromatography of 3.17 g of crude product (silica, petrol ether/ethyl acetate=3/1) resulted in (7-oxa-bicyclo[4.1.0]hept-3-ylmethyl)-carbamic acid tert-butyl ester (R$_f$=0.19, 2.68 g, 81% yield) as colorless solid.

$^1$H NMR (200 MHz, DMSO-d, δ, ppm, inter alia): 6.84-6.78 (m, 1H, NH), 3.09-3.03 (m, 2H, CHO), 2.71-2.70 (m, 2H, CH$_2$N), 1.37 (s, 9H, tert-butyl). MS-ESI (m/z): 250 (MNa$^+$), 477 (2MNa$^+$).

Step C. 14-O-{[(1R,2R)-4-(tert-Butoxycarbonylamino-methyl)-2-hydroxy-cyclohexylsulfanyl]-acetyl}-mutilin diastereomers+(1S,2S) Diastereomers To a solution of (7-oxa-bicyclo[4.1.0]hept-3-ylmethyl)-carbamic acid tert-butyl ester (1.34 g, 5.90 mmol) and Pleuromutilin thiol (2.32 g, 5.90 mmol) in 25 ml of methanol was added 2M NaOH (2.95 ml, 5.90 mmol) drop wise under cooling. The resulting mixture was stirred at room temperature overnight and the solvent was removed under reduced pressure. The residue was diluted with ethyl acetate and washed with brine. The aqueous phase was extracted three times with ethyl acetate and the combined organic phases were washed with brine. The resulting organic phase was dried over magnesium sulfate, filtered and the solvent was removed under reduced pressure to yield 3.86 g of a crude product. Column chromatography (silica, petrol ether/ethyl acetate=1/1) resulted in 14-O-{[(1R,2R)-4-(tert-butoxycarbonylamino-methyl)-2-hydroxy-cyclohexylsulfanyl]-acetyl}-mutilin diastereomers+(1S,2S) diastereomers ($R_f$=0.24, 2.11 g, 58% yield) as colorless solid.

$^1$H NMR (500 MHz, CDCl$_3$, δ, ppm, inter alia): 6.32-6.40 (m, 1H, 19-H), 5.80-5.71 (m, 1H, 14-H), 5.40-5.15 (m, 2H, 20-H), 4.64, 4.55 (2bs, 1H, NH), 3.79-3.67, 3.58-3.45 (2m, 1H, 2'-H), 3.40-3.31 (m, 1H, 11-H), 3.29-3.11 (m, 2H, 22-H), 3.10-2.92 (m, 2H, CH$_2$N), 2.89-2.77, 2.74-2.64 (2m, 1H, 1'-H), 1.45 (s, 3H, 15-CH$_3$), 1.43 (s, 9H, tert-butyl), 1.17 (s, 3H, 18-CH$_3$), 0.78-0.66 (m, 3H, 16-CH$_3$). MS-ESI (m/z): 644 (MNa$^+$).

Step D. 14-O-{[(1R,2R)-4-Aminomethyl-2-hydroxy-cyclohexylsulfanyl]-acetyl}-mutilin Diasteromers+(1S,2S) Diastereomers To a solution of 14-O-{[(1R,2R)-4-(tert-butoxycarbonylamino-methyl)-2-hydroxy-cyclohexylsulfanyl]-acetyl}-mutilin diastereomers+(1S,2S) diastereomers (1.14 g, 1.83 mmol) in 20 ml of anhydrous dichloromethane was added 20 ml of 1M HCl in diethyl ether drop wise under cooling. The resulting mixture was stirred at room temperature for two days and the solvent was removed under reduced pressure. The residue was diluted with dichloromethane and washed with a saturated solution of sodium bicarbonate. The aqueous phase was extracted three times with dichloromethane. The resulting organic phases were combined and dried over magnesium sulfate, filtered and the solvent was removed under reduced pressure. Column chromatography (silica, dichloromethane/methanol=5/1 to 1/1) resulted in 14-O-{[(1R,2R)-4-aminomethyl-2-hydroxy-cyclohexylsulfanyl]-acetyl}-mutilin diastereomers+(1S,2S) diastereomers (39 mg, 8% yield) as colorless solid.

$^1$H NMR (400 MHz, CDCl$_3$, δ, ppm, inter alia): 6.58-6.38 (m, 1H, 19-H), 5.87-5.68 (m, 1H, 14-H); 5.44-5.12 (m, 2H, 20-H), 4.52-4.34 (m, 1H, 1'-H), 2.68-2.52 (m, 2H, CH$_2$N), 1.46 (s, 3H, 15-CH$_3$), 1.19 (s, 3H, 18-CH$_3$), 0.89 (d, 3H, 17-CH$_3$, J=7 Hz), 0.74 (d, 3H, 16-CH$_3$, J=7 Hz). MS-ESI (m/z): 544 (MNa$^+$).

Example 30

14-O-{[5-Amino-2-chloro-cyclohexylsulfanyl]-acetyl}-mutilin acetate and 14-O-{[4-Amino-2-chloro-cyclohexylsulfanyl]-acetyl}-mutilin acetate

Step A. (1R,3S,6S)-(7-thia-bicyclo[4.1.0]hept-3-yl)-carbamic acid tert-butyl ester+(1S,3R,6R) Diastereomer To a solution of syn-3,4-epoxycyclohexyl-carbamic acid tert-butyl ester (3.55 g, 16.6 mmol) and tetrabutylammonium chloride (500 mg, 1.80 mmol) in 50 ml of tert-butyl methyl ether was added a solution of potassium thiocyanate (8.07 g, 83.0 mmol) in 50 ml of water. The resulting mixture was stirred for 7 days at room temperature and the phases were separated. The aqueous phase was extracted twice with ethyl acetate and the combined organic phases were washed with brine. The resulting organic phase was dried over magnesium sulfate, filtered and the solvent was removed under reduced pressure to yield 4.33 g of a crude product as a colorless solid. Column chromatography (silica, petrol ether/ethyl acetate=7/1 to 3/1) resulted in (1R,3S,6S)-(7-thia-bicyclo[4.1.0]hept-3-yl)-carbamic acid tert-butyl ester+(1S,3R,6R) diastereomer (petrol ether/ethyl acetate=5/1, $R_f$=0.54, 1.88 g, 49% yield based on recovered starting material) as colorless crystals. Fp=105-108° C.

$^1$H NMR (500 MHz, CDCl$_3$, δ, ppm, inter alia): 4.40 (bs, 1H, NH), 3.78 (bs, 1H, 1-H), 3.28-3.20 (m, 1H, 3-H), 3.18-3.09 (m, 1H, 4-H), 2.54 (dd, 1H, 2a-H, J=5 Hz and J=15 Hz), 2.40-2.18 (m, 2H, 5-H), 1.98-1.87 (m, 1H, 2b-H), 1.86-1.72 (m, 1H, 6a-H), 1.58 (s, 9H, tert-butyl), 1.34-1.20 (m, 1H, 6b-H). MS-ESI (m/z): 252 (MNa$^+$).

Step B. 14-O-{[(1R,5R,8R)-3-oxo-2-oxa-4-aza-bicyclo[3.3.1]non-8-ylsulfanyl]-acetyl}-mutilin+(1S,5S,8S) Diastereomer To a solution of (1R,3S,6S)-(7-thia-bicyclo[4.1.0]hept-3-yl)-carbamic acid tert-butyl ester+(1S,3R,6R) diastereomer (2.95 g, 12.9 mmol) in 160 ml of dichloromethane was added p-toluene sulfonic acid (1.21 g, 6.50 mmol) under cooling. The resulting mixture was stirred at room temperature over night and the solvent was removed under reduced pressure to yield 3.26 g of a colorless solid. The crude product was subsequently dissolved in 150 ml of anhydrous tetrahydrofuran, and pleuromutilin tosylate (13.1 g, 24.6 mmol) followed by 1,8-diazabicyclo[5.4.0]undec-7-ene (DBU, 4.2 ml, 28.2 mmol) was added under cooling. The resulting mixture was stirred at room temperature overnight and water was added. The mixture was extracted four times with ethyl acetate and the combined organic phases were washed with water and brine, dried over magnesium sulfate and the solvent was removed under reduced pressure to yield 9.32 g of a colorless solid. Chromatography (silica, dichloromethane/methanol=19/1) resulted in 14-O-{[(1R,5R,8R)-3-oxo-2-oxa-4-aza-bicyclo[3.3.1]non-8-ylsulfanyl]-acetyl}-mutilin+(1S,5S,8S) diastereomer (dichloromethane/methanol=20/1, $R_f$=0.45, 4.36 g, 63% yield) as colorless solid.

$^1$H NMR (500 MHz, CDCl$_3$, δ, ppm, inter alia): 6.46 (dd, 1H, 19-H, J=7 Hz and J=11 Hz), 5.77 (d, 1H, 14-H, J=8 Hz), 5.52 (bs, 1H, NH), 5.40-5.17 (m, 2H, 20-H), 4.68-4.55 (m, 1H, 2'-H), 3.63 (bs, 1H, 4'-H), 3.41-3.30 (m, 2H, 1'-H, 11-H), 3.27-3.12 (m, 2H, 22-H), 1.45 (s, 3H, 15-CH$_3$), 1.18 (s, 3H, 18-CH$_3$), 0.89 (d, 3H, 17-CH$_3$, J=7 Hz), 0.73 (dd, 3H, 16-CH$_3$, J=2 Hz and J=7 Hz). MS-ESI (m/z): 556 (MNa$^+$).

Step C. 14-O-{[5-Amino-2-chloro-cyclohexylsulfanyl]-acetyl}-mutilin acetate and 14-O-{[4-Amino-2-chloro-cyclohexylsulfanyl]-acetyl}-mutilin acetate To a solution of 14-O-{[(1R,5R,8R)-3-oxo-2-oxa-4-aza-bicyclo[3.3.1]non-8-ylsulfanyl]-acetyl}-mutilin+(1S,5S,8S) diastereomer (500 mg, 0.94 mmol) in 2.5 ml of dioxane was added 6M HCl (7 ml) under cooling. The resulting mixture was stirred for 23 hours and added to a saturated solution of sodium bicarbonate. The resulting solution was extracted twice with ethyl acetate and the combined organic phases were washed with brine. The resulting organic phase was dried over magnesium sulfate, filtered and the solvent was removed under reduced pressure to yield 473 mg of crude product. Column chromatography (silica, dichloromethane/methanol=10/1 containing 1% of acetic acid and dichloromethane/methanol/diisopropylether/water/acetic acid=80/20/6/3/2) resulted in 14-O-{[5-Amino-2-chloro-cyclohexylsulfanyl]acetyl}-mutilin acetate (a) (dichloromethane/methanol/diisopropylether/water/acetic acid=80/20/6/3/2, $R_f$=0.5, 178 mg, 36% yield) and 14-O-{[4-Amino-2-chloro-cyclohexylsulfanyl]acetyl}-mutilin acetate (b) (dichloromethane/methanol/diisopropylether/water/acetic acid=80/20/6/3/2, $R_f$=0.43, 91 mg, 18% yield) as a colorless solids.

(a): $^1$H NMR (500 MHz, CDCl$_3$, δ, ppm, inter alia): 6.46 (dd, 1H, 19-H, J=11 Hz and J=17 Hz), 5.78 (d, 1H, 14-H, J=8 Hz), 5.45-5.15 (m, 2H, 20-H), 4.32 (m, 1H, 2'-H), 3.41-3.30 (m, 2H, 1-H, 1'-H), 3.28-3.14 (m, 2H, 22-H), 3.13-3.00 (m, 1H, 5'-H), 2.02 (s, 3H, CH$_3$ of acetate), 1.46 (s, 3H, 15-CH$_3$), 1.19 (s, 3H, 18-CH$_3$), 0.89 (d, 3H, 17-CH$_3$, J=7 Hz), 0.73 (d, 3H, 16-CH$_3$, J=7 Hz). MS-ESI (m/z): 526 (MH$^+$).

(b): $^1$H NMR (500 MHz, CDCl$_3$, δ, ppm, inter alia): 6.49 (dd, 1H, 19-H, J=11 Hz and J=17 Hz), 5.77 (d, 1H, 14-H, J=8 Hz), 5.40-5.15 (m, 2H, 20-H), 3.88-3.73 (m, 1H, 2'-H), 3.50-3.15 (m, 3H, 11-H, 22-H), 3.00-2.70 (m, 2H, 1'-H, 4'-H), 2.03 (s, 3H, CH$_3$ of acetate), 1.46 (s, 3H, 15-CH$_3$), 1.18 (s, 3H, 18-CH$_3$), 0.88 (d, 3H, 17-CH$_3$, J=7 Hz), 0.74 (d, 3H, 16-CH$_3$, J=7 Hz). MS-ESI (m/z): 526 (MH$^+$).

Example 31

14-O-[(4-Amino-1-hydroxy-cyclohexylmethylsulfanyl)-acetyl]-mutilin hydrochloride Step A. (1-Oxa-spiro[2,5]oct-6-yl)-carbamic acid tert-butyl ester (4-Methylene-cyclohexyl)-carbamic acid tert-butyl ester (Raju, B. et al, *Bioorganic and Medicinal Chemistry Letters* 2004, 14(12), 3103-3107) (2.3 g, 10.9 mmol) was treated with 3-chloroperbenzoic acid (70% purity, 3.76 g, 21.8 mmol, uncorrected) according to the method of Example 7 Step B. After work up the title compound was obtained (2.3 g, 93% yield) as a yellow solid.

$^1$H NMR (DMSO-d$_6$, 400 MHz, δ, ppm): 6.77 (bd, 1H, NH, J=7 Hz), 3.35 (m, 1H), 2.55, 2.51 (2s, 2H), 1.86-1.75 (m, 2H), 1.73-1.67 (m, 2H), 1.47-1.28 (m, 2H), 1.36 (s, 9H, tert-butyl), 1.22-1.13 (m, 2H).

Step B. 14-O-[(4-tert-Butoxycarbonylamino-1-hydroxy-cyclohexylmethylsulfanyl)-acetyl]-mutilin Pleuromutilin thiol (2.6 g, 6.59 mmol) was treated with (1-Oxa-spiro[2,5]oct-6-yl)-carbamic acid tert-butyl ester (1 g, 4.40 mmol) according to the method of Example 1 Step A3. After workup and chromatography of the mixture (silica, toluene/ethyl acetate=5/1->3/1) the title compound (toluene/ethyl acetate=1/1, $R_f$=0.44, 0.41 g, 15% yield, uncorrected) was obtained as a colorless foam.

$^1$H NMR (DMSO-d$_6$, 500 MHz, δ, ppm, inter alia): 6.66 (d, 1H, NH, J=8 Hz), 6.14 (dd, 1H, 19-H, J=18 Hz and 11 Hz), 5.54 (d, 1H, 14-H, J=8 Hz), 5.10-5.02 (m, 2H, 20-H), 4.49 (bs, 1H, 11-OH), 4.23 (bs, 1H), 3.46-3.28 (m, 3H), 3.08 (m, 1H, 4'-H), 2.60 (s, 2H, COHCH$_2$S), 2.40 (bs, 1H, 4-H), 2.18 (m, 1H), 2.12-2.02 (m, 3H), 1.69-1.54 (m, 3H), 1.52-1.43 (m, 3H), 1.35 (s, 3H, 15-CH$_3$), 1.35 (s, 9H, tert-butyl), 1.32-1.21 (m, 4H), 1.08 (s, 3H, 18-CH$_3$), 1.14-0.98 (m, 1H), 0.81 (d, 3H, 17-CH$_3$, J=7 Hz), 0.62 (d, 3H, 16-CH$_3$, J=7 Hz). MS-ESI (m/z): 644 (MNa$^+$).

Step C. 14-O-[(4-Amino-1-hydroxy-cyclohexylmethylsulfanyl)-acetyl]-mutilin

14-O-[(4-tert-Butoxycarbonylamino-1-hydroxy-cyclohexylmethylsulfanyl)-acetyl]-mutilin (0.36 g, 0.58 mmol) was treated with trifluoroacetic acid (0.72 ml) according to the method of Example 1 Step B. After workup and chromatography of the mixture (silica, ethyl acetate/methanol/NH$_4$OH (25%)=50/50/1) the title compound ($R_f$=0.04, 0.13 g, 43% yield) was obtained as colorless foam.

$^1$H NMR (DMSO-d$_6$, 400 MHz, δ, ppm, inter alia): 6.13 (dd, 1H, 19-H, J=18 Hz and 11 Hz), 5.53 (d, 1H, 14-H, J=8 Hz), 5.10 (d, 1H, 20-H, J=2 Hz), 5.02 (d, 1H, 20-H, J=2 Hz), 4.49 (bs, 1H), 4.21 (bs, 1H), 3.42 (m, 1H), 3.23 (q, 2H, H-22, J=14 Hz), 2.60 (s, 2H, COHCH$_2$S), 2.47-2.36 (m, 2H), 2.23-2.14 (m, 1H), 2.12-2.04 (m, 3H), 1.68-1.54 (m, 3H), 1.41-1.20 (m, 5H), 1.35 (s, 3H, 15-CH$_3$), 1.05 (s, 3H, 18-CH$_3$), 1.03 (m, 1H), 0.81 (d, 3H, 17-CH$_3$, J=7 Hz), 0.62 (d, 3H, 16-CH$_3$, J=7 Hz). MS-ESI (m/z)=522 (MH$^+$), 544 (MNa$^+$).

Step D. 14-O-[(4-Amino-1-hydroxy-cyclohexylmethylsulfanyl)-acetyl]-mutilin hydrochloride A solution of 14-O-[(4-amino-1-hydroxy-cyclohexylmethylsulfanyl)-acetyl]-mutilin (0.1 g, 0.19 mmol) in 1 ml dioxane was treated with aqueous hydrochloric acid (0.05 M, 11.6 ml, 0.58 mmol) under stirring according to the method of Example 1 Step C. After 1 hour the mixture was lyophilized overnight to give the title compound (107 mg, 99% yield) as white solid.

$^1$H NMR (DMSO-d$_6$, 400 MHz, δ, ppm, inter alia): 7.88 (s, 3H, NH$_3^+$), 6.13 (dd, 1H, 19-H, J=18 Hz and 11 Hz), 5.52 (d, 1H, J=8 Hz), 5.08 (dd, 1H, 20-H, J=5 Hz and 18 Hz), 5.03 (dd, 1H, 20-H, J=5 Hz and 11 Hz), 3.25 (q, 2H, 22-H, J=14 Hz), 2.85 (m, 1H, 4'-H), 2.62 (s, 2H, COHCH$_2$S), 2.40 (s, 1H, 4-H), 2.23-2.03 (m, 4H), 1.71-1.56 (m, 6H), 1.47 (m, 1H), 1.36 (s, 3H, 15-CH$_3$), 1.41-1.19 (m, 4H), 1.05 (s, 3H, 18-CH$_3$), 1.00 (m, 1H), 0.81 (d, 3H, 17-CH$_3$, J=7 Hz), 0.62 (d, 3H, 16-CH$_3$, J=7 Hz).

Example 32

14-O-{[(1R,2R)-2-Hydroxy-5-(3-methylamino-propyl)-cyclohexylsulfanyl]-acetyl}-mutilin+(1S,2S) Diastereomer and 14-O-{[(1R,2R)-2-Hydroxy-4-(3-methylamino-propyl)-cyclohexylsulfanyl]-acetyl}-mutilin+(1S,2S) Diastereomer Step A. 3-Cyclohex-3-enyl-N-methyl-propionamide Methyl amine (8 M in EtOH, 75 ml, 600 mmol) was added to a mixture of 3-cyclohex-3-enyl-propionic acid methyl ester (German patent DE 4023848 A1 19920130) (20.0 g, 119 mmol) in 75 mL of methanol. The mixture was stirred at room temperature for one day. Additional Methyl amine (8 M in EtOH, 40 ml, 320 mmol) was added to the mixture and stirring continued for one more day. The mixture was concentrated and the residue was taken up in ethyl acetate, washed with 0.5 M aqueous HCl, dried and stripped of the solvent to give the title compound (19.50 g, 98% yield, uncorrected) as a pale orange solid.

¹H NMR (CDCl₃, 200 MHz, δ, ppm): 5.58 (s, 2H, olefinic H), 5.57 (m, 1H, NH), 2.74 (d, 3H, NCH₃, J=5 Hz), 2.20-1.90 (m, 5H), 1.75-1.40 (m, 5H), 1.15 (m, 1H).

Step B. (3-Cyclohex-3-enyl-propyl)-methyl-amine

A solution of 3-cyclohex-3-enyl-N-methyl-propionamide (15.5 g, 92.7 mmol) in 55 ml of tetrahydrofuran was added dropwise over a period of 25 min to a suspension of lithium aluminium hydride (95% purity, 5.3 g, 139 mmol, corrected) in 120 ml of tetrahydrofuran at 0° C. under stirring. The mixture was refluxed for 4 hours, stirred overnight at room temperature and quenched with 2 M aqueous NaOH, diluted with tetrahydrofuran, stirred and filtered. The filtrate was concentrated and the residue was acidified with 1 M aqueous HCl and washed with dichloromethane. The aqueous phase was basified with 1 M aqueous NaOH, and extracted with ethyl acetate. The organic extract was dried and concentrated to obtain the title compound (9.38 g, 66% yield) as pale yellow oil.

¹H NMR (CDCl₃, 200 MHz, δ, ppm): 5.58 (d, 2H, olefinic H, J=2 Hz), 2.50 (t, 2H, J=7 Hz), 2.36 (s, 3H, NCH₃), 2.15-1.90 (m, 3H), 1.75-1.05 (m, 9H).

Step C.
(3-Cyclohex-3-enyl-propyl)-methyl-carbamic acid tert-butyl ester

Ethyl-diisopropyl-amine (11.3 ml, 66.0 mmol) and di-tert-butyl-dicarbonate (14.4 g, 66.0 mmol) were added to a solution of (3-cyclohex-3-enyl-propyl)-methyl-amine (7.50 g, 48.9 mmol) in 75 ml of dioxane. The mixture was stirred at room temperature for 3 days, diluted with ethyl acetate and washed with cold 0.1 M aqueous HCl, and saturated aqueous sodium bicarbonate, dried over sodium sulfate and concentrated in vacuo to give a mixture. After chromatography of the mixture (silica, dichloromethane) the title compound (14.24 g, quantitative yield, uncorrected) was obtained as pale yellow oil.

¹H NMR (CDCl₃, 200 MHz, δ, ppm): 5.65 (d, 2H, olefinic H, J=2 Hz), 3.19 (t, 2H, CH₂N, J=7 Hz), 2.84 (s, 3H, NCH₃), 2.15-1.90 (m, 3H), 1.75-1.30 (m, 5H), 1.45 (s, 9H, tert-butyl), 1.30-1.05 (m, 3H).

Step D. Methyl-[3-(7-oxa-bicyclo[4.1.0]hept-3-yl)-propyl]-carbamic acid tert-butyl ester (3-Cyclohex-3-enyl-propyl)-methyl-carbamic acid tert-butyl ester (14.24 g, 56.2 mmol) was treated with 3-chloroperbenzoic acid (70% purity, 14.8 g, 60 mmol, corrected) according to the method of Example 7 Step B and stirred for 3 hours at room temperature. After work up the title compound (14.6 g, 96% yield, uncorrected) was obtained as pale yellow oil.

¹H NMR (CDCl₃, 200 MHz, δ, ppm): 3.15-3.00 (m, 4H), 2.75 (s, 3H, NCH₃), 2.15-0.70 (m, 11H), 1.38 (s, 9H, tert-butyl).

Step E. 14-O-{{(1R,2R)-5-[3-(tert-Butoxycarbonyl-methyl-amino)-propyl]-2-hydroxy-cyclohexylsulfanyl}-acetyl}-mutilin+(1S,2S) Diastereomer and 14-O-{{(1R,2R)-4-[3-(tert-Butoxycarbonyl-methyl-amino)-propyl]-2-hydroxy-cyclohexylsulfanyl}-acetyl}-mutilin+(1S,2S) Diastereomer Methyl-[3-(7-oxa-bicyclo[4.1.0]hept-3-yl)-propyl]-carbamic acid tert-butyl ester (3.00 g, 11.1 mmol) was treated with pleuromutilin thiol (6.57 g, 16.7 mmol) according to the method of Example 1 Step A3 and stirred for 3 days at room temperature. After workup and chromatography of the mixture (silica, cyclohexane/ethyl acetate=1:1) a mixture of the title compounds (R$_f$=0.29, 3.20 g, 43% yield, uncorrected) was obtained as white foam. The mixture was taken to the next step.

Step F. 14-O-{[(1R,2R)-2-Hydroxy-5-(3-methylamino-propyl)-cyclohexylsulfanyl]-acetyl}-mutilin+ (1S,2S) Diastereomer and 14-O-{[(1R,2R)-2-Hydroxy-4-(3-methylamino-propyl)-cyclohexylsulfanyl]-acetyl}-mutilin+(1S,2S) Diastereomer HCl (4 M in dioxane, 5.30 ml, 21.2 mmol) was added to the mixture of compounds from Example 32 Step E (5.63 g, 8.48 mmol, uncorrected) in 50 ml of dioxane. The mixture was stirred for 4 hours and stripped of the solvent. The residue was partioned between dichloromethane and saturated aqueous bicarbonate and the organic layer was separated, dried and stripped of the solvent to give a mixture. After chromatography (silica, dichloromethane/methanol/28%-aq. NH₃=91/6/3) 14-O-{[(1R,2R)-2-Hydroxy-5-(3-methylamino-propyl)-cyclohexylsulfanyl]-acetyl}-mutilin+(1S,2S) diastereomer (a) (dichloromethane/methanol/28%-aq. NH₃=88/8/4, R$_f$=0.18, 117 mg, 3% yield, uncorrected) and 14-O-{[(1R,2R)-2-Hydroxy-4-(3-methylamino-propyl)-cyclohexylsulfanyl]-acetyl}-mutilin (b) (dichloromethane/methanol/28%-aq. NH₃=88/8/4, R$_f$=0.10, 172 mg, 4% yield, uncorrected) were obtained as white foams.

(a): ¹H NMR: (400 MHz, DMSO-d₆, δ, ppm, inter alia): 6.12 (dd, 1H, 19-H, J=11 Hz and 18 Hz), 5.53 (d, 1H, 14-H, J=8 Hz), 5.1-5.0 (m, 2H, 20-H), 4.74 (bs, 1H, 2'-OH), 4.49 (bs, 1H, 11-OH), 3.59 (m, 1H), 3.42 (m, 1H, 11-H), 3.20 (m), 2.90 (m, 1H), 2.42-2.36 (m, 3H), 2.24 (s, 3H, CH₃—N), 2.21-2.01 (m), 1.72-1.56 (m), 1.55-1.10 (m), 1.36 (s, 3H, 15-CH₃), 1.05 (s, 3H, 18-CH₃), 1.00 (m, 1H), 0.81 (d, 3H, 17-CH₃, J=7 Hz), 0.62 (d, 3H, 16-CH₃, J=7 Hz).

(b): ¹H NMR: (500 MHz, DMSO-d₆, δ, ppm, inter alia): 6.13 (m, 1H, 19-H), 5.54 (d, 1H, H-14, J=9 Hz), 5.10-5.00 (m, 2H, 20-H), 4.74 (bs, 1H, 2'-OH), 4.48 (bs, 1H, 11-OH), 3.70 (bs, 1H, 2'-H), 3.41 (m, 1H, 11-H), 3.20 (m, 2H, H-22), 2.85 (m, 1H), 2.43-2.37 (m, 3H), 2.24 (s, 3H, CH₃—N), 2.22-1.89 (m), 1.70-0.96 (m), 1.35 (s, 3H, 15-CH₃), 1.05 (s, 3H, 18-CH₃), 0.81 (d, 3H, 17-CH₃, J=7 Hz), 0.62 (d, 3H, 16-CH₃, J=7 Hz).

Example 33

14-O-{[(1R,2R)-5-(3-Amino-propyl)-2-hydroxy-cyclohexylsulfanyl]-acetyl}-mutilin+(1S,2S) Diastereomer and 14-O-{[(1R,2R)-4-(3-Amino-propyl)-2-hydroxy-cyclohexylsulfanyl]-acetyl}-mutilin+(1S, 2S) Diastereomer Step A. N-tert-Butoxycarbonyl-(3-cyclohex-3-enyl-propyl)-carbamic acid tert-butyl ester Sodium hydride (60% in mineral oil, 2.5 g, 62.5 mmol, corrected) was added in several portions over a period of 15 min to an ice-cold mixture of di-tert-butyl-iminodicarboxylate (22.0 g, 100 mmol) in 60 ml of dimethyl formamide and 180 ml of tetrahydrofuran under stirring. A solution of toluene-4-sulfonic acid 3-cyclohex-3-enyl-propyl ester (Marvell, E.; Sturmer, D.; Kunston, R. *Journal of Organic Chemistry* 1968, 33, 2991-2993) (14.8 g, 50.0 mmol) in a mixture of 15 ml of dimethyl formamide and 45 ml of tetrahydrofuran was charged to it dropwise over 30 minutes. The mixture was stirred for 7 hours at 70° C. and 16 hours at room temperature, diluted with water and extracted with tert-butyl methyl ether. The organic extract was washed with water, brine and stripped of the solvent to give a mixture. After chromatography of the mixture (silica, toluene/cyclohexane=75/25) the title compound (ethyl acetate/toluene=15/85, $R_f$=0.19, 14.7 g, 86% yield, uncorrected) was obtained as clear yellow oil.

$^1$H NMR (CDCl$_3$, 200 MHz, δ, ppm): 5.57 (d, 2H, olefinic H, J=2 Hz), 3.46 (t, 2H, CH$_2$N, J=8 Hz), 2.15-1.90 (m, 3H), 1.75-1.30 (m, 5H), 1.43 (s, 18H, tert-butyl), 1.30-1.00 (m, 3H).

Step B. N-tert-Butoxycarbonyl-[3-(7-oxa-bicyclo [4.1.0]hept-3-yl)-propyl]-carbamic acid tert-butyl ester N-tert-Butoxycarbonyl-(3-cyclohex-3-enyl-propyl)-carbamic acid tert-butyl ester (12.2 g, 29.4 mmol, corrected) was treated with 3-chloroperbenzoic acid (70% purity, 8.7 g, 35.3 mmol, corrected) according to the method of Example 7 Step B and stirred at room temperature for 4.5 hours. After work up the title compound (9.38 g, 90% yield) was obtained as light yellow oil.

$^1$H NMR (CDCl$_3$, 200 MHz, δ, ppm): 3.43 (t, 2H, CH$_2$N, J=8 Hz), 3.06 (bs, 2H), 2.15-0.70 (m, 11H), 1.43 (s, 18H, tert-butyl).

Step C. 14-O-{[(1R,2R)-5-(3-N,N-Bis-(tert-butoxycarbonyl)-amino-propyl)-2-hydroxy-cyclohexylsulfanyl]-acetyl}-mutilin+(1S,2S) Diastereomer and 14-O-{[(1R,2R)-4-(3-N,N-Bis-(tert-butoxycarbonyl)-amino-propyl)-2-hydroxy-cyclohexylsulfanyl]-acetyl}-mutilin+(1S,2S) Diastereomer N-tert-Butoxycarbonyl-[3-(7-oxa-bicyclo[4.1.0]hept-3-yl)-propyl]-carbamic acid tert-butyl ester (3.00 g, 8.44 mmol) was treated with pleuromutilin thiol (5.00 g, 12.7 mmol) according to the method of Example 1 Step A3 and stirred for 24 h. After chromatography of the mixture (silica, petroleum benzene/ethyl acetate=7/3→1/1) a mixture of the title compounds (petroleum benzene/ethyl acetate=3/2, $R_f$=0.30, 3.68 g, 58% yield, uncorrected) was obtained as white foam.

$^1$H NMR (DMSO-d$_6$, 500 MHz, δ, ppm, inter alia): 6.12 (dd, 1H, 19-H, J=11 Hz and 18 Hz), 5.53 (d, 1H, 14-H, J=8 Hz), 5.10-5.00 (m, 2H, 20-H), 4.75 (bs, 1H), 4.48 (bs, 1H, 11-OH), 3.69 (m, 0.5H), 3.60 (m, 0.5H), 3.45-3.38 (m, 3H), 3.26 (d, 1H, 22-H, J=12 Hz), 3.21 (d, 1H, 22-H, J=13 Hz), 2.91 (m, 0.5H), 2.85 (m, 0.5H), 2.39 (bs, 1H, 4-H), 2.18 (dd, 1H, 2-H, J=11 Hz and 19 Hz), 2.12-2.01 (m, 3H), 1.92 (m, 1H), 1.70-0.96 (m), 1.41 (s, 18H, tert-butyl), 1.35 (s, 3H, 15-CH$_3$), 1.05 (s, 3H, 18-CH$_3$), 0.81 (d, 3H, 17-CH$_3$, J=7 Hz), 0.62 (d, 3H, 16-CH$_3$, J=7 Hz).

Step D. 14-O-{[(1R,2R)-5-(3-Amino-propyl)-2-hydroxy-cyclohexylsulfanyl]-acetyl}-mutilin+(1S,2S) Diastereomer and 14-O-{[(1R,2R)-4-(3-Amino-propyl)-2-hydroxy-cyclohexylsulfanyl]-acetyl}-mutilin+ (1S,2S) Diastereomer A mixture of the mixture from Example 33 Step C (250 mg, 0.33 mmol) was treated with trifluoroacetic acid (6 ml) according to the method of Example 1 Step B, and stirred at room temperature for 5 days. After work up and chromatography (silica, dichloromethane/methanol/28% aq NH$_4$OH=86:10:4) a mixture of the title compounds ($R_f$=0.08 and 0.12, 50 mg, 27% yield, uncorrected) was obtained as white foam.

$^1$H NMR (DMSO-d$_6$, 500 MHz, δ, ppm, inter alia): 6.14 (dd, 1H, 19-H, J=11 Hz and 18 Hz), 5.55 (d, 1H, 14-H, J=8 Hz), 5.13-5.02 (m, 2H, 20-H), 4.75 (bs, 1H), 4.50 (bs, 1H, 11-OH), 3.72 (m, 0.5H), 3.61 (m, 0.5H), 3.50-3.05 (m), 2.92 (m, 0.5H), 2.86 (m, 0.5H), 2.47 (m, 2H, —CH$_2$N), 2.41 (bs, 1H, 4-H), 2.19 (dd, 1H, 2-H), 2.13-2.03 (m, 3H), 1.94 (m, 1H), 1.73-0.82 (m), 1.37 (s, 3H, 15-CH$_3$), 1.06 (s, 3H, 18-CH$_3$), 0.82 (d, 3H, 17-CH$_3$, J=7 Hz), 0.63 (d, J=7 Hz, 3H, 16-CH$_3$). MS-ESI (m/z): 550 (MH$^+$), 572 (MNa$^+$).

Example 34

14-O-[(4-Amino-2-oxo-cyclohexylsulfanyl)-acetyl]-mutilin

Step A. Thiobenzoic acid S-((1R,2R,4R)-4-tert-butoxycarbonylamino-2-hydroxy-cyclohexyl) ester+ (1S,2S,4S) Diastereomer and Thiobenzoic acid S-((1R,2R,5S)-5-tert-butoxycarbonylamino-2-hydroxy-cyclo hexyl) ester+(1S,2S,5R) Diastereomer To a solution of syn-3,4-epoxycyclohexyl-carbamic acid tert-butyl ester (63.3 g, 0.29 mol) in 630 ml of toluene was added thiobenzoic acid (105.13 ml, 0.90 mmol) followed by tetrabutyl ammonium chloride monohydrate (2.66 g, 9.00 mmol). The mixture was stirred under argon for 3.5 hours and was charged with saturated aqueous sodium bicarbonate, stirred for 10 min and the organic phase was separated. The organic phase was washed with saturated aqueous sodium bicarbonate, brine, dried and the solvent was removed under vacuum to obtain the crude mixture of the title compounds. The mixture was crystallized from a mixture of toluene/heptane (1/1) to give thiobenzoic acid S-((1R,2R,4R)-4-tert-butoxycarbonylamino-2-hydroxy-cyclohexyl) ester+(1S,2S, 4S) diastereomer (a) (22.1 g, 21% yield) as a solid. The mother liquor was chromatographed (silica, toluol/ethyl acetate=8/1->7/1) to obtain thiobenzoic acid S-((1R,2R,4R)-4-tert-butoxycarbonylamino-2-hydroxy-cyclohexyl) ester+ (1S,2S,4S) diastereomer (a) (toluene/ethyl acetate=3/1, $R_f$=0.35, 4.09 g, 4% yield) as a solid and thiobenzoic acid S-((1R,2R,5S)-5-tert-butoxycarbonylamino-2-hydroxy-cyclohexyl) ester+(1S,2S,5R) diastereomer (b) (toluene/ethyl acetate 3/1, $R_f$=0.25, 16.57 g, 16% yield) as oil.

(a): $^1$H NMR (500 MHz, DMSO-d$_6$, δ, ppm): 7.88 (d, 2H, aromatic H, J=7 Hz), 7.66 (t, 1H, aromatic H, J=7 Hz), 7.53 (t, 2H, aromatic H, J=8 Hz), 6.82 (d, 1H, NH, J=8 Hz), 5.08 (d, 1H, OH, J=6 Hz), 3.41 (m, 1H), 3.33-3.28 (m, 2H), 2.08 (bd, 1H), 1.98 (m, 1H), 1.75 (m, 1H), 1.36 (s, 9H, tert-butyl), 1.49-1.18 (m, 3H).

(b): $^1$H NMR (500 MHz, DMSO-d$_6$, δ, ppm): 7.91 (d, 2H, aromatic H, J=8 Hz), 7.67 (t, 1H, aromatic H, J=7 Hz), 7.53 (t, 2H, aromatic H, J=8 Hz), 6.85 (d, 1H, NH, J=7 Hz), 5.12 (d, 1H, OH, J=3 Hz), 3.89 (d, 1H, J=4 Hz), 3.62 (bs, 1H), 3.41 (bs, 1H), 2.10 (m, 1H), 1.69-1.48 (m, 5H), 1.35 (s, 9H, tert-butyl).

Step B. Thiobenzoic acid S-(4-tert-butoxycarbonylamino-2-oxo-cyclohexyl) ester

A mixture of thiobenzoic acid S-((1R,2R,4R)-4-tert-butoxycarbonylamino-2-hydroxy-cyclohexyl) ester+(1S,2S, 4S) diastereomer (5 g, 14.2 mmol), 4 Å-molecular sieve (3 g) 1,1-dihydro-1,1,1-triacetoxy-1,2-benziodoxol-3(1H)-one (6.33 g, 15 mmol) in 100 ml of dichloromethane was stirred under argon at 5° C. for 1 hour and 1 hour at room temperature. The mixture was filtered over celite, dried and concentrated under vacuum to give the crude product. After chromatography of the mixture (silica, toluene/ethyl acetate=7/1) the title compound (toluene/ethyl acetate=3/1, $R_f$=0.48, 4.18 g, 84% yield) was obtained as a white solid.

$^1$H NMR (DMSO-$d_6$, 200 MHz, δ, ppm): 7.83 (d, 2H, aromatic H, J=7 Hz), 7.71 (t, 1H, aromatic H, J=7 Hz), 7.57 (t, 2H, aromatic H, J=7 Hz), 7.16 (bd, 1H, NH, J=8 Hz), 4.48 (m, 1H), 3.98, 3.7 (2m, 1H), 2.58 (m, 2H), 2.31-1.68 (m, 4H), 1.39 (s, 9H, tert-butyl).

Step C. 14-O-[(2-Benzoyloxy-4-tert-butoxycarbonylamino-cyclohex-1-en-ylsulfanyl)-acetyl]-mutilin A mixture of thiobenzoic acid S-(4-tert-butoxycarbonylamino-2-oxo-cyclohexyl) ester (2 g, 5.72 mmol), pleuromutilin tosylate (3.96 g, 7.44 mmol), potassium carbonate (1.58 g, 11.44 mmol) and tetrabutyl ammonium chloride monohydrate (0.2 g, 0.68 mmol) in 20 ml of dimethyl formamide and 2 ml of water was stirred for 24 hours. The mixture was taken up in ethyl acetate, washed with aqueous saturated sodium bicarbonate and brine, dried and concentrated under vacuum. After chromatography of the mixture (silica, toluene/ethyl acetate=5/1) the title compound (toluene/ethylacetate=3/1, $R_f$=0.24, 2.36 g, 58% yield) was obtained as white foam.

$^1$H NMR (DMSO-$d_6$, 400 MHz, δ, ppm, inter alia): 7.99 (d, 2H, aromatic H, 3=7 Hz), 7.70 (t, 1H, aromatic H, J=7 Hz), 7.54 (t, 2H, aromatic H, J=8 Hz), 6.91 (bd, 1H, NH, J=5 Hz), 6.13 (dd, 1H, 19-H, J=18 Hz and 11 Hz), 5.53 (dd, 1H, 14-H, J=3 Hz and 8 Hz), 5.10 (dd, 1H, 20-H, J=2 Hz and 17 Hz), 5.04 (dd, 1H, 20-H, J=2 Hz and 11 Hz), 4.49 (d, 1H, 11-OH, J=6 Hz), 3.64 (bs, 4'-H, 1H), 3.49-3.35 (m, 3H), 2.46-2.34 (m, 3H), 2.28-2.02 (m, 4H), 1.87 (m, 1H), 1.67-1.42 (m, 5H), 1.41-1.36 (m, 1H), 1.37 (s, 9H, tert-butyl), 1.34 (s, 3H, 15-CH$_3$), 1.23 (m, 1H), 1.06 (s, 3H, 18-CH$_3$), 1.00 (m, 1H), 0.81 (d, 3H, 17-CH$_3$, J=7 Hz), 0.58 (d, 3H, 16-CH$_3$, J=7 Hz, 3H). MS-ESI (m/z): 732 (MNa$^+$).

Step D. 14-O-[(4-tert-Butoxycarbonylamino-2-α-cyclohexylsulfanyl)-acetyl]-mutilin A solution of 14-O-[(2-benzoyloxy-4-tert-butoxycarbonylamino-cyclohex-1-en-ylsulfanyl)-acetyl]-mutilin (0.8 g, 1.13 mmol) in 8 ml of methanol and 1.25 ml of aqueous 1M sodium hydroxide (1.25 mmol) was stirred for 0.5 hours. The mixture was diluted with water and extracted with dichloromethane. The organic extract was dried over magnesium sulfate and concentrated under vacuum to give a mixture. After chromatography of the mixture (silica, toluene/ethyl acetate=5/1) the title compound (toluene/ethyl acetate=3/1, $R_f$=0.13, 0.57 g, 83% yield) was obtained as white foam.

$^1$H NMR (DMSO-$d_6$, 400 MHz, δ, ppm, inter alia): 7.04 (m, 1H, NH), 6.12 (m, 1H, 19-H), 5.53 (m, 1H, 14-H), 5.09-5.02 (m, 2H, 20-H), 4.49 (m, 1H, 11-OH), 3.65 (m, 1H, 4'-H), 3.40 (m, 1H), 3.32-3.14 (m, 2H), 2.39 (s, 1H, 4-H), 2.40-0.95 (m), 1.35 (s, 9H, tert-butyl), 1.34 (s, 3H, 15-CH$_3$), 1.05 (s, 3H, 18-CH$_3$), 0.81 (d, 3H, 17-CH$_3$, J=7 Hz), 0.60 (d, 3H, 16-CH$_3$, J=7 Hz). MS-ESI (m/z): 628 (MNa$^+$).

Step E. 14-O-[(4-Amino-2-oxo-cyclohexylsulfanyl)-acetyl]-mutilin

14-O-[(4-tert-Butoxycarbonylamino-2-oxo-cyclohexylsulfanyl)-acetyl]-mutilin (0.55 g, 0.91 mmol) was treated with 2.3 ml of 4M HCl in dioxane (9.2 mmol) according to the method of Example 32 Step F and stirred for 2 hours at room temperature. After work up the title compound (0.42 g, 91% yield) was obtained as white foam.

$^1$H NMR (DMSO-$d_6$, 400 MHz, δ, ppm, inter alia): 6.13 (m, 1H, 19-H), 5.53 (d, 1H, 14-H, J=4 Hz), 5.05 (m, 2H, 20-H), 4.48 (bs, 1H, 11-OH), 3.55-3.10 (m), 2.41-2.30 (m), 2.22-2.13 (m, 2H), 2.12-1.99 (m, 3H), 1.69-1.55 (m, 3H), 1.55-1.20 (m), 1.35 (s, 3H, 15-CH$_3$), 1.05 (s, 3H, 18-CH$_3$), 0.99 (m, 1H), 0.81 (d, 3H, 17-CH$_3$, J=7 Hz), 0.61 (d, 3H, 16-CH$_3$).

Example 35

14-O-[(5-Amino-2-oxo-cyclohexylsulfanyl)-acetyl]-mutilin succinic acid salt

Step A. Thiobenzoic acid S-(5-tert-butoxycarbonylamino-2-oxo-cyclohexyl) ester Thiobenzoic acid S-((1R,2R,5S)-5-tert-butoxycarbonylamino-2-hydroxy-cyclohexyl) ester+(1S,2S,5R) diastereomer (8.7 g, 24.8 mmol) from Example 34 Step A was treated with 1,1-dihydro-1,1,1-triacetoxy-1,2-benziodoxol-3(1H)-one (11.02 g, 26 mmol) according to the method of Example 34 Step B. After work up and chromatography (silica, toluene/ethyl acetate=6/1) of the mixture the title compound (toluene/ethyl acetate=3/1, $R_f$=0.43, 7.15 g, 83% yield) was obtained as a white solid.

$^1$H NMR (DMSO-$d_6$, 200 MHz, δ, ppm): 7.91 (d, 2H, aromatic H, J=7 Hz), 7.71 (t, 1H, aromatic H, J=7 Hz), 7.55 (t, 2H, aromatic H, J=7 Hz), 6.97 (d, 1H, NH, J=7 Hz), 4.70 (m, 1H), 4.02 (m, 1H), 2.79 (m, 1H), 2.46-2.22 (m, 2H), 2.18-1.93 (m, 2H), 1.75 (m, 1H), 1.39 (s, 9H, tert-butyl).

Step B. 14-O-[(2-Benzoyloxy-5-tert-butoxycarbonylamino-cyclohex-1-en-ylsulfanyl)-acetyl]-mutilin Thiobenzoic acid S-(5-tert-butoxycarbonylamino-2-oxo-cyclohexyl) ester (1 g, 2.86 mmol) was treated with pleuromutilin tosylate (1.98 g, 3.72 mmol) according to the method of Example 34 Step C. After work up and chromatography (silica, toluene/ethyl actate=5/1) of the mixture the title compound (toluene/ethyl acetate=3/1, $R_f$=0.23, 1.33 g, 65% yield) was obtained as white foam.

$^1$H NMR (DMSO-$d_6$, 500 MHz, δ, ppm, inter alia): 8.00 (d, 2H, aromatic H, J=8 Hz), 7.70 (t, 1H, aromatic H, J=7 Hz), 7.54 (t, 2H, aromatic H, J=8 Hz), 6.96 (d, 0.5H, J=8 Hz), 6.92 (d, 0.5H, J=8 Hz), 6.12 (dd, 1H, 19-H, J=18 Hz and 11 Hz), 5.52 (dd, 1H, 14-H, J=3 Hz and 8 Hz), 5.08 (dd, 1H, H-20, J=2 Hz and 18 Hz), 5.05 (dd, 1H, H-20, J=2 Hz and 11 Hz), 4.51 (t or 2d, 1H, J=6 Hz), 3.63 (bs, 1H), 3.47-3.33 (m, 3H), 2.55 (m, 1H), 2.44-2.32 (m, 2H), 2.29-2.14 (m, 3H), 2.10-2.01 (m, 3H), 1.84 (m, 1H), 1.68-1.57 (m, 3H), 1.46 (m, 1H), 1.39 (s, 9H, tert-butyl), 1.34, 1.32 (2s, 3H, 15-CH$_3$), 1.29-1.18 (m, 3H), 1.05 (s, 3H, 18-CH$_3$), 0.98 (m, 1H), 0.81 (d, 3H, 17-CH$_3$, J=7 Hz), 0.58 (d, 3H, 16-CH$_3$, J=7 Hz). MS-ESI (m/z): 732 (MNa$^+$).

Step C. 14-O-[(5-tert-Butoxycarbonylamino-2-oxo-cyclohexylsulfanyl)-acetyl]-mutilin 14-O-[(2-Benzoyloxy-5-tert-butoxycarbonylamino-cyclohex-1-en-ylsulfanyl)-acetyl]-mutilin (1 g, 1.41 mmol) was treated with 1.55 ml of aqueous 1M sodium hydroxide (1.55 mmol) according to Example 34 Step D. After work up and chromatography of the mixture (silica, toluene/ethyl acetate=5/1) the title compound (toluene/ethyl acetate=3/1, $R_f$=0.22, 0.6 g, 70% yield) was obtained as white foam.

$^1$H NMR (DMSO-$d_6$, 400 MHz, δ, ppm, inter alia): 6.89 (d, 0.5H, NH, J=6 Hz), 6.86 (d, 0.5H, J=8 Hz), 6.17-6.05 (m, 1H, 19-H), 5.51 (d, 1H, 14-H, J=8 Hz), 5.09-4.99 (m, 2H, 20-H), 4.47 (m, 1H, 11-OH), 3.92, 3.55 (2m, 1H, 1-H), 3.79 (m, 1H, 5'-H), 3.40 (t, 1H, 11-H, J=6 Hz), 3.35-3.12 (m, 2H), 2.77, 2.50 (2m, 1H), 2.41-1.90 (m,), 1.71-1.18 (m,), 1.37 (s, 9H, tert-butyl), 1.35 (s, 3H, 15-CH$_3$), 1.04 (s, 3H, 18-CH$_3$), 0.99 (m, 1H), 0.80 (d, 3H, 17-CH$_3$, J=7 Hz), 0.59 (d, 3H, 16-CH$_3$, J=6 Hz).

Step D. 14-O-[(5-Amino-2-oxo-cyclohexylsulfanyl)-acetyl]-mutilin

14-O-[(5-tert-Butoxycarbonylamino-2-oxo-cyclohexyl-sulfanyl)-acetyl]-mutilin (0.3 g, 0.5 mmol) was treated with 1.25 ml of 4M HCl in dioxane (5 mmol) according to the method of Example 32 Step F and stirred for 2 hours. After work up the title compound (0.26 g, quantitative yield, uncorrected) was obtained as white foam and was directly taken to the next step.

MS-ESI (m/z): 506.0 (MH$^+$).

Step E. 14-O-[(5-Amino-2-oxo-cyclohexylsulfanyl)-acetyl]-mutilin succinic acid salt A solution of succinic acid (59 mg, 0.5 mmol) in 5 ml of iso-propanol was added under stirring over a period of 5 min to a solution of 14-O-[(5-Amino-2-oxo-cyclohexylsulfanyl)-acetyl]-mutilin (0.26 g, 0.5 mmol) in 10 ml of methyl tert-butyl ether and 5 ml of isopropanol. The mixture was stirred for 4 h and stripped of the solvent. The residue was dissolved in 2 ml of isopropanol and 20 ml of methyl tert-butyl ether were added to it and stirred for 1 hour. The precipitate was filtered, washed with 5 ml of methyl tert-butyl ether and dried under vacuum to obtain the title compound (0.18 g, 58% yield) as a white solid.

$^1$H NMR (DMSO-$d_6$, 400 MHz, δ, ppm, inter alia): 6.18-6.05 (m, 1H, H-19), 5.52 (d, 1H, 14-H, J=7 Hz), 5.12-4.98 (m, 2H, 20-H), 4.50 (bs, 1H, 11-OH), 3.89, 3.53 (2m, 1H, 1'-H), 3.42-3.14 (m), 2.39 (s, 1H), 2.27 (s, 2H), 2.23-1.96 (m), 1.69-1.17 (m), 1.34 (s, 3H, 15-CH$_3$), 1-0.08 (s, 3H, 18-CH$_3$), 1.13-0.93 (m), 0.80 (d, 3H, 17-CH$_3$, J=7 Hz), 0.59 (d, 3H, 16-CH$_3$, J=6 Hz).

Example 36

14-O-{[(6R,8R)-8-Amino-1,4-dioxa-spiro[4.5]dec-6-ylsulfanyl]-acetyl}-mutilin succinic acid salt+(6S,8S) Diastereomer Succinic Acid Salt

Step A. Thiobenzoic acid S-((6R,8R)-8-tert-butoxy-carbonylamino-1,4-dioxa-spiro[4.5]dec-6-yl) ester+(6S,8S) Diastereomer A mixture of the compound of Example 35 Step A (2.00 g, 5.72 mmol), 1,2-ethandiol (2.0 ml, 35.8 mmol), 25 ml of dichloromethane and BF$_3$ (48% purity, 0.60 ml, 4.25 mmol) was stirred for 2 days. The mixture was diluted with dichloromethane and washed with saturated aqueous sodium bicarbonate and brine, dried and stripped of the solvent. After chromatography (silica, ethyl acetate/cyclohexane=1/9->15/85) the title compound (toluene/ethyl acetate=9/1, $R_f$=0.28, 632 mg, 28% yield) was obtained as foam.

$^1$H NMR (DMSO-$d_6$, 400 MHz, δ, ppm): 7.89 (m, 2H, aromatic H), 7.66 (t, 1H, aromatic H, J=8 Hz), 7.53 (t, 2H, aromatic H, J=8 Hz), 6.86 (d, 1H, NH, J=8 Hz), 4.04-3.83 (m, 5H), 3.48 (m, 1H), 2.09-1.40 (m, 6H), 1.35 (s, 9H, tert-butyl).

Step B. ((6R,8R)-6-Mercapto-1,4-dioxa-spiro[4.5]dec-8-yl)-carbamic acid tert-butyl ester+(6S,8S) Diastereomer A mixture of thiobenzoic acid S-((6R,8R)-8-tert-butoxy-carbonylamino-1,4-dioxa-spiro[4.5]dec-6-yl) ester+(6S,8S) diastereomer (695 mg, 1.77 mmol) and hydrazine (80% aq. solution, 0.10 ml, 2.65 mmol) in 7 ml of dichloromethane was stirred for 24 hours. The mixture was diluted with dichloromethane and washed with 1M aqueous HCl, dried and stripped of the solvent to obtain the title compound (490 mg, 95% yield) as yellow-gray oil.

$^1$H NMR (CDCl$_3$, 400 MHz, δ, ppm, inter alia): 4.34 (bs, 1H, NH), 4.13-4.05 (m, 2H), 3.95-3.85 (m, 2H), 3.49 (bs, 1H), 2.98 (m, 1H), 2.25 (m, 1H), 1.90-1.75 (m, 2H), 1.69-1.41 (m), 1.37 (s, 9H, tert-butyl).

Step C. 14-O-{[(6R,8R)-8-tert-Butoxycarbony-lamino-1,4-dioxa-spiro[4.5]dec-6-ylsulfanyl]-acetyl}-mutilin+(6S,8S) Diastereomer ((6R,8R)-6-Mercapto-1,4-dioxa-spiro[4.5]dec-8-yl)-carbamic acid tert-butyl ester+(6S,8S) diastereomer (410 mg, 1.42 mmol) was treated with pleuromutilin tosylate (910 mg, 1.71 mmol) according to the method of Example 1 Step A3 and stirred for 2.5 hours. The mixture was concentrated in vacuo and the residue was taken up in ethyl acetate, washed with water, 0.1M aqueous HCl, aqueous sodium bicarbonate and brine, dried and stripped of the solvent. After chromatography (silica, ethyl acetate/toluene=1/4) of the mixture the title compound ($R_f$=0.18, 613 mg, 66% yield) was obtained as pale yellow foam.

$^1$H NMR (DMSO-$d_6$, 400 MHz, δ, ppm, inter alia): 6.77 (bm, 1H, NH), 6.13 (dd, 1H, 19-H, J=11 Hz and 18 Hz), 5.54 (d, 1H, 14-H, J=8 Hz), 5.11-5.02 (m, 2H, H-20), 4.47 (m, 1H, 11-OH), 4.04-3.81 (m, 4H), 3.39 (m, 1H, 11-H), 3.35-3.17 (m, 3H), 3.02 (m, 1H), 2.39 (s, 1H, 4-H), 2.25-1.93 (m), 1.75-1.18 (m), 1.36 (2s, 12H, 15-CH$_3$, tert-butyl), 1.05-0.95 (m), 1.05 (s, 3H, 18-CH$_3$), 0.81 (d, 3H, 17-CH$_3$, J=7 Hz), 0.62 (d, 3H, 16-CH$_3$, J=7 Hz). MS-ESI (m/z): 672 (MNa$^+$).

Step D. 14-O-{[(6R,8R)-8-Amino-1,4-dioxa-spiro[4.5]dec-6-ylsulfanyl]-acetyl}-mutilin+(6S,8S) Diastereomer 14-O-{[(6R,8R)-8-tert-Butoxycarbonylamino-1,4-dioxa-spiro[4.5]dec-6-ylsulfanyl]-acetyl}-mutilin+(6S,8S) diastereomer (250 mg, 0.39 mmol) was treated with 1.5 ml trifluoroacetic acid according to the method of Example 1 Step B and stirred for 6 hours at room temperature. After work up and chromatography (silica, dichloromethane/methanol=19/1) the title compound (dichloromethane/methanol=9/1, $R_f$=0.15-0.54, 160 mg, 76% yield) was obtained as white foam, which was directly taken to the next step.

Step E. 14-O-{[(6R,8R)-8-Amino-1,4-dioxa-spiro[4.5]dec-6-ylsulfanyl]-acetyl}-mutilin succinic acid salt+(6S,8S) Diastereomer Succinic Acid Salt 14-O-{[(6R,8R)-8-Amino-1,4-dioxa-spiro[4.5]dec-6-ylsulfanyl]-acetyl}-mutilin+(6S,8S) diastereomer (120 mg, 0.22 mmol) was treated with succinic acid (25.7 mg, 0.22 mmol) according to the method of Example 35 Step E to obtain the title compound (100 mg, 69% yield) as a pale yellow solid.

$^1$H NMR (DMSO-d$_6$, 400 MHz, δ, ppm, inter alia): 6.16, 6.15 (2dd, 1H, 19-H, J=11 Hz and 18 Hz), 5.56 (d, 1H, 14-H, J=8 Hz), 5.14-5.02 (m, 2H, 20-H), 4.53 (bs), 4.08-3.85 (m), 3.48-3.21 (m), 3.12-3.01 (m), 2.42 (bs, 1H, 4-H), 2.30 (s, 4H, succinic acid), 2.26-2.02 (m), 1.84-1.21 (m), 1.38 (s, 3H, 15-CH$_3$), 1.08 (s, 3H, 18-CH$_3$), 0.83 (d, 3H, 17-CH$_3$, J=7 Hz), 0.64 (d, 3H, 16-CH$_3$, J=7 Hz).

Example 37

14-O-{[5-Amino-2-methoxy-cyclohexylsulfanyl]-acetyl}-mutilin and 14-O-{[4-Amino-2-methoxy-cyclohexylsulfanyl]-acetyl}-mutilin Step A. 14-O-{[5-tert-Butoxycarbonylamino-2-methoxy-cyclohexylsulfanyl]-acetyl}-mutilin and 14-O-{[4-tert-Butoxycarbonylamino-2-methoxy-cyclohexylsulfanyl]-acetyl}-mutilin An ice-cold solution of 14-O-{[(1R,2R,5S)-5-tert-butoxycarbonylamino-2-hydroxy-cyclohexylsulfanyl]-acetyl}-mutilin+(1S,2S,5R) diastereomer (4.00 g, 6.58 mmol) from Example 1 Step A in 120 ml of dichloromethane was treated with BF$_3$ (48% purity, 0.20 ml, 1.65 mmol) followed by trimethylsilyl diazomethane (2M in hexane, 0.82 ml, 1.64 mmol) under stirring. After 20 minutes 3 additional amounts of BF$_3$ (48% purity, 0.20 ml, 1.65 mmol) followed by 3 additional amounts of trimethylsilyl diazomethane (2M in hexane, 0.82 ml, 1.64 mmol) were added each time in time interval of 20 min. The mixture was stirred at room temperature for 30 min, charged with 200 ml of saturated aqueous sodium bicarbonate and stirred. The organic phase was separated and washed with saturated aqueous sodium bicarbonate, dried and stripped of the solvent to give a mixture. After chromatography (silica, ethyl acetate/cyclohexane=1/4->1/1) a mixture of the title compounds (0.49 g, 12% yield) was obtained as a mixture as white foam.

$^1$H NMR (DMSO-d$_6$, 500 MHz, δ, ppm, inter alia): 6.72 (bm, 1H, NH), 6.17-6.09 (2dd, 1H, 19-H, J=11 Hz and 18 Hz), 5.54 (2d, 1H, 14-H, J=8 Hz), 5.10-5.00 (m, 2H, 20-H), 4.49 (d, 11-OH, J=6 Hz), 3.50-3.17 (m), 3.21 (2s, 3H, OMe), 2.40 (bs, 1H, 4-H), 2.26-2.01 (m), 1.73-1.56 (m), 1.53-0.96 (m), 1.35 (2s, 12H, 15-CH$_3$, tert-butyl), 1.05 (s, 3H, 18-CH$_3$), 0.81 (d, 3H, 17-CH$_3$, J=7 Hz), 0.62 (d, 3H, 16-CH$_3$, J=7 Hz).

Step B. 14-O-{[5-tert-Butoxycarbonylamino-2-methoxy-cyclohexylsulfanyl]-acetyl}-mutilin and 14-O-{[4-tert-Butoxycarbonylamino-2-methoxy-cyclohexylsulfanyl]-acetyl}-mutilin 14-O-{[5-tert-Butoxycarbonylamino-2-methoxy-cyclohexylsulfanyl]-acetyl}-mutilin and 14-O-{[4-tert-Butoxycarbonylamino-2-methoxy-cyclohexylsulfanyl]-acetyl}-mutilin (80 mg, 0.13 mmol) was treated with 0.32 ml of 4M HCl in dioxane (1.28 mmol) according to the method of Example 32 Step F and stirred for 2 hours. After work up and chromatography (silica, ethyl acetate/methanol/28% aq NH$_3$=500/100/1) a mixture of the title compounds (12 mg, 18% yield, uncorrected) was obtained as white foam.

$^1$H NMR (DMSO-d$_6$, 500 MHz, δ, ppm, inter alia): 6.18-6.05 (m, 1H, 19-H), 5.55 (m, 1H, 14-H), 5.10-5.00 (m, 2H, 20-H), 4.58, 4.50 (2m, 1H, 11-OH), 3.55-3.20 (m), 2.86-2.72 (m), 2.44, 2.40 (2s, 1H, 4-H), 2.22-1.99 (m), 1.78-1.20 (m), 1.06, 1.05 (2s, 3H, 18-CH$_3$), 1.03 (m, 1H), 0.81 (m, 3H, 17-CH$_3$), 0.62 (m, 3H, 18-CH$_3$). MS-ESI (m/z): 522 (MH$^+$).

The invention claimed is:

1. A compound of formula (I)

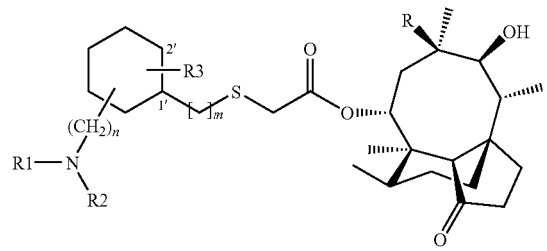

wherein n is 0 to 4;

m is 0 or 1 with the proviso that the sulphur atom and R$_3$ are in vicinal position, if m =0 then R$_3$ is in position 2', and if m =1 then R$_3$ is on position 1';

R is ethyl or vinyl;

R$_1$ is hydrogen or (C$_{1-6}$)alkyl,

R$_2$ is hydrogen or (C$_{3-6}$)cycloalkyl, or unsubstituted (C$_{1-6}$)alkyl, or (C$_{1-6}$)alkyl substituted by one or more of hydroxy, methoxy, halogen, or (C$_{3-6}$)cycloalkyl, or R$_1$ and R$_2$ together with the nitrogen atom to which they are attached form a 5 to 7 membered heterocyclic ring containing at least 1 nitrogen atom or 1 nitrogen and 1 additional heteroatom selected from N or O, or R$_1$ is hydroxy and R$_2$ is formyl;

R$_3$ is OH, OR$_4$, or a halogen atom, or

R$_3$ is bound to 2' and R$_3$ represents —O—(CH$_2$)$_p$—O— with p being 2 or 3; and R$_4$ is unsubstituted (C$_{1-6}$)alkyl or (C$_{3-6}$)cycloalkyl.

2. A compound of formula (II)

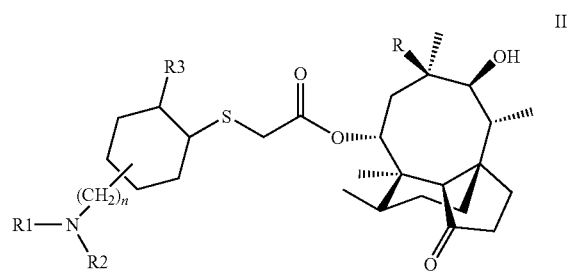

wherein n, R, R$_1$, R$_2$ and R$_3$ are as defined in claim 1.

3. A compound of formula (III)

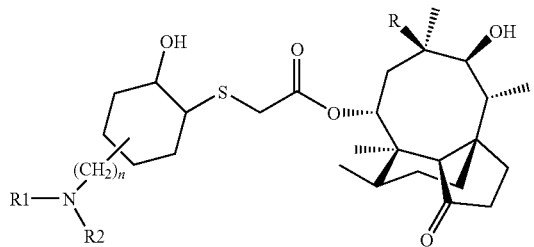

wherein n, R, R$_1$ and R$_2$ are as defined in claim 1.

4. A compound of formula (IV)

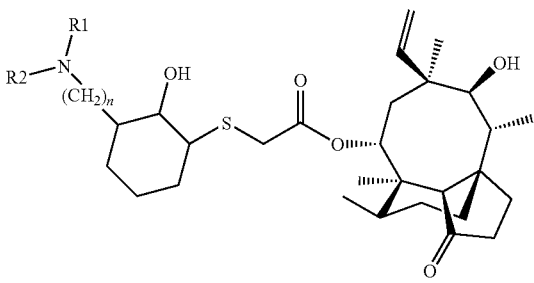

wherein n, R$_1$ and R$_2$ are as defined in claim 1.

5. A compound of formula (V)

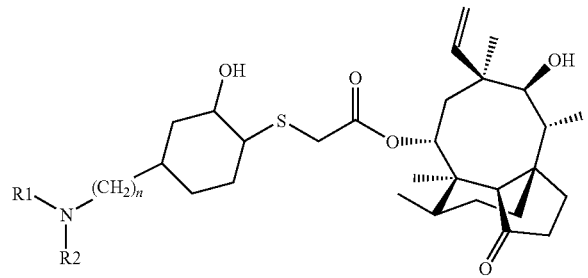

wherein n, R$_1$ and R$_2$ are as defined in claim 1.

6. A compound of formula (VI)

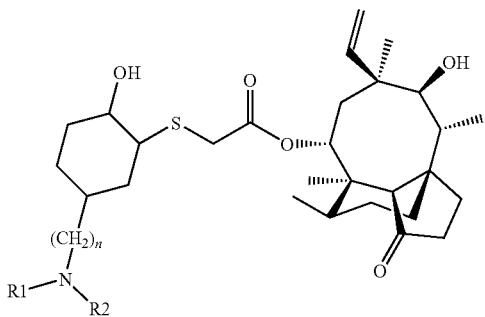

wherein n, R$_1$ and R$_2$ are as defined in claim 1.

7. A compound according to claim 1, selected from the group consisting of:
- 14-O-{[(1R, 2R, 4R)-4-Amino-2-hydroxy-cyclohexylsulfanyl]-acetyl}-mutilin;
- 14-O-{[(1S, 2S, 4S)-4-Amino-2-hydroxy-cyclohexylsulfanyl]-acetyl}-mutilin;
- 14-O-{[(1R, 2R, 5S)-5-Amino-2-hydroxy-cyclohexylsulfanyl]-acetyl}-mutilin;
- 14-O-{[(1S, 2S, 5R)-5-Amino-2-hydroxy-cyclohexylsulfanyl]-acetyl}-mutilin;
- 14-O-{[(1R, 2R, 4S)-4-Amino-2-hydroxy-cyclohexylsulfanyl]-acetyl}-mutilin and the (1S, 2S, 4R) diastereomer thereof;
- 14-O-{[(1R, 2R, 5R)-5-Amino-2-hydroxy cyclohexylsulfanyl]-acetyl}-mutilin;
- 14-O-{[(1S, 2S, 5S)-5-Amino-2-hydroxy-cyclohexylsulfanyl]-acetyl}-mutilin;
- 14-O-{[(1R, 2R, 3R)-3-Amino-2-hydroxy-cyclohexylsulfanyl]-acetyl}-mutilin and the (1S, 2S, 3S) diastereomer thereof;
- 14-O-{[(1R, 2R, 4R)-4-Diethylamino-2-hydroxy-cyclohexylsulfanyl]-acetyl}-mutilin and the (1S, 2S, 4S) diastereomer thereof;
- 14-O-{[(1R, 2R, 4R)-4-Ethylamino-2-hydroxy-cyclohexylsulfanyl]-acetyl}-mutilin and the (1S, 2S, 4S) diastereomer thereof;
- 14-O-{[(1R, 2R, 5S)-5-Ethylamino-2-hydroxy-cyclohexylsulfanyl]-acetyl}-mutilin and the (1S, 2S, 5R) diastereomer thereof;
- 14-O-{[(1R, 2R, 5S)-5-Diethylamino-2-hydroxy-cyclohexylsulfanyl]-acetyl}-mutilin and the (1S, 2S, 5R) diastereomer thereof;
- 14-O-{[(1R, 2R, 4S)-4-Diethylamino-2-hydroxy-cyclohexylsulfanyl]-acetyl}-mutilin and the (1S, 2S, 4R) diastereomer thereof;
- 14-O-{[(1R, 2R, 5R)-5-Diethylamino-2-hydroxy-cyclohexylsulfanyl]-acetyl}-mutilin and the (1S, 2S, 5S) diastereomer thereof;
- 14-O-{[(1R, 2R, 3R)-3-Ethylamino-2-hydroxy-cyclohexylsulfanyl]-acetyl}-mutilin and the (1S, 2S, 3S) diastereomer thereof;
- 14-O-{[(1R, 2R, 3R)-3-Diethylamino-2-hydroxy-cyclohexylsulfanyl]-acetyl}-mutilin and the (1S, 2S, 3S) diastereomer thereof;
- 14-O-{[(1R, 2R, 4S)-4-(Formyl-hydroxy-amino)-2-hydroxy-cyclohexylsulfanyl]-acetyl}-mutilin and the (1S, 2S, 4R) diastereomer thereof;
- 14-O-{[(1R, 2R, 5S)-5-(Formyl-hydroxy-amino)-2-hydroxy-cyclohexylsulfanyl]-acetyl}-mutilin and the (1S, 2S, 5R) diastereomer thereof;
- 14-O-{[(1R, 2R, 3R/S)-3-(Formyl-hydroxy-amino)-2-hydroxy-cyclohexylsulfanyl]-acetyl}-mutilin and the (1S, 2S, 3R/S) diastereomer thereof;
- 14-O-{[(1R, 2R, 5S)-2-Hydroxy-5-methylamino-cyclohexylsulfanyl]-acetyl}-mutilin and the (1S, 2S, 5R) diastereomer thereof;
- 14-O-{[(1R, 2R, 5S)-5-Allylamino-2-hydroxy-cyclohexylsulfanyl]-acetyl}-mutilin and the (1S, 2S, 5R) diastereomer thereof;
- 14-O-{[(1R, 2R, 5S)-2-Hydroxy-5-(2-methoxy-ethylamino)-cyclohexylsulfanyl]acetyl}-mutilin and the (1S, 2S, 5R) diastereomer thereof;
- 14-O-{[(1R, 2R, 4R*)-2-Hydroxy-4-(2-hydroxy-ethylamino)-cyclohexylsulfanyl]-acetyl}-mutilin and the (1S, 2S, 4S*) diastereomer thereof;

14-O-{[(1R, 2R, 4R*)-4-Cyclohexylamino-2-hydroxy-cyclohexylsulfanyl]-acetyl}-mutilin and the (1S, 2S, 4S*) diastereomer thereof;

14-O-{[(1R, 2R, 4R*)-4-Cyclopropylamino-2-hydroxy-cyclohexylsulfanyl]-acetyl}-mutilin and the (1S, 2S, 4S*) diastereomer thereof;

14-O-{[(1R, 2R, 5S*)-4-Cyclopropylamino-2-hydroxy-cyclohexylsulfanyl]-acetyl}-mutilin and the (1S, 2S, 5R*) diastereomer thereof;

14-O-{[(1R, 2R, 4S*)-4-Cyclopropylamino-2-hydroxy-cyclohexylsulfanyl]-acetyl}-mutilin and the (1S, 2S, 4R*) diastereomer thereof;

14-O-{[(1R, 2R, 5R*)-2-Hydroxy-5-morpholin-4-yl-cyclohexylsulfanyl]-acetyl}-mutilin and the (1S, 2S, 5S*) diastereomer thereof;

14-O-{[(1R, 2R, 5S *)-2-Hydroxy-5-morpholin-4-yl-cyclohexylsulfanyl]-acetyl}-mutilin and the (1S, 2S, 5R*) diastereomer thereof;

14-O-{[(1R, 2R, 5S)-5-Amino-2-hydroxy-cyclohexylsulfanyl]-acetyl}-19,20-dihydro-mutilin and the (1S, 2S, 5R) diastereomer thereof;

14-O-{[(1R, 2R, 5S)-5-Ethylamino-2-hydroxy-cyclohexylsulfanyl]-acetyl}-19,20-dihydro-mutilin and the (1S, 2S, 5R) diastereomer thereof;

14-O-{[(1R, 2R, 5R)-5-Amino-2-hydroxy-cyclohexylsulfanyl]-acetyl}-19,20-dihydro-mutilin and the (1S, 2S, 5S) diastereomer thereof;

14-O-{[(1R, 2R)-4-Aminomethyl-2-hydroxy-cyclohexylsulfanyl]-acetyl}-mutilin and the (1S, 2S) diastereomers thereof;

14-O-{[5-Amino-2-chloro-cyclohexylsulfanyl]-acetyl}-mutilin;

14-O-{[4-Amino-2-chloro-cyclohexylsulfanyl]-acetyl}-mutilin;

14-O-[(4-Amino-1-hydroxy-cyclohexylmethylsulfanyl)-acetyl]-mutilin;

14-O-{[(1R, 2R)-2-Hydroxy-5-(3 -methylamino-propyl)-cyclohexylsulfanyl]-acetyl}-mutilin and the (1S, 2S) diastereomers thereof;

14-O-{[(1R, 2R)-2-Hydroxy-4-(3 -methylamino-propyl)-cyclohexylsulfanyl]-acetyl}-mutilin and the (1S, 2S) diastereomers thereof;

14-O-{[(1R, 2R)-5-(3-Amino-propyl)-2-hydroxy-cyclohexylsulfanyl]-acetyl}-mutilin and the (1S, 2S) diastereomers thereof;

14-O-{[(1R, 2R)-4-(3-Amino-propyl)-2-hydroxy-cyclohexylsulfanyl]-acetyl}-mutilin and the (1S, 2S) diastereomer thereof;

14-O-{[(6R, 8R)-8-Amino-1,4-dioxa-spiro[4.5]dec-6-ylsulfanyl]-acetyl}-mutilin and the (6S, 8S) diastereomer thereof;

14-O-{[4-Amino-2-methoxy-cyclohexylsulfanyl]-acetyl}-mutilin; and

14-O-{[5-Amino-2-methoxy-cyclohexylsulfanyl]-acetyl}-mutilin.

8. The compound according to claim 1 in the form of a salt.

9. A compound according to claim 1 in the form of a pharmaceutical drug substance.

10. A pharmaceutical drug composition comprising a compound of claim 1 in association with at least one pharmaceutical excipient.

11. A pharmaceutical drug composition according to claim 10, further comprising another pharmaceutically active agent.

* * * * *